(12) United States Patent
Cardoso et al.

(10) Patent No.: US 11,904,287 B2
(45) Date of Patent: *Feb. 20, 2024

(54) CAPSULES

(71) Applicant: The Procter & Gamble Company, Cincinnati, OH (US)

(72) Inventors: Mariana B T Cardoso, Ixelles (BE); Andre Martim Barros, Woluwe Saint Etienne (BE); Peter De Nies, Antwerp (BE); Pierre Daniel Verstraete, Lambert (BE); Valerie Wong, Mason, OH (US); Steven Daryl Smith, Fairfield, OH (US); Isabelle Guimet, Gilles (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/851,173

(22) Filed: Apr. 17, 2020

(65) Prior Publication Data

US 2020/0330948 A1 Oct. 22, 2020

Related U.S. Application Data

(60) Provisional application No. 62/913,191, filed on Oct. 10, 2019, provisional application No. 62/835,011, filed on Apr. 17, 2019.

(51) Int. Cl.
*B01J 13/06* (2006.01)
*C11B 9/00* (2006.01)

(52) U.S. Cl.
CPC ............. *B01J 13/06* (2013.01); *C11B 9/00* (2013.01)

(58) Field of Classification Search
CPC ........................... B01J 13/06; C11B 9/00
See application file for complete search history.

(56) References Cited

U.S. PATENT DOCUMENTS

| | | |
|---|---|---|
| 5,500,223 A | 3/1996 | Behan et al. |
| 6,243,909 B1 | 6/2001 | Graham et al. |
| 6,537,583 B1 | 3/2003 | Dupuis et al. |
| 8,425,940 B2 | 4/2013 | Lapidot et al. |
| 8,931,971 B2 | 1/2015 | Schwarz et al. |
| 9,603,784 B2 | 3/2017 | Shimizu et al. |
| 10,046,291 B2 | 8/2018 | Yamazaki |
| 10,285,928 B2 | 5/2019 | Marsh et al. |
| 2004/0163674 A1 | 8/2004 | Policicchio et al. |
| 2005/0158369 A1 | 7/2005 | Dorschner et al. |
| 2006/0188551 A1 | 8/2006 | Hauser et al. |

(Continued)

FOREIGN PATENT DOCUMENTS

| | | |
|---|---|---|
| CA | 2980792 A1 | 2/2010 |
| CN | 103432970 A | 12/2013 |

(Continued)

OTHER PUBLICATIONS

European Search Report and Written Opinion for EP 19169888, dated Dec. 17, 2019, 12 pgs.

(Continued)

*Primary Examiner* — Arrie L Reuther
(74) *Attorney, Agent, or Firm* — Kathleen Y. Carter; James E. Oehlenschlager

(57) ABSTRACT

A population of capsules, the capsules can include a core including a benefit agent and a shell surrounding the core, wherein the shell can include a first shell component.

24 Claims, 12 Drawing Sheets

(56) References Cited

U.S. PATENT DOCUMENTS

| | | |
|---|---|---|
| 2007/0082033 A1 | 4/2007 | Doerschner et al. |
| 2008/0096780 A1 | 4/2008 | Veugelers et al. |
| 2009/0247449 A1 | 10/2009 | Burdis |
| 2010/0143422 A1 | 6/2010 | Popplewell et al. |
| 2010/0247660 A1 | 9/2010 | Lei et al. |
| 2011/0104221 A1 | 5/2011 | Galeone et al. |
| 2011/0118161 A1 | 5/2011 | Looft |
| 2011/0177951 A1 | 7/2011 | Toledano |
| 2012/0104639 A1 | 5/2012 | Traynor et al. |
| 2012/0128747 A1 | 5/2012 | Veronique et al. |
| 2012/0202695 A1 | 8/2012 | Toledano |
| 2012/0237578 A1 | 9/2012 | Lei |
| 2013/0040817 A1 | 2/2013 | Dreher |
| 2014/0044761 A1 | 2/2014 | Lei et al. |
| 2014/0331414 A1 | 11/2014 | Bone |
| 2014/0338134 A1 | 11/2014 | Fernandez Prieto et al. |
| 2014/0342972 A1 | 11/2014 | Smets |
| 2016/0168509 A1 | 6/2016 | Hitchcock |
| 2016/0168510 A1 | 6/2016 | Tasker et al. |
| 2016/0168511 A1 | 6/2016 | Hitchcock et al. |
| 2016/0184196 A1 | 6/2016 | Baxter et al. |
| 2016/0303531 A1 | 10/2016 | Yamazaki |
| 2016/0317993 A1 | 11/2016 | Rotello et al. |
| 2018/0085291 A1 | 3/2018 | Sasaki |
| 2018/0207451 A1 | 7/2018 | Toledano |
| 2018/0339176 A1 | 11/2018 | Toledano |
| 2020/0114328 A1 | 4/2020 | Jerri et al. |
| 2020/0129947 A1 | 4/2020 | Ouali et al. |
| 2020/0255776 A1 | 8/2020 | Schmiedel et al. |
| 2022/0119741 A1 | 4/2022 | Smets et al. |
| 2022/0119742 A1 | 4/2022 | Smets et al. |

FOREIGN PATENT DOCUMENTS

| | | |
|---|---|---|
| CN | 105612248 A | 5/2016 |
| CN | 105734540 A | 7/2016 |
| CN | 107001979 A | 8/2017 |
| CN | 107249545 B | 5/2021 |
| EP | 1767613 A1 | 3/2007 |
| EP | 1767614 A1 | 3/2007 |
| EP | 2078696 A1 | 7/2009 |
| EP | 3181674 A1 | 6/2017 |
| EP | 2865423 B1 | 3/2020 |
| WO | 0145615 A1 | 6/2001 |
| WO | 2005044220 A1 | 5/2005 |
| WO | 2007019201 A1 | 2/2007 |
| WO | 2009106318 A2 | 9/2009 |
| WO | WO2011154421 A1 | 12/2011 |
| WO | 2013078551 A1 | 6/2013 |
| WO | 2013083760 A2 | 6/2013 |
| WO | 2013174921 A1 | 11/2013 |
| WO | 2016100477 A1 | 6/2016 |
| WO | 2016100479 A1 | 6/2016 |
| WO | 2017016636 A1 | 2/2017 |
| WO | 2017075074 A1 | 5/2017 |
| WO | WO2018189588 A1 | 10/2018 |
| WO | 2018231886 A1 | 12/2018 |
| WO | 2020077451 A1 | 4/2020 |
| WO | 2020214876 A1 | 10/2020 |
| WO | 2020214877 A1 | 10/2020 |
| WO | 2020214878 A1 | 10/2020 |

OTHER PUBLICATIONS

European Search Report and Written Opinion for EP 19169894, dated Dec. 17, 2019, 12 pgs.

European Search Report and Written Opinion, EP 19169897, dated Oct. 1, 2019, 8 pgs.

Jyothi et al., "Microencapsulation techniques, factors influencing encapsulation efficiency", Journal of Microencapsulation, 27:3, pp. 187-197.

Thompson et al., "Colloidosomes: Synthesis, properties and applications", Journal of Colloid and Interface Science, 447, 2015, pp. 217-228.

International Search Report and Written Opinion; Application Ser. No. PCT/US2020/028619; dated Jun. 30, 2020, 18pages.

Liu, M.: "Understanding the Mechanical Strength of Microcapsules and their Adhesion on Fabric Surfaces",2010, University of Birmingham, XP055511234, cited in the application, pp. 1-282.

All Office Actions; U.S. Appl. No. 16/851,176.

All Office Actions; U.S. Appl. No. 16/851,194.

U.S. Appl. No. 16/851,176, filed Apr. 17, 2020, Mariana B T Cardoso et al.

U.S. Appl. No. 16/851,194, filed Apr. 17, 2020, Mariana B T Cardoso et al.

All Office Actions; U.S. Appl. No. 17/498,016, filed Oct. 11, 2021.

U.S. Appl. No. 17/500,984, filed Sep. 14, 2021, to Jonathan Robert Cetti et al.

All Office Actions; U.S. Appl. No. 17/500,970, filed Oct. 14, 2021.

All Office Actions; U.S. Appl. No. 17/500,979, filed Oct. 14, 2021.

All Office Actions; U.S. Appl. No. 17/500,984, filed Oct. 14, 2021.

All Office Actions; U.S. Appl. No. 17/501,202, filed Oct. 14, 2021.

U.S. Appl. No. 17/498,016, filed Oct. 11, 2021, to Steven Daryl Smith et . al.

U.S. Appl. No. 17/500,970, filed Oct. 14, 2021, to Andre Martim Barros et. al.

U.S. Appl. No. 17/500,979, filed Oct. 14, 2021, to Andre Martim Barros et. al.

U.S. Appl. No. 17/501,202, filed Oct. 14, 2021, to Andre Martim Barros et. al.

All Office Actions; U.S. Appl. No. 17/727,857, filed Apr. 25, 2022.

U.S. Appl. No. 17/727,857, filed Apr. 25, 2022, to Mariana B T Cardoso et al.

All Office Actions; U.S. Appl. No. 18/115,890, filed Mar. 1, 2023.

U.S. Appl. No. 18/115,890, filed Mar. 1, 2023, to Mariana B T Cardoso et. al.

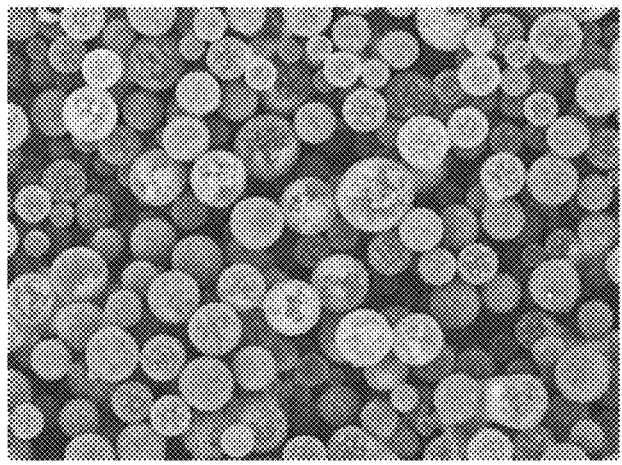
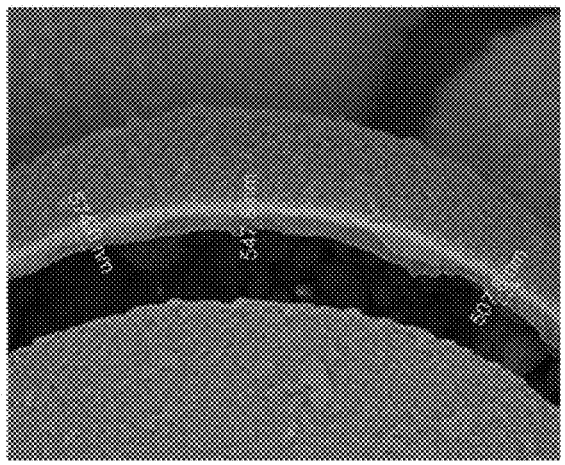
FIGURE 4A             FIGURE 4B
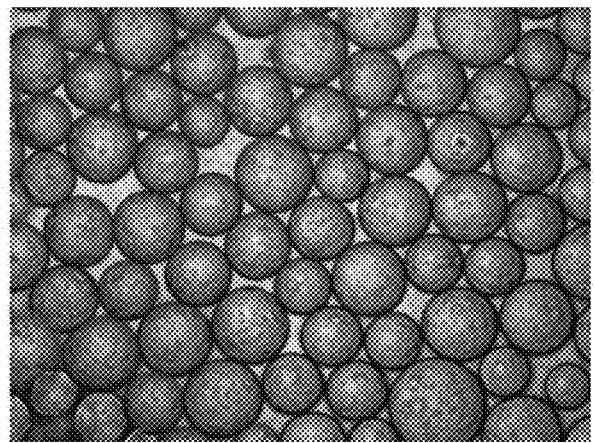
FIGURE 5

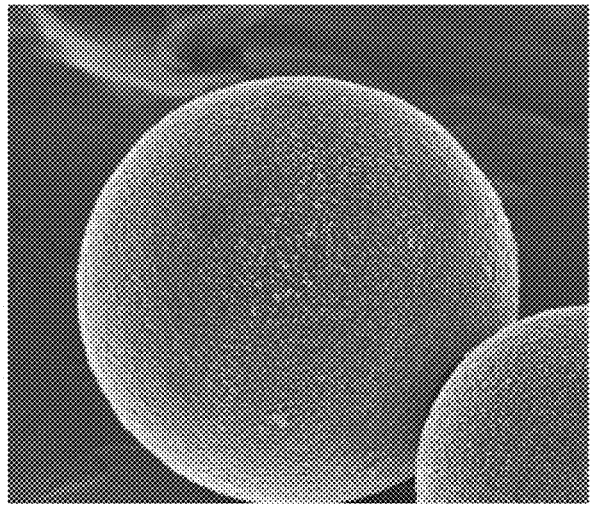
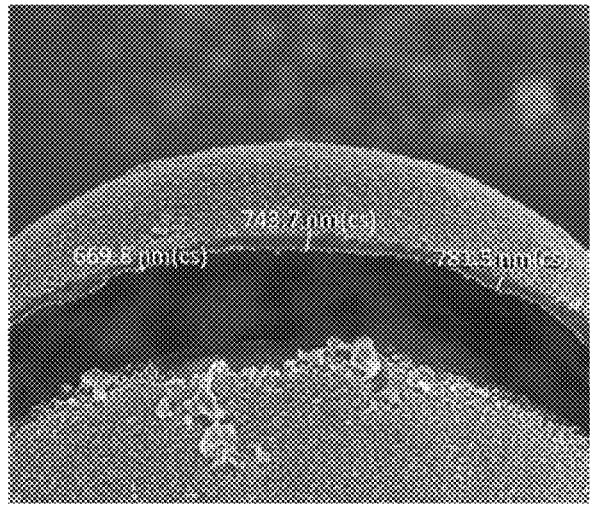
FIGURE 8A  FIGURE 8B
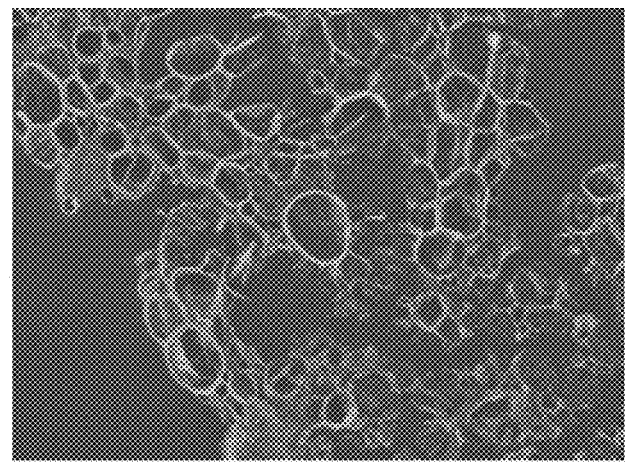
FIGURE 9

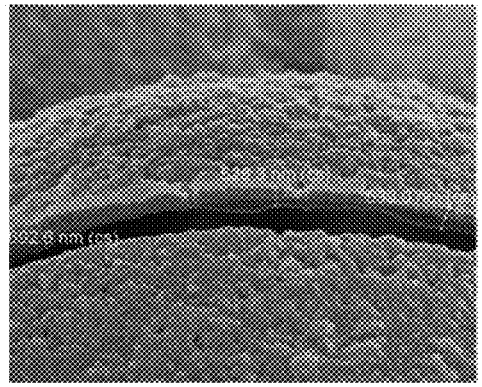 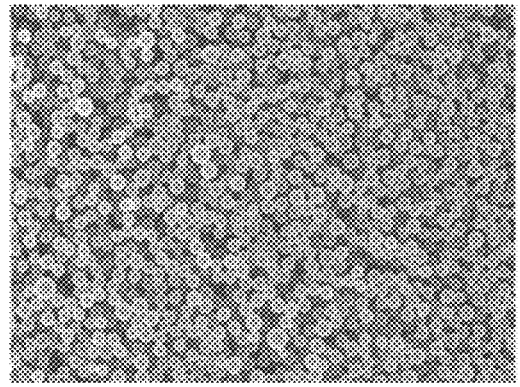
FIGURE 15A    FIGURE 15B
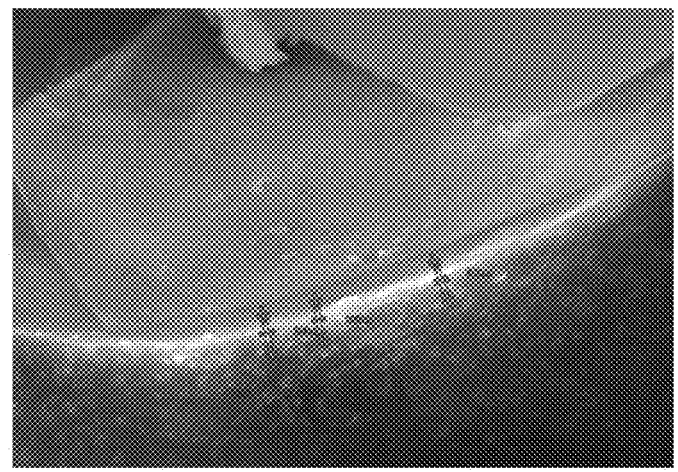
FIGURE 16

CAPSULES

FIELD OF THE DISCLOSURE

The disclosure relates to capsules and methods of making capsules for the transfer and triggered release of benefit agents.

BACKGROUND

Microencapsulation is a process where droplets of liquids, particles of solids or gasses are enclosed inside a solid shell and are generally in the micro-size range. The core material is then mechanically separated from the surrounding environment (Jyothi et al., *Journal of Microencapsulation*, 2010, 27, 187-197). Microencapsulation technology is attracting attention from various fields of science and has a wide range of commercial applications for different industries. Overall, capsules are capable of one or more of (i) providing stability of a formulation or material via the mechanical separation of incompatible components, (ii) protecting the core material from the surrounding environment, (iii) masking or hiding an undesirable attribute of an active ingredient and (iv) controlling or triggering the release of the active ingredient to a specific time or location. All of these attributes can lead to an increase of the shelf-life of several products and a stabilization of the active ingredient in liquid formulations.

Encapsulation can be found in areas such as pharmaceuticals, personal care, textiles, food, coatings and agriculture. In addition, the main challenge faced by microencapsulation technologies in real-world commercial applications is that a complete retention of the encapsulated active within the capsule is required throughout the whole supply chain, until a controlled or triggered release of the core material is applied (Thompson et al., *Journal of Colloid and Interface Science*, 2015, 447, 217-228). There are significantly limited microencapsulation technologies that are safe for both the environment and human health with a long-term retention and active protection capability that can fulfill the needs of the industry nowadays, especially when it comes to encapsulation of small molecules.

Over the past several years, consumer goods manufacturers have used core-shell encapsulation techniques to preserve actives, such as benefit agents, in harsh environments and to release them at the desired time, which may be during or after use of the consumer goods. Among the several mechanisms that can be used for release of benefit agent, the one commonly relied upon is mechanical rupture of the capsule shell. Selection of mechanical rupture as the release mechanism constitutes another challenge to the manufacturer, as rupture must occur at specific desired times, even if the capsules are subject to mechanical stress prior to the desired release time.

Industrial interest for encapsulation technology has led to the development of several polymeric capsules chemistries which attempt to meet the requirements of low shell permeability, high deposition, targeted mechanical properties and rupture profile. Increased environmental concerns have put the polymeric capsules under scrutiny, therefore manufacturers have started investigating sustainable solutions for the encapsulation of benefit agents. There is ample literature on sustainable capsules based on metal oxide or semi-metal oxides, mainly silica capsules; however, none of the capsules described in the literature provides the right balance of low shell permeability, mechanical properties, deposition, and rupture profile.

Capsules made with silane monomers only are known in the art. Multiple patent applications and academic publications disclose the use of monomers such as tetramethoxysilane (TMOS) and tetraethoxysilane (TEOS). The advantage of using such monomers is that they react faster than prepolymers made from similar monomers, and as such have been the favored option for years. This fast reaction time is due to their higher water solubility once partially hydrolyzed compared to larger precursors, due to the fact that the former have lower molecular weights, which accelerate further the overall hydrolysis kinetics as they are in an excess of water once dispersed in said phase. However, these types of disclosures often use cationic surfactants such as cetyltrimethylammonium chloride (CTAC) or cetyltrimethylammonium bromide (CTAB), supposedly to drive the negatively charged hydrolyzed intermediate reaction species that are dispersed in the water phase towards the oil/water interface.

Without wishing to be bound by theory, what is often the case is that the partially hydrolyzed monomers that are in an excess of water start condensing and forming ever larger particulate sols that are drawn to oil/water interfaces. Ultimately, the system desires to reduce surface energies of dispersed particulate sols by virtue of thermodynamic laws, which favors having the sols at the oil/water interfaces, especially when they grow large. The formation of such particulate sols can eventually lead to a shell around oil droplets and in some cases even shells that are strong enough towards mechanical self-integrity. However, by virtue of the geometrical properties (size, fractal dimensions, shapes etc.) of particulate sols, they are not able to form shells with a dense non-porous network that would provide low shell permeability.

In addition, WO 2011/131644 discloses capsules with a semi-metal organic shell by joining together nanoparticles with the use of an oil soluble semi-metal precursor. However, the reference does not disclose a second shell component. In the present invention it has been found that a selective choice of nanoparticles and precursors coupled with a second shell component provides capsules that have reduced permeability and increased mechanical integrity.

Without wishing to be bound by theory, the applicant has surprisingly found that a careful selection of primary shell components, secondary shell components, nanoparticles, core-shell ratio, and thickness of the shell allows production of metal oxide or semi-metal oxide based capsules which hold their mechanical integrity once left air-drying on a surface and have low shell permeability in surfactant-based matrices. These two properties are the desired results but are also characteristics of a dense and strong shell with low permeability made possible only by the judicious choice of component materials and conditions to assemble them.

SUMMARY

A population of capsules is provided, the capsules comprising an oil-based core comprising a benefit agent, and a substantially inorganic shell surrounding the core, wherein the shell comprises a first shell component comprising at least one of a metal oxide or a semi-metal oxide, wherein the first shell component comprises up to 5 wt % of organic content; wherein said population has a mean volume weighted capsule diameter of about 10 micrometers to about 200 micrometers, an average shell thickness of about 170 nm to about 1000 nm; and wherein the mean volumetric core-shell ratio is from about 80:20 to about 98:2.

A population of capsules is provided, the capsules comprising a water-based core comprising a benefit agent, and a substantially inorganic shell surrounding the core, wherein the shell comprises a first shell component comprising at least one of a metal oxide or a semi-metal oxide, wherein the first shell component comprises up to about 5 wt % of organic content; wherein said population has a mean volume weighted capsule diameter of about 10 micrometers to about 200 micrometers, an average shell thickness of about 170 nm to about 1000 nm; and wherein the mean volumetric core-shell ratio is from about 80:20 to about 98:2.

A population of capsules is provided, the capsules comprising an oil-based core comprising a benefit agent, and a substantially inorganic shell surrounding the core, wherein the shell comprises a first shell component comprising at least one of a metal oxide or a semi-metal oxide, wherein the first shell component comprises up to 5 wt % of organic content; wherein said population has a mean volume weighted capsule diameter of about 10 micrometers to about 200 micrometers, an average shell thickness of about 170 nm to about 1000 nm; and wherein the mean volumetric core-shell ratio is from about 80:20 to about 98:2; wherein the first shell component comprises a condensed layer comprising a condensation product of a precursor of at least one of formula (I) or formula (II) or both:

$$(M^vO_zY_n)_w \quad \text{(Formula I)},$$

where M is one or more of silicon, titanium and aluminum, v is the valence number of M and is 3 or 4, z is from 0.5 to 1.6, each Y is independently selected from —OH, —OR$^2$, halo,

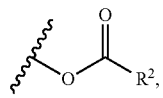

—NH$_2$, —NHR$^2$, —N(R$^2$)$_2$, and

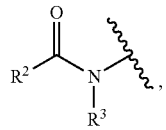

wherein R$^2$ is a C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, R$^3$ is a H, C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, n is from 0.7 to (v-1), and w is from 2 to 2000;

$$(M^vO_zY_nR^1_p)_w \quad \text{(Formula II)},$$

where M is one or more of silicon, titanium and aluminum, v is the valence number of M and is 3 or 4, z is from 0.5 to 1.6, each Y is independently selected from —OH, —OR$^2$, halo,

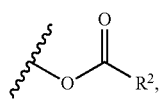

NH$_2$, —NHR$^2$, —N(R$^2$)$_2$,

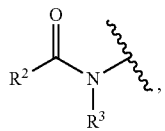

wherein R$^2$ is selected from a C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, R$^3$ is a H, C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, n is from 0 to (v-1), each R$^1$ is independently selected from a C$_1$ to C$_{30}$ alkyl, a C$_1$ to C$_{30}$ alkylene, a C$_1$ to C$_{30}$ alkyl substituted with one or more of a halogen, —OCF$_3$, —NO$_2$, —CN, —NC, —OH, —OCN, —NCO, alkoxy, epoxy, amino, mercapto, acryloyl, CO$_2$H, CO$_2$alkyl, aryl, and heteroaryl, or a C$_1$ to C$_{30}$ alkylene substituted with one or more of a halogen, —OCF$_3$, —NO$_2$, —CN, —NC, —OH, —OCN, —NCO, alkoxy, epoxy, amino, mercapto, acryloyl, CO$_2$H, CO$_2$alkyl, aryl, and heteroaryl, p is present in an amount up to pmax, and w is from 2 to 2000; wherein pmax=60/[9*Mw(R$^1$)+8], where Mw(R$^1$) is the molecular weight of the R group.

A population of capsules is provided, the capsules comprising a water-based core comprising a benefit agent, and a substantially inorganic shell surrounding the core, wherein the shell comprises a first shell component comprising at least one of a metal oxide or a semi-metal oxide, wherein the first shell component comprises up to about 5 wt % of organic content; wherein said population has a mean volume weighted capsule diameter of about 10 micrometers to about 200 micrometers, an average shell thickness of about 170 nm to about 1000 nm; and wherein the mean volumetric core-shell ratio is from about 80:20 to about 98:2; wherein the first shell component comprises a condensed layer comprising a condensation product of a precursor of at least one of formula (I) or formula (II) or both:

$$(M^vO_zY_n)_w \quad \text{(Formula I)},$$

where M is one or more of silicon, titanium and aluminum, v is the valence number of M and is 3 or 4, z is from 0.5 to 1.6, each Y is independently selected from —OH, —OR$^2$, halo,

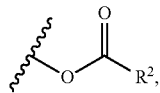

—NH$_2$, —NHR$^2$, —N(R$^2$)$_2$, and

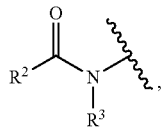

wherein R$^2$ is a C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, R$^3$ is a H, C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, n is from 0.7 to (v-1), and w is from 2 to 2000;

$$(M^vO_zY_nR^1_p)_w \quad \text{(Formula II)},$$

where M is one or more of silicon, titanium and aluminum, v is the valence number of M and is 3 or 4, z is from 0.5 to 1.6, each Y is independently selected from —OH, —OR², halo,

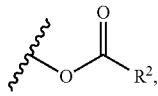

NH₂, —NHR², —N(R²)₂,

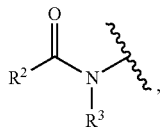

wherein $R^2$ is selected from a $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, $R^3$ is a H, $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, n is from 0 to (v-1), each $R^1$ is independently selected from a $C_1$ to $C_{30}$ alkyl, a $C_1$ to $C_{30}$ alkylene, a $C_1$ to $C_{30}$ alkyl substituted with one or more of a halogen, —OCF₃, —NO₂, —CN, —NC, —OH, —OCN, —NCO, alkoxy, epoxy, amino, mercapto, acryloyl, CO₂H, CO₂alkyl, aryl, and heteroaryl, or a $C_1$ to $C_{30}$ alkylene substituted with one or more of a halogen, —OCF₃, —NO₂, —CN, —NC, —OH, —OCN, —NCO, alkoxy, epoxy, amino, mercapto, acryloyl, CO₂H, CO₂alkyl, aryl, and heteroaryl, p is present in an amount up to pmax, and w is from 2 to 2000; wherein pmax=60/[9*Mw($R^1$)+8], where Mw($R^1$) is the molecular weight of the R group.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 4A is a scanning electron microscopy image of capsules of Sample E in accordance with embodiments of the disclosure;

FIG. 4B is a scanning electron microscopy image of a capsule shell of Sample E in accordance with embodiments of the disclosure;

FIG. 5 is an optical microscopy image of capsules of Sample C in accordance with embodiments of the disclosure;

FIG. 8A is scanning electron microscopy images of capsules of Sample H with both first and second shell component in accordance with embodiments of the disclosure;

FIG. 8B is scanning electron microscopy images of a capsule shell of Sample H with both first and second shell component in accordance with embodiments of the disclosure;

FIG. 9 is a scanning electron microcopy image of capsules of Comparative Example Sample W in accordance with embodiments of the disclosure;

FIG. 15A is a scanning electron microscopy image of a capsule shell of Sample B in accordance with embodiments of the disclosure;

FIG. 15B is a scanning electron microscopy image of capsules of Sample B in accordance with embodiments of the disclosure;

FIG. 16 is a scanning electron microscopy image of a capsule shell of Sample AW in accordance with embodiments of the disclosure;

DETAILED DESCRIPTION

Figure 1A:
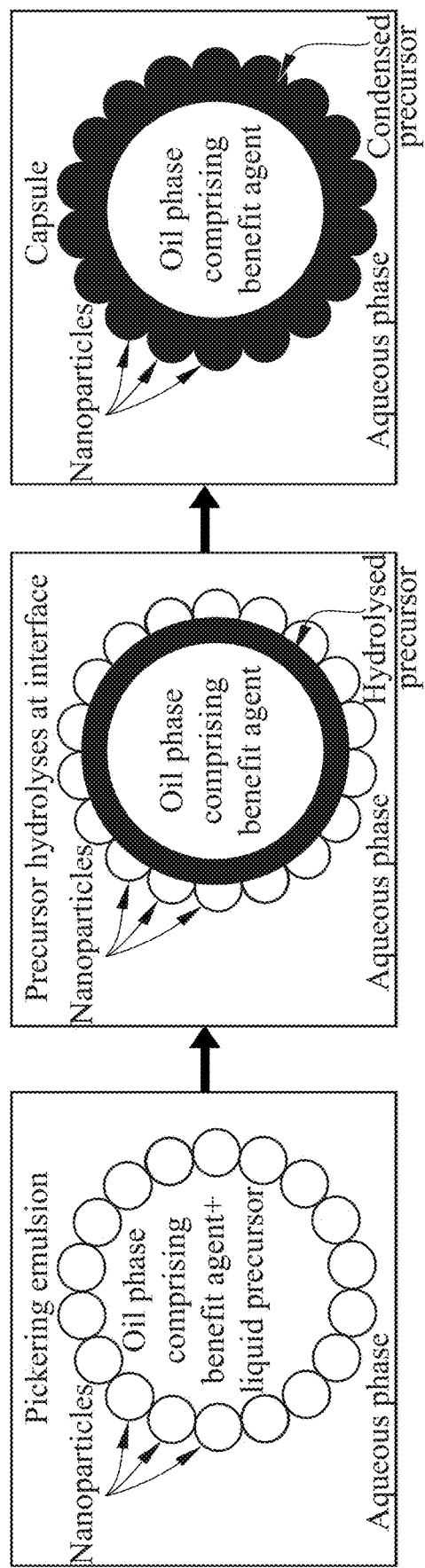
FIG. 1A is a schematic illustration of the method of making capsules in accordance with an embodiment of the disclosure prepared with a hydrophobic core.

In accordance with embodiments, inorganic capsules having a core surrounded by a shell are provided. The core can include one or more benefit agents. In various embodiments, the shell can include a first shell component and optionally a second shell component that surrounds the first shell component. In embodiments, the first shell component can include a condensed layer formed from the condensation product of a precursor. As described in detail below, the precursor can include one or more precursor compounds. In embodiments, the first shell component can include a nanoparticle layer. In embodiments, the second shell component can include inorganic materials.

Capsules of this invention are defined as comprising a substantially inorganic shell comprising a first shell component and a second shell component. By substantially inorganic it is meant that the first shell component can comprise up to 10 wt %, preferably 9 wt %, preferably 8 wt %, preferably 7 wt %, preferably 6 wt %, preferably 5 wt %, preferably 4 wt %, preferably 3 wt %, preferably 2 wt % preferably 1 wt % of organic content, as defined later in the organic content calculation and later in the descriptions. While the first shell component is useful to build a mechanically robust scaffold or skeleton, it can also provide low shell permeability in liquid products containing surfactants such as laundry detergents, shower-gels, cleansers, etc . . . (see Surfactants in Consumer Products, J. Falbe, Springer-Verlag). The second shell component greatly reduces the shell permeability which improves the capsule impermeability in surfactant-based matrices, as determined by the shell Permeability Test; (described thereafter).

In the present invention, capsules may be formed by first admixing a hydrophobic material with an inorganic precursor of formula (I), described later, where M is preferably silicon. Said precursor/oil mixture is then either used as a dispersed phase or as a continuous phase in conjunction with a water phase, where in the former case an O/W emulsion is formed and in the latter a W/O emulsion is formed once the two phases are mixed and homogenized via methods that are known to the person skilled in the art.

In the instance where M is silicon in the inorganic precursor of formula (I), the silica precursor will start undergoing a hydrolysis reaction with water at the Oil/Water interface to form a partially hydrolyzed precursor with silanol group(s). Said partially hydrolyzed precursor is then able to either react with another hydrolyzed precursor to form a siloxane bond, releasing a water molecule or react with an unhydrolyzed precursor to form also a siloxane bond, releasing an alcohol molecule. The silica precursor can also undergo additional hydrolysis before reacting with another specie. In addition, the silica precursor can react with nanoparticles located at the Oil/Water interface, by a similar mechanism involving either an alcohol or a water releasing condensation reaction, depending on the state of hydrolysis of said precursor. All of the above processes serve to anchor the silica precursor at the Oil/Water interface.

The inorganic precursor of formula (I) is characterized by multiple physical properties, namely a molecular weight (Mw), a degree of branching (DB) and a polydispersity index (PDI) of the molecular weight distribution. It has been found that Mw and DB are important to obtain capsules that hold their mechanical integrity once left drying on a surface and that have low shell permeability in surfactant-based matrices.

Without wishing to be bound by theory, it is believed that by anchoring inorganic precursors of formula (I) to the interface so neatly, a low water environment is provided, which has structural impacts on the resulting shell. Such a low water environment will lead to a considerably slower reaction time than if monomeric precursors or low Mw oligomers were used, due to a limited contact between the reacting species (i.e. water and precursor). In this invention we have overcome these drawbacks by carefully selecting both the type of precursor used and nanoparticles, leading to the formation of a dense capsule shell. Without being limited to theory it is believed that upon hydrolysis, inorganic precursors with a low Mw are not interfacially active enough to start forming the first shell component, and thus a large fraction disperses into the aqueous phase, reducing the final yield of the shell formation. Once a shell has started to form, inorganic precursors with a low Mw can still diffuse through the forming shell further reducing the desired yield of the shell. In addition, inorganic precursors with a too small degree of branching have fractal dimensions such that they would be mutually transparent towards each other (Applied Catalysis A, vol 96, pp 103, 1993), meaning that two precursors with low Mw and low DB are less likely to react with each other to form a solid shell, either leaving voids in the shell or resulting in loss of the precursors to the aqueous phase. If a higher concentration of inorganic precursor is used to compensate such loss, the water phase will contain too much inorganic precursor and eventually the whole system will gel. Finally, inorganic precursors immersed in excess water (i.e. dispersed in water) tend to react faster, and lead to fast growth of ever larger polymers and particles. As has been explained above, larger polymers and particles have limited interpenetration into an existing network and therefore would not increase the yield of the shell or at the very least not provide a dense enough shell.

Therefore, to obtain capsules according to the present invention, capsules having a dense and strong shell characterized by low shell permeability in surfactant based matrices and the ability for mechanical self-integrity, precursors having a degree of branching above 0.19, preferably above 0.2 and a molecular weight above 600 Da, preferably above 700 Da, preferably above 1000 Da are necessary.

In certain embodiments, a mixture of precursors comprising a precursor of formula (I) and TBOS can also be used to obtain capsules that provide low shell permeability in surfactant-based matrices and good mechanical properties. It has been found, that when used together with a precursor of formula (I), the permeability is reduced versus using only a precursor of formula (I). This effect is more pronounced for higher molecular weight precursors.

Without being bound by theory, it is believed that the use of TBOS reduces the porosity of the capsule shell, thus leading to a denser shell network. It is known from art that the greater the size of the alkoxy chain bound to the Silicon atom, the slower the hydrolysis reaction is. Therefore, it is believed that when the precursor of formula (I) bearing alkoxy moieties that are shorter than the butoxy of TBOS, the former starts to react first and forms an initial shell. TBOS will start hydrolyzing at a later stage and will subsequently react in the only locations where water can still be found, that is the pores of the shell, thus ensuring that the overall permeability of the shell is greatly reduced and leading to lower capsule permeability.

A second shell component has a primary role of reducing shell permeability. A second shell component can also greatly improve capsule mechanical properties, such as a capsule rupture force and fracture strength. Without intending to be bound by theory, it is believed that a second shell component contributes to the densification of the overall shell by depositing a precursor in pores remaining in the first shell component. A second shell component also adds an extra inorganic layer onto the surface of the capsule.

The second shell component comprises inorganic material chosen from the list of $SiO_2$, $TiO_2$, $Al_2O_3$, $ZrO_2$, $ZnO_2$, $CaCO_3$, $Ca_2SiO_4$, $Fe_2O_3$, $Fe_3O_4$, clay, gold, silver, iron, nickel, and copper, preferably chosen from $SiO_2$. In other embodiments, the preferred component is calcium carbonate. Preferably, the second shell component material is of the same type of chemistry as the first shell component in order to maximize chemical compatibility. Second shell components made from organic materials are known in existing art but differ from the inorganic second shell components of the present invention, in that second shell components made from organic materials generally do not provide low permeability capsule shells or mechanically improved capsules.

Improved capsule mechanical properties provided by use of a second shell component, as disclosed in this invention, can only be achieved in combinations with unique first shell components. Capsules made from tetraethoxysilane (TEOS) and commercial polyethoxysilanes (e.g. Evonik Dynasylan 40), for example, do not provide satisfactory mechanical properties when further combined with inorganic second shell components. It is the unique combination of the first shell and second shell components, as disclosed in this invention, that provides both low shell permeability in surfactant-based matrices and mechanical robustness.

Without desiring to be bound by theory, it is believed that the second shell component, as disclosed in the present invention has the unique property of depositing into the first shell component micropores and covers most of the final capsule surface, thus providing an improved mechanical robustness of the capsule. Filling of the micropores reduces the formation of microcracks when the capsule is under stress by high agitation and upon shell drying. A common solution to the formation of capsule shell microcracks can be the use of labile spacers in the capsule shell network, but this requires the introduction of organic materials, and these generally greatly increase the shell permeability in surfactant-based matrices, such as laundry detergents In embodiments, the first shell component can include a condensed layer and a nanoparticle layer, wherein the condensed layer is disposed between the core and the nanoparticle layer. In embodiments, the first shell component can include a metal oxide and/or a semi-metal oxide. In embodiments, the first shell component can include metal, mineral, metal-oxide, and/or semi-metal oxide nanoparticles. In embodiments the nanoparticles can be one or more of $SiO_2$, $TiO_2$, $Al_2O_3$, $ZrO_2$, $ZnO_2$, $Fe_2O_3$, $Fe_3O_4$, $CaCO_3$, clay, silver, gold, and copper. The condensed layer and the nanoparticle layer when both present can have the same or different materials. In embodiments, the first shell component is entirely or substantially entirely $SiO_2$.

In embodiments, the first shell component is entirely inorganic. In embodiments, the first shell component can include up to 5% by weight of the first shell component organic material. For example, the organic material can be present in the precursor and/or the nanoparticles and/or added as a separate component. In embodiments, the organic material can be present from unreacted monomers or byproducts of the polymerization. In embodiments, the nanoparticles can include a surface modification containing organic materials. In embodiments, organic material can be added to the first shell component.

In embodiments, the capsule can further include a second shell component wherein the second shell component surrounds the first shell component. In embodiments, the second shell component includes one or more of a metal oxide, a semi-metal oxide, a mineral and a metal. In embodiments the second shell component can include one or more of $SiO_2$, $TiO_2$, $Al_2O_3$, $ZrO_2$, $ZnO_2$, $CaCO_3$, $Ca_2SiO_4$, $Fe_2O_3$, $Fe_3O_4$, clay, gold, silver, iron, nickel, and copper. In embodiments, the second shell component is entirely or substantially entirely $SiO_2$.

In embodiments, the shell only includes the first shell component. In other embodiments, the shell includes both the first and the second shell component. In embodiments, the first shell component and the second shell component are entirely or substantially entirely $SiO_2$. It is also contemplated herein that the shell can include additional shell components. In various embodiments, the core can be an oil-based core. In other embodiments, the core can be a water-based core.

Capsules of the present invention comprise certain physical parameters, such as shell thickness and capsule diameter. The combination and presence of the unique constraints on capsule size, shell thickness and effective core/shell ratio leading to the low permeability of the shell is the corner stone of this invention. Not only are each of these values individually important, but also their ratio (i.e. core/shell ratio). For example, shells that are too thin compared to the overall size of the capsule tend suffer from a lack of self-integrity and collapse once deposited and dried on a surface. On the other hand, shells that are extremely thick as compared to the diameter of the capsule tend to have increased shell permeability in a surfactant-based matrix. While it may be thought that a thick shell leads to low shell permeability (since this parameter impacts the overall diffusion pathway across the shell), it has surprisingly been found that capsules having a shell with a thickness above a certain threshold have higher shell permeability. This discovery is in contrast to what is known in the prior art wherein it is believed increased shell thickness provides low shell permeability; the capsules of the present invention demonstrate the teachings of the prior art do not always apply in regard to shell thickness and shell permeability.

Without being bound by theory, it is believed that in order to increase the shell thickness of the capsules, two options present themselves: First option, for the same amount of precursor, trying to obtain a thicker shell could lead to a porous shell, and therefore result in a capsule having a low shell permeability in a surfactant-based matrix; Second option, increasing the amount of precursor in the core prior to the emulsification step. In this second scenario, the thickness of the first shell component will increase as the reaction is progressing. However, at a certain point the shell becomes so dense due to the advancement of the reaction that the remaining precursors are unable to enter into contact with the water phase to hydrolyze, hence limiting further the increase of shell thickness. This thickness is an upper threshold. Therefore, capsules with thick first shell components are obtained with a porous shell that is not dense enough to stop further reaction with external water from happening. It has been found that the capsules of this invention cannot increase the thickness of the first shell component above said upper threshold without it also being permeable. However, the upper thickness threshold increases as the capsule diameter increases.

For capsules containing a core material to perform and be cost effective in consumer good applications, such as liquid detergent or liquid fabric softener, they should: i) be resistant to core diffusion during the shelf life of the liquid product; ii) have ability to deposit on the targeted surface during application (e.g. washing machine cycle) and iii) be able to release the core material by mechanical shell rupture at the right time and place to provide the intended benefit for the end consumer.

The size of a capsule is known to have a critical impact on the efficiency of capture and deposition of capsules on targeted substrates, such as fabrics or hairs. A certain minimum capsule size is needed maximize their capture when passing through a fabric fiber mesh or hair bundles. When capsules are too large however, they are noticeable either by an unpleasant grainy feel or simply by the naked eye.

Shell thickness is usually selected as a compromise between providing low shell permeability and mechanical strength. Indeed, thin shells can lead to somewhat poor barrier properties against the diffusion of small volatile molecules through the capsule shell, such as perfume raw materials. However, thick shells provide good barrier properties but at the expense of lower payload of core-materials, drastically increasing the encapsulation cost to deliver a certain amount of core material compared to a thinner shell. This is particularly a problem for inorganic shells obtained by sol-gel precursors, as those experience a drastic weight loss during the hydrolysis reaction. For instance, shells obtained from a tetraethoxysilane (TEOS) precursor directly or via a polyalkoxysilane (PAOS) oligomer as an intermediate reactant, will lose 72% of initial TEOS weight by the hydrolysis of hydrolysable ethoxy moieties. To overcome these inherent weight losses, one would have to increase the amount of precursor by more than 3 times to achieve a target shell thickness, unavoidably increasing the cost of required raw material.

The mechanism of the shell formation of the present invention can be described as "brick and mortar". More specifically, the first shell component composed of high molecular weight polyalkoxysilane (PAOS) compound and, optionally of nanoparticles, act as the "bricks", providing structural integrity and mechanical resistance of the capsule shell. The second shell component composed of a low molecular weight compound will diffuse within the interstitial space between the bricks, acting as mortar to further increase the mechanical strength of the shell and drastically reduce the shell permeability.

In embodiments, the capsule shells advantageously have low permeability, which advantageously allows for slow diffusion of the encapsulated benefit agent when incorporated into a formulated product. In embodiments, capsules can have improved storage stability, for example, demonstrating reduced shell permeability and slow diffusion of the encapsulated benefit agent over storage time. Without intending to be bound by theory, it is believed that capsule shells in accordance with embodiments of the disclosure have low porosity and high density, thereby enhancing the stability of the capsules as compared to conventional inorganic capsules. Further, without intending to be bound by theory, it is believed that the improved shell architecture allows for targeted fracture strengths to be achieved allowing ultimate fracture at the targeted pressure during use. That is, despite increased density and structural stability, the capsules remain capable of performing as intended and fracturing at the desired and intended pressures during use.

Permeability as measured by the Permeability Test Method described below correlates to the porosity of the capsule shells. In embodiments, the capsules or populations of capsules have a permeability as measured by the Permeability Test Method of about 0.01% to about 80%, about 0.01% to about 70%, about 0.01% to about 60%, about 0.01% to about 50%, or about 0.01% to about 40%, about 0.01% to about 30%, or about 0.01% to about 20%. For example, the permeability can be about 0.01, 0.1, 0.5, 1, 2, 3, 4, 5, 6, 7, 8, 9, 10, 11, 12, 13, 14, 15, 20, 25, 30, 35, 40, 45, 50, 55, 60, 65, 70, 75, or 80%.

In accordance with embodiments, the capsules or population of capsules can have a mean volume weighted capsule diameter of at least 10 micrometers, a mean shell thickness of at least 170 nm, and a coefficient of variation of capsules diameter of less than or equal to 40%. In embodiments the capsules have a liquid core at room temperature.

In variations of the embodiments described herein, the capsules can have a mean shell thickness of about 10 nm to about 10,000 nm, about 10 nm to about 1000 nm, about 170 nm to 10,000 nm, about 170 nm to about 1000 nm, about 300 nm to about 1000 nm. In embodiments, the shell can have a thickness of about 50 nm to about 1000 nm, about 10 nm to about 200 nm, about 100 nm to about 1000 nm, about 200 nm to about 1000 nm, about 300 nm to about 1000 nm, about 300 nm to about 800 nm, about 300 to about 700 nm, about 300 nm to about 500 nm, or about 300 nm to about 400 nm. For example, the shell thickness can be about 10, 20, 30, 40, 50, 60, 70, 80, 90100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 2000, 3000, 4000, 5000, 6000, 7000, 8000, 9000, or 10,000 nm.

In various embodiments described herein, the capsules can have a mean volume weighted capsule diameter of about 0.1 micrometers to about 300 micrometers, about 0.1 micrometers to about 100 micrometers, about 10 micrometers to about 200 micrometers, about 10 micrometers to about 100 micrometers, about 10 micrometers to about 75 micrometers, about 50 micrometers to about 100 micrometers, or about 10 micrometers to about 50 micrometers. Other suitable mean volume weighted capsule diameter of about 0.1, 0.5, 1, 5, 10, 15, 20, 25, 30, 35, 40, 45, 50, 55, 60, 65, 70, 75, 80, 85, 90, 95, 100, 125, 150, 175, 200, 225, 250, 275, or 300 micrometers.

In various embodiments, a population of capsules having a large mean diameter can be provided. For example, in various embodiments capsules having a mean diameter of 10 μm or greater or 12 μm or greater can be provided. In various embodiments, a population of capsules can have a mean diameter of the capsules of the population greater than 10 μm. In various embodiments, a population of capsules having 60%, 70%, 80%, 90%, and up to 100% of the capsules having a diameter of greater than 10 μm can be provided. Large capsule diameters can be advantageous to contain more benefit agent, thereby allowing for increased concentration of benefit agent in a formulated product without requiring a significant concentration of capsules. It has been advantageously found that large capsules can be provided in accordance with embodiments herein without sacrificing the stability of the capsules as a whole and/or while maintaining good fracture strength.

In embodiments, the capsules can have a value of mean shell thickness divided by mean diameter of greater than about 0.1%. In embodiments, the capsules can have a value of mean shell thickness divided by mean diameter of greater than about 0.2%, or greater than about 0.5%, or greater than about 1%. For example, the capsules can have a value of mean shell thickness divided by mean diameter of greater than about 0.2% to about 10%, or 0.2% to about 9%, or about 0.2% to about 7.8%, or about 0.2% to about 6%, or about 0.2% to about 5.6%, or about 0.5% to about 5.6%.

It has surprisingly been found that in addition to the inorganic shell the volumetric core-shell ratio plays an important role to ensure the physical integrity of the capsules. Shells that are too thin vs. the overall size of the capsule (core:shell ratio >98:02) tend to suffer from a lack of self-integrity and collapse once deposited and dried on a surface. On the other hand, shells that are extremely thick vs. the diameter of the capsule (core:shell ratio <80:20) tend to have higher shell permeability in a surfactant-rich matrix. While one might intuitively think that a thick shell leads to lower shell permeability (since this parameter impacts the mean diffusion path of the active across the shell), it has surprisingly been found that the capsules of this invention that have a shell with a thickness above a threshold have higher shell permeability. This upper threshold is dependent on the capsule diameter.

An effective and inventive core:shell ratio is obtained by selecting the composition of shell precursor to core material. When the core:shell ratio is too low, the large amount of first shell material often leads to gelling the core, which negatively impacts the migration of shell material at the oil/water interface by disrupting the brick and mortar mechanism. When the core-shell ratio is too large, mechanical strength provided by the thin shell is not enough to sustain the core weight upon drying on substrates.

In embodiments, the capsules can have a mean effective volumetric core-shell ratio of about 60:40 to about 99:1, about 70:30 to about 99:1, about 80:20 to about 99:1, 60:40 to about 98:2, about 70:30 to about 98:2, about 80:20 to about 98:2, about 70:30 to about 96:4, about 80:20 to about 96:4, about 90:10 to about 96:4. For example, the mean effective volumetric core-shell ratio can be about 60:40, 65:35, 70:30, 75:25, 80:20, 85:15, 90:10, 95:5, 98:2, or 99:1 and any combinations thereof.

In embodiments, the capsules can have a mean effective volumetric core-shell ratio of about 99:1 to about 50:50, a have a mean volume weighted capsule diameter of about 0.1 μm to about 200 μm, and a mean shell thickness of about 10 nm to about 10,000 nm. In embodiments, the capsules can have a mean effective volumetric core-shell ratio of about 99:1 to about 50:50, a have a mean volume weighted capsule diameter of about 10 μm to about 200 μm, and a mean shell thickness of about 170 nm to about 10,000 nm. In embodiments, the capsules can have a mean effective volumetric core-shell ratio of about 98:2 to about 70:30, a have a mean volume weighted capsule diameter of about 10 μm to about 100 μm, and a mean shell thickness of about 300 nm to about 1000 nm.

In embodiments, the capsules can have a weight core-shell ratio of about 60 to 40 to about 99 to 1, about 70 to 30, about 80 to 20, about 70 to 30 to about 96 to 4, about 80 to 20 to about 96 to 4, about 90 to 10 to about 96 to 4. For example, the weight core-shell ratio can be about 60:40, 65:35, 70:30, 75:25, 80:20, 85:15, 90:10, 95:5, 98:2, or 99:1.

In embodiments, methods in accordance with embodiments of the disclosure can produce capsule having a low coefficient of variation of capsule diameter. In embodiments, a population of capsules can have a coefficient of variation of capsule diameter of 50% or less, 40% or less, 30% or less, or 20% or less. For example, the coefficient of variation of capsule diameter can be less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50%. Control over the distribution of size of the capsules can beneficially allow for the population to have improved and more uniform fracture strength. Additionally, in embodiments, the fracture strength can be tailored more effectively with variation of parameters such as shell thickness, core material, because the effect of capsule size is limited over the population by virtue of the narrow distribution of size.

In embodiments, the capsules herein can have an average fracture strength of at least 0.1 MPa, or at least 0.25 MPa, or about 0.1 MPa to about 10 MPa, or about 0.25 MPa to about 10 MPa, or about 0.1 MPa to about 5 MPa, or about 0.25 MPa to about 5 MPa, or about 0.1 MPa to about 3 MPa, or about 0.25 MPa to about 3 MPa. For example, the average fracture strength can be about 0.1 MPa, 0.2 MPa, 0.25 MPa, 0.3 MPa, 0.4 MPa, 0.5 MPa, 0.6 MPa, 0.7 MPa, 0.8 MPa, 0.9 MPa, 1 MPa, 1.1 MPa, 1.2 MPa, 1.3 MPa, 1.4 MPa, 1.5 MPa, 1.6 MPa, 1.7 MPa, 1.8 MPa, 1.9 MPa, 2 MPa, 3 MPa, 4 MPa, or 5 MPa. Fully inorganic capsules, such as certain embodiments herein, have traditionally had poor fracture strength, whereas herein, the fracture strength of the capsules can be greater than 0.25 MPa providing for improved stability and a triggered release of the benefit agent upon a designated amount of rupture stress.

In various embodiments, the capsules can have their mechanical properties defined in terms of a parameter of nominal wall tension, which is tension or stretch of capsule wall at rupture. Nominal wall tension values are independent of capsules size (Wang et al., "Modelling the mechanical properties of single suspension-cultured tomato cells", *Annals of Botany*, vol. 93, no. 4, pp. 443-453, 2004). Due to such unique characteristics, nominal wall tension can be used to compare the mechanical properties of capsules across different mean sizes. The nominal wall tension, $T_R$, is calculated using the method described in "Liu, M. (2010). *Understanding the mechanical strength of microcapsules and their adhesion on fabric surfaces*. Birmingham, United Kingdom: University of Birmingham (Doctoral thesis)".

In accordance with embodiments, capsules can have an average nominal wall tension of at least 0.1 N/m, or at least 0.25 N/m, or about 0.1 N/m to about 20 N/m, or about 0.25 N/m to about 20 N/m, or about 0.5 N/m to about 20 N/m, or about 0.5 N/m to about 15 N/m, or about 1 N/m to about 15 N/m. For example, the average nominal wall tension can be about 0.1 N/m, 0.2 N/m, 0.3 N/m, 0.4 N/m, 0.5 N/m, 0.6 N/m, 0.7 N/m, 0.8 N/m, 0.9 N/m, 1 N/m, 1.1 N/m, 1.2 N/m, 1.3 N/m, 1.4 N/m, 1.5 N/m, 1.6 N/m, 1.7 N/m, 1.8 N/m, 1.9 N/m, 2 N/m, 3 N/m, 4 N/m, 5 N/m, 6 N/m, 7 N/m, 8 N/m, 9 N/m, 10 N/m, 11 N/m, 12 N/m, 13 N/m, 14 N/m, or 15 N/m.

In accordance with embodiments, capsules can be made by employing a Pickering emulsifier.

The capsules of the present invention comprise a shell surrounding a core, wherein the shell comprises a first shell component and optionally a second shell component. In some embodiments, the first shell component comprises nanoparticles, which are preferably of the same chemistry type as the first shell component formed by the hydrolysis and condensation reaction of the precursors of formula (I).

While it is possible to make capsules of the present invention without the use of nanoparticles due to the good interfacial activity of the precursor of formula (I), the use of nanoparticles impacts the shell formation mechanism in a way that leads to a more compact layer of condensed precursors of formula (I), for reasons detailed below.

In embodiments, the method of making oil-based core containing capsules can include the use of hydrophilic nanoparticles as Pickering emulsifiers. According to the literature (Langmuir 2013, 29, 49, 15457-15462) the use of nanoparticles that do not strongly adhere to the emulsion interface (in this case hydrophilic nanoparticles) can provide a fine-tuned emulsion process, in which the detachment energy needed to remove the nanoparticles from the interface is minimal. Without intending to be bound by theory, it is believed that this allows for the formation of a thicker condensed layer, and the nanoparticles move from the water-oil interface to the water-hydrolyzed precursor interface (FIG. 1A), the water-hydrolyzed precursor interface is more thermodynamically favorable as the precursor starts to hydrolyze and becomes less hydrophobic. The hydrophilic nanoparticles preferentially adhere onto the newly formed water-hydrophilic precursor interface. The hydrolyzed precursor then condensates forming a solid first shell component.

In embodiments, capsules having an oil-based core can be made by admixing an oil phase with an aqueous phase and emulsifying the admixture under conditions sufficient to disperse droplets of oil phase in aqueous phase. The oil phase can include an oil-based core modifier and/or oil-soluble benefit agent and a precursor. The aqueous phase can include water and nanoparticles. The aqueous phase can further include an acid in embodiments. Upon emulsification, the nanoparticles from the aqueous phase self-assemble around the oil droplets and interpose at the interface between the continuous aqueous phase and the dispersed oil phase, thereby stabilizing the emulsion and defining the nanoparticle layer. Further, the precursor present in the oil droplets undergoes hydrolysis and condensation at the interface between the continuous water phase and the dispersed oil phase between the nanoparticle layer and the oil droplet. The method then further includes curing the emulsions under conditions to further solidify the hydrolyzed and condensed precursor to thereby form a condensed layer. The nanoparticle layer and the condensed layer thereby form the first shell component of the shell. Without intending to be bound by theory, it is believed that covalent bonds are formed between the condensed precursor and the nanoparticles.

In embodiments, capsules having an aqueous-based core can be made by admixing an aqueous phase with an oil phase and emulsifying the admixture under conditions sufficient to disperse droplets of aqueous phase in oil phase. The aqueous phase can include an aqueous-based and/or aqueous-soluble benefit agent. The oil phase can include a precursor. One or both of the aqueous phase and the oil phase can include nanoparticles. Upon emulsification, the nanoparticles self-assemble around the aqueous droplets and interpose at the interface between the dispersed aqueous phase and the continuous oil phase, thereby defining the nanoparticle layer. Further, the precursor present in the continuous oil phase undergoes hydrolysis and condensates at the interface between the continuous oil phase and the dispersed aqueous phase. The method then further includes curing the emulsions under conditions to solidify the hydrolyzed and condensed precursor to thereby form a condensed layer. The nanoparticle layer and the condensed layer thereby form the first shell component of the shell. Without intending to be bound by theory, it is believed that covalent bonds are formed between the condensed precursor and the nanoparticles.

In embodiments, the method, whether including a water-based core or an oil-based core, can further include forming the second shell component surrounding the first shell component by admixing the capsules with a solution having second shell component precursors under conditions sufficient to form a second shell component on top of and intimately connected to the capsule first shell component. The solution having second shell component precursors can include a water soluble or oil soluble precursor. As described above, the second shell component can be inorganic.

In embodiments, the method can further include washing and drying the capsules after the process of forming the second shell component, using any suitable methods. For example, centrifugation can be used in a washing step. Drying methods are known in the art. One example of drying can be spray drying.

In embodiments, the method of making oil-based core containing capsules can include the use of hydrophilic nanoparticles as Pickering emulsifiers. Without intending to be bound by theory, it is believed that the use of hydrophilic nanoparticles can provide a fine tuned emulsion process, in which, the nanoparticles are not strongly adhered to the emulsion interface, so the detachment energy to remove the nanoparticles from the interface is low. Without intending to be bound by theory, it is believed that this allows for the formation of a thicker condensed layer, and the nanoparticles move from the water-oil interface, to the water-precursor interface (FIG. 1A), the second interface is more thermodynamically favorable as the precursor starts to hydrolyze and becomes less hydrophobic. The hydrophilic nanoparticles preferentially adhere onto the newly formed water-hydrophilic precursor interface. The hydrolyzed precursor then condensates forming a solid first shell component.

In embodiments, the result of the methods herein is a slurry containing the capsules. In embodiments, the slurry can be formulated into a product, such as a consumer product. The formulated product can include in addition to the slurry one or more processing aids. In embodiments, the processing aids can include one or more of water, aggregate inhibiting materials such as divalent salts, and particle suspending polymers. In embodiments, the aggregate inhibiting materials can include salts that can have a charge-shielding effect around the capsule, such as magnesium chloride, calcium chloride, magnesium bromide, and magnesium sulfate. In embodiments, formulated product can further include one or more of xanthan gum, carrageenan gum, guar gum, shellac, alginates, chitosan; cellulosic materials such as carboxymethyl cellulose, hydroxypropyl methyl cellulose, cationic cellulosic materials; polyacrylic acid; polyvinyl alcohol; hydrogenated castor oil; and ethylene glycol distearate. In embodiments, the formulated product can include one or more carriers. In embodiments, the carriers can be one or more polar solvents, including but not limited to, water, ethylene glycol, propylene glycol, polyethylene glycol, and glycerol; and nonpolar solvents, including but not limited to, mineral oil, perfume raw materials, silicone oils, and hydrocarbon paraffin oils. In embodiments, the formulated product can include one or more of silica, citric acid, sodium carbonate, sodium sulfate, sodium chloride, and binders such as sodium silicates, modified celluloses, polyethylene glycols, polyacrylates, polyacrylic acids, and zeolites.

Capsules of the present invention can be formed from polyalkoxysilane (PAOS) or polyalkoxysilanes bearing non-hydrolysable moieties. Those later PAOS yield capsules with residual organic moieties in the shell. It has been found that capsules with residual organic moieties in the shell present a significantly higher shell permeability compared to capsules without residual organic moieties. The addition of a second shell component formation step reduces the shell permeability of capsules, thereby allowing a certain quantity of organic moieties into the first shell component without increasing too much shell permeability. The primary purpose of PAOS is to produce capsules that do not collapse and have good mechanical properties, while also providing a low shell permeability. Further, comparative testing, as shown below, demonstrates shell permeability is reduced when capsules are produced using PAOS and not organo-silanes.

In some embodiments, the capsules comprise only the first shell component comprising a condensation product of a precursor of formula (I). These capsules can provide the same or similar benefits as those of the present invention comprising a first and second shell component that is low shell permeability in a surfactant-based matrix and the ability to hold their integrity when left drying on a surface. However, the shell permeability is greatly reduced when both first and second shell components are included, which is a preferred embodiment of this invention.

In certain embodiments, capsules comprise a first shell component comprising condensation products of formula (II) precursors (i.e. organosilanes), or mixtures of formula (I) or (II) and monomers bearing one, two, or three carbon silicon bonds.

In addition, when capsules include both a first shell component comprising the condensation product of a precursor of formula (II) or a mixture of a precursor of formula (I) or (II) and monomers bearing one, two or three carbon silicon bonds, and a second shell component, the shell permeability in a surfactant-based matrix is greatly reduced when compared to the same capsules lacking a second shell component.

Therefore, whilst capsules comprising a first shell component and a second shell component, where the first shell component comprises condensation products of a precursor of Formula (I), are a preferred embodiment, it has been found that the first shell component can tolerate a fraction of condensation products of a precursor of formula (II), or a mixture of precursors of formula (I) or (II), and monomers bearing one, two or three silicon carbon bonds, without complete loss of permeability resistance in a surfactant based matrix in the resultant capsules.

The fraction of condensation products of a precursor of formula (II) is defined as leading to a total first shell composition comprising less than 10 wt %, preferably less than 9 wt %, preferably less than 8 wt %, preferably less than 7 wt %, preferably less than 6 wt %, preferably less than 5 wt %, preferably less than 4 wt %, preferably less than 3 wt %, preferably less than 2 wt % preferably less than 1 wt % of organic content, as defined in the organic content calculation section.

Without desiring to be bound by theory, it is believed that the organic compounds can act as spacers within the shell thus reducing the crosslink density of the first shell component, which in too large of quantities can provide substantial porosity. First shell components that have a sufficiently low level of organic compounds therefore can result in higher shell permeability in surfactant-based matrices while still containing enough capability towards self-integrity when drying on a surface.

As defined earlier, whilst the first shell components can be used as a scaffold or skeleton for the capsule in order to provide mechanical resistance, while still supplying reduced shell permeability in a surfactant-based matrix in certain embodiments, the inclusion of a second shell component greatly reduces the shell permeability in a surfactant-based matrix. In embodiments, the precursor includes at least one compound of formula (I) and/or at least one compound of formula (II) in combination with one or more of tetraethoxysilane (TEOS), tetramethoxysilane (TMOS), tetrabutoxysilane (TBOS), triethoxymethylsilane (TEMS), diethoxy-dimethylsilane (DEDMS), trimethylethoxysilane (TMES), and tetraacetoxysilane (TAcS).

In embodiments, emulsifying the dispersed phase and continuous phase can include one or more of a high shear homogenization process, a microfluidization process, and an ultrasonication process. In embodiments, the emulsification of the dispersed phase and continuous phase can include a high shear homogenization process. In embodiments, the high shear homogenization process can include one or more mixers, such as an ultraturrax mixer or a vortex mixer. In embodiments, the mixer can have a speed of 100 rpm to 20,000 rpm, or 500 rpm to 15,000 rpm, or 1000 rpm to 10,000 rpm, or 2000 rpm to 10,000 rpm. For example, the mixer can have a speed of 1000 rpm, 1500 rpm, 2000 rpm, 2500 rpm, 3000 rpm, 3500 rpm, 4000 rpm, 4500 rpm, 5000 rpm, 6000 rpm, 7000 rpm, 8000 rpm, 9000 rpm, or 10,000 rpm.

In embodiments, the dispersed phase and the continuous phase can be emulsified for about 1 minute to about 2 hours, or about 1 minute to about 30 minutes, or about 1 minute to about 10 minutes. For example, the emulsification can be 1 minute, 2 minutes, 3 minutes, 4 minutes, 5 minutes, 6 minutes, 7 minutes, 8 minutes, 9 minutes or 10 minutes.

In embodiments, the emulsion can be formed substantially free of surfactant. In embodiments, the emulsion being "substantially free" of surfactant includes surfactant in an amount of 0.001% w/w or less.

In embodiments, a curing process can be used to solidify the shell. In embodiments, the curing process can induce condensation of the precursor. In embodiments, the curing process can be done at room temperature or above room temperature. In embodiments, the curing process can be done at temperatures above 30° C. For example, the curing process can be done at 30° C. to 150° C., 40° C. to 120° C., 50° C. to 100° C., 60° C. to 100° C., 70° C. to 100° C., or 30° C., 40° C., 50° C., 60° C., 70° C., 75° C., 80° C., 90° C., 100° C., 110° C., 120° C., 130° C., 140° C., or 150° C.

In embodiments, the curing process can be done over any suitable period of time to enable the capsule shell to be strengthened via condensation of the precursor material. In embodiments, the curing process can be done over a period of time from 1 minute to 45 days, or 1 minute to 10 days, or 1 minute to 5 days, or 1 minute to 24 hours. For example, the curing process can be done over, 1 minute, 1 hour, 2 hours, 3 hours, 4 hours, 5 hours, 6 hours, 12 hours, 24 hours, 48 hours, 72 hours, 96 hours, 5 days, 6 days, 7 days, 8 days, 9 days, 10 days, 15 days, 20 days, 21 days, 25 days, 30 days, 35, days 40 days, or 45 days. Longer cure times can also be contemplated in the methods described herein.

First Shell Component

In embodiments, the first shell component can include a condensed layer. The condensed layer can be the condensation product of one or more precursors. The one or more precursors can be of formula (I):

$$(M_vO_zY_n)_w \qquad \text{(Formula I),}$$

where M is one or more of silicon, titanium and aluminum, v is the valence number of M and is 3 or 4, z is from 0.5 to 1.6, preferably 0.5 to 1.5, each Y is independently selected from —OH, —OR$^2$,

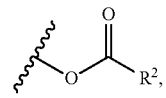

—NH$_2$, —NHR$^2$, —N(R$^2$)$_2$,

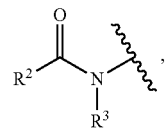

wherein $R^2$ is a $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, $R^3$ is a H, $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, n is from 0.7 to (v-1), and w is from 2 to 2000.

In embodiments, the one or more precursors can be of Formula (I) where M is silicon. In embodiments, Y is —$OR^2$. In embodiments, n is 1 to 3. In embodiments, Y is —$OR_2$ and n is 1 to 3. In embodiments, n is at least 2, one or more of Y is —$OR_2$ and one or more of Y is —OH. In embodiments, one or more of Y is

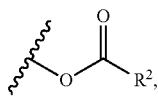

In embodiments, $R^2$ is $C_1$ to $C_{20}$ alkyl. In embodiments, $R^2$ is $C_6$ to $C_{22}$ aryl. In embodiments, $R^2$ is one or more of $C_1$ alkyl, $C_2$ alkyl, $C_3$ alkyl, $C_4$ alkyl, $C_5$ alkyl, $C_6$ alkyl, $C_7$ alkyl, and $C_8$ alkyl.

In embodiments, $R^2$ is $C_1$ alkyl. In embodiments, $R^2$ is $C_2$ alkyl. In embodiments, $R^2$ is $C_3$ alkyl. In embodiments, $R^2$ is $C_4$ alkyl.

In embodiments, z is from 0.5 to 1.3, or from 0.5 to 1.1, 0.5 to 0.9, or from 0.7 to 1.5, or from 0.9 to 1.3, or from 0.7 to 1.3.

In embodiments, M is silicon, v is 4, each Y is —$OR^2$, n is 2 and/or 3, and each $R^2$ is $C_2$ alkyl.

In embodiments, the precursor can include polyalkoxysilane (PAOS). In some embodiments, the precursor can include polyalkoxysilane (PAOS) synthesized via a hydrolytic process.

In embodiments, the precursor can alternatively or further include one or more of a compound of formula (II):

$$(M^vO_zY_nR^1_p)_w \quad \text{(Formula II)},$$

where M is one or more of silicon, titanium and aluminum, v is the valence number of M and is 3 or 4, z is from 0.5 to 1.6, preferably 0.5 to 1.5, each Y is independently selected from —OH, —$OR^2$,

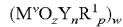

—$NH_2$, —$NHR^2$, —$N(R^2)_2$

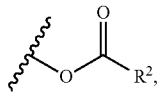

wherein $R^2$ is selected from a $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, $R^3$ is a H, $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, n is from 0 to (v-1), each $R^1$ is independently selected from a $C_1$ to $C_{30}$ alkyl, a $C_1$ to $C_{30}$ alkylene, a $C_1$ to $C_{30}$ alkyl substituted with one or more of a halogen, —$OCF_3$, —$NO_2$, —CN, —NC, —OH, —OCN, —NCO, alkoxy, epoxy, amino, mercapto, acryloyl, $CO_2H$, $CO_2$alkyl, aryl, and heteroaryl, or a $C_1$ to $C_{30}$ alkylene substituted with one or more of a halogen, —$OCF_3$, —$NO_2$, —CN, —NC, —OH, —OCN, —NCO, alkoxy, epoxy, amino, mercapto, acryloyl, $CO_2H$, $CO_2$alkyl, aryl, and heteroaryl, p is present in an amount up to pmax, and w is from 2 to 2000; wherein pmax=60/[9*Mw($R^1$)+8], where Mw($R^1$) is the molecular weight of the R group.

In embodiments, R is a $C_1$ to $C_{30}$ alkyl substituted with one to four groups independently selected from a halogen, —$OCF_3$, —$NO_2$, —CN, —NC, —OH, —OCN, —NCO, alkoxy, epoxy, amino, mercapto, acryloyl, $CO_2H$, $CO_2$alkyl, aryl, and heteroaryl. In embodiments, R is a $C_1$ to $C_{30}$ alkylene substituted with one to four groups independently selected from a halogen, —$OCF_3$, —$NO_2$, —CN, —NC, —OH, —OCN, —NCO, alkoxy, epoxy, amino, mercapto, acryloyl, $CO_2H$, $CO_2$alkyl, aryl, and heteroaryl.

In embodiments, the precursor can include at least polyalkoxysilane (PAOS). In embodiments, the precursor can further include one or both of tetraethoxysilane (TEOS), and tetrabutoxysilane (TBOS). In embodiments, the precursor can include polyalkoxysilane (PAOS) synthesized via a non-hydrolytic process. In embodiments, the precursor can include one or more of compounds of formula (I) and compounds of formula (II), alone or in combination with one or more of tetraethoxysilane (TEOS), tetramethoxysilane (TMOS), tetrabutoxysilane (TBOS), triethoxymethylsilane (TEMS), diethoxy-dimethylsilane (DEDMS), trimethylethoxysilane (TMES), and tetraacetoxysilane (TAcS). In embodiments, the precursor can also include one or more of compounds of formula (I) and formula (II), alone or in combination with one or more of silane monomers of type $Si(YR)_{4-n}R_n$ wherein YR is a hydrolysable group and R is a non-hydrolysable group. Examples of such monomers are given earlier in this paragraph, and these are not meant to be limiting the scope of monomers that can be used.

In embodiments, the compounds of formula (I) and/or the compounds of formula (II) can have a Polystyrene equivalent Weight Average Molecular Weight (Mw) of from about 100 Da to about 300,000 Da. In embodiments, the Mw can be from about 100 Da to about 100,000 Da, or from about 100 Da to about 90,000 Da, or from about 100 Da to about 80,000 Da, or from about 100 Da to about 70,000 Da, or from about 100 Da to about 60,000 about Da, or from about 200 Da to about 60,000 Da, or from about 300 Da to about 60,000 Da, or from about 400 Da to about 60,000 Da, or from about 500 Da to about 60,000 Da, or from about 600 Da to about 60,000 Da, or from about 700 Da to about 60,000 Da, or from about 700 Da to about 30,000 Da, or from about 800 Da to about 30,000 Da, or from about 900 Da to about 30,000 Da, or from about 1000 Da to about 30,000 Da, or from about 1500 Da to about 30,000 Da.

In embodiments, the compounds of formula (I) and/or formula (II) can have a molecular weight polydispersity index of about 1 to about 50. In embodiments, the molecular weight polydispersity index can be from about 1 to about 45, or about 1 to about 40, or about 1 to about 30 or about 1 to about 25, or about 1 to about 20, or about 1 to about 15, or about 1 to about 10, or about 1 to about 9, or about 1 to about 8, or about 1 to about 7, or about 1 to about 6, or about 1 to about 5, or about 1 to about 4, or about 1.4 to about 5, or about 1.5 to about 3.5. For example, the molecular weight polydispersity index can be about 1, 1.1, 1.2, 1.3, 1.4, 1.5, 1.6, 1.7, 1.8, 1.9, 2.0, 2.5, 3.0, 3.5, 4.0, 4.5, or 5.0.

In embodiments, the compounds of formula (I) and/or formula (II) can have a degree of branching of 0 to about 0.6, about 0.05 to about 0.5, about 0.01 to about 0.1, about 0.03 to about 0.13, about 0.1 to about 0.45, or about 0.2 to about 0.3. Other suitable values include about 0, 0.01, 0.02, 0.03, 0.04, 0.05, 0.06, 0.07, 0.08, 0.09, 0.1, 0.15, 0.2, 0.25 0.3, 0.35, 0.4, 0.45, 0.5, 0.55, and 0.6.

In embodiments, the first shell component can further include a nanoparticle layer. The nanoparticle of the nanoparticle layer can be one or more of $SiO_2$, $TiO_2$, $Al_2O_3$, $ZrO_2$, $ZnO_2$, $CaCO_3$, clay, silver, gold, and copper. In embodiments, the nanoparticle layer can include $SiO_2$ nanoparticles.

The nanoparticles can have an average diameter of about 1 nm to about 500 nm, about 1 nm to about 300 nm, about 1 nm to 200 nm, about 5 nm to about 100 nm, about 10 nm to about 100 nm, and about 30 nm to about 100 nm. For example, in embodiments, the nanoparticles can have an average diameter of about 1 nm, 5 nm, 10 nm, 20 nm, 30 nm, 40 nm, 50 nm, 60 nm, 70 nm, 80 nm, 90 nm, 100 nm, 150 nm, 200 nm, 250 nm, 300 nm.

In embodiments, the emulsion can advantageously be stabilized by steric hindrance provided by the nanoparticle layer surrounding the droplet and preventing coalescence. Furthermore, to form emulsions that do not coalesce, the three-phase contact angle between the nanoparticle and the immiscible phases should be close to 90°, this is due to the larger adsorption energy for nanoparticles at the oil-water interface resulting in a higher energy input required for desorption, $\Delta G_d$, according to the equation:

$$\Delta G_d = \pi r^2 \gamma ow (1-\cos\theta)^2$$

where, $\Delta G_d$ is the free energy, r the nanoparticle radius, yow the interfacial tension between the oil and water phases and $\theta$ the three-phase contact angle. The change of free energy of a spherical nanoparticle at the interface depends directly upon the water-oil interfacial tension and the radius of the nanoparticle. $\Delta G_d$ increases as a function of $r^2$, therefore, without intending to be bound by theory, usually bigger nanoparticles can stabilize emulsions more efficiently and can influence the pore size between nanoparticles.

In embodiments, the pore size can be adjusted by varying the shape of the nanoparticles and/or by using a combination of different nanoparticle sizes. In embodiments, non-spherical irregular nanoparticles can be used as they can have improved packing in forming the nanoparticle layer, which is believed to yield denser shell structures. This can be advantageous when limited permeability is required. In other embodiments, the nanoparticles used can have more regular shapes, such as spherical. Any contemplated nanoparticle shape can be used herein.

In embodiments, the nanoparticles can be substantially free of hydrophobic modifications. In embodiments, the nanoparticles can be substantially free of organic compound modifications. In other embodiments, the nanoparticles can include an organic compound modification. In embodiments, the nanoparticles can be hydrophilic.

In embodiments, the nanoparticles can include a surface modification such as but not limited to linear or branched $C_1$ to $C_{20}$ alkyl groups, surface amino groups, surface methacrylo groups, surface halogens, or surface thiols. These surface modifications are such that the nanoparticle surface can have covalently bound organic molecules on it. When it is disclosed in this document that inorganic nanoparticles are used, this is meant to include any of the aforementioned surface modifications without being explicitly called out.

Second Shell Component

In embodiments, the capsules can include a second shell component. The second shell component surrounds the first shell component. The second shell component comprises an inorganic compound. In embodiments, the second shell component can provide further stability to the capsules and decrease the permeability of the capsules. Without intending to be bound by theory, it is believed that the second shell component can further contribute to improved performance of the capsules, for example, reducing shell permeability and diffusion of the benefit agent during storage.

In embodiments, the second shell component can include one or more of a metal oxide, a semi-metal oxide, a mineral, and a metal. In embodiments, the second shell component can include one or more of $SiO_2$, $TiO_2$, $Al_2O_3$, $ZrO_2$, $ZnO_2$, $CaCO_3$, $Ca_2SiO_4$, $Fe_2O_3$, $Fe_3O_4$, clay, gold, iron, silver, nickel, and copper. In embodiments, the second shell component can be silica. In embodiments, the second shell component can be silica formed from mineralized sodium silicate.

In embodiments, the second shell component can include silica formed from mineralized sodium silicate. In embodiments, formation of a second shell component comprising silica can create a denser capsule shell due to the deposition of silica within the pores of the first shell component. FIG. 10B illustrates an embodiment of a shell having a second shell component.

In embodiments of the method, the second shell component can be formed by admixing capsules having the first shell component with a solution of second shell component precursor. The solution of second shell component precursor can include a water soluble or oil soluble second shell component precursor. In embodiments, the second shell component precursor can be one or more of a compound of formula (I) as defined above, tetraethoxysilane (TEOS), tetramethoxysilane (TMOS), tetrabutoxysilane (TBOS), triethoxymethylsilane (TEMS), diethoxy-dimethylsilane (DEDMS), trimethylethoxysilane (TMES), and tetraacetoxysilane (TAcS). In embodiments, the second shell component precursor can also include one or more of silane monomers of type $Si(YR)_{4-n}R_n$ wherein YR is a hydrolysable group and R is a non-hydrolysable group. Examples of such monomers are given earlier in this paragraph, and these are not meant to be limiting the scope of monomers that can be used. In embodiments, the second shell component precursor can include salts of silicate, titanate, aluminate, zirconate and/or zincate. In embodiments, the second shell component precursor can include carbonate and calcium salts. In embodiments, the second shell component precursor can include salts of iron, silver, copper, nickel, and/or gold. In embodiments, the second shell component precursor can include zinc, zirconium, Silicon, titanium, and/or aluminum alkoxides. In embodiments, the second shell component precursor can include one or more of silicate salt solutions such as sodium silicates, silicon tetralkoxide solutions, iron sulfate salt and iron nitrate salt, titanium alkoxides solutions, aluminum trialkoxide solutions, zinc dialkoxide solutions, zirconium alkoxide solutions, calcium salt solution, carbonate salt solution. In certain embodiments, a second shell component comprising $CaCO_3$ can be obtained from a combined use of Calcium salts and Carbonate salts. In other embodiments, a second shell component comprising $CaCO_3$ can be obtained from Calcium salts without addition of carbonate salts, via in-situ generation of carbonate ions from $CO_2$.

The second shell component precursor can include any suitable combination of any of the foregoing listed compounds.

In embodiments, the solution of second shell component precursor can be added dropwise to the capsules. In embodiments, the solution of second shell component precursor and the capsules can be mixed together for about 1 hour to about 24 hours, or about 1 hour to about 12 hours, or about 1 hour to about 5 hours. For example, the solution of second shell component precursor and the capsules can be mixed together for about 1 hour, 2 hours, 3 hours, 4 hours, or 5 hours. In embodiments, the solution of second shell component precursor and the capsules can be mixed together at room temperature or at elevated temperatures, such as 30° C. to 60° C., 40° C. to 70° C., 40° C. to 100° C. For example, the solution of second shell component precursor and the capsules can be mixed together at a temperature of room temperature, 30° C., 35° C., 40° C., 45° C., 50° C., 55° C., 60° C., 65° C., 70° C., 75° C., 80° C., 90° C., or 100° C.

In embodiments, the solution of second shell component precursor can include the second shell component precursor in an amount of about 1 wt % to about 50 wt % based on the total weight of the solution of second shell component precursor, or about 1 wt % to about 40 wt %, or about 1 wt % to about 30 wt %, or about 1 wt % to about 20 wt %, or about 5 wt % to about 20 wt %. For example, the solution of second shell component precursor can include the second shell component precursor in an amount of about 1 wt %, 5 wt %, 10 wt %, 20 wt %, 30 wt %, 40 wt %, or 50 wt % based on the total weight of the solution of second shell component precursor.

In embodiment, capsules can be admixed with the solution of second shell component precursor in the presence of an acid. In embodiments, it can be a weak acid such as HF and acetic acid. In embodiments, the acid can be a strong acid. In embodiments, the strong acid can include one or more of HCl, $HNO_3$, $H_2SO_4$, HBr, HI, $HClO_4$, and $HClO_3$. In embodiments, the acid can include HCl. In embodiments, the concentration of the acid in continuous solution can be about 0.01 M to about 5 M, or about 0.1 M to about 5 M, or about 0.1 M to about 2 M, or about 0.1 M to about 1 M. For example, the concentration of the acid in the solution of second shell component precursor can be about 0.1 M, 0.2 M, 0.3 M, 0.4 M, 0.5 M, 1 M, 1.5 M, 2 M, 3 M, 4 M, or 5 M.

In embodiments, the capsules can be admixed with a solution of second shell component precursor in the presence of a base. In embodiments, the base can be one or more of mineral bases, a hydroxide, such as sodium hydroxide, and ammonia. For example, in embodiments, the base can be about $10^{-5}$ M to 0.01M NaOH, or about $10^{-5}$ M to about 1M ammonia.

In embodiments, the process of forming a second shell component can include a change in pH during the process. For example, the process of forming a second shell component can be initiated at an acidic or neutral pH and then a base can be added during the process to increase the pH. Alternatively, the process of forming a second shell component can be initiated at a basic or neutral pH and then an acid can be added during the process to decrease the pH. Still further, the process of forming a second shell component can be initiated at an acid or neutral pH and an acid can be added during the process to further reduce the pH. Yet further the process of forming a second shell component can be initiated at a basic or neutral pH and a base can be added during the process to further increase the pH. Any suitable pH shifts can be used. Further any suitable combinations of acids and bases can be used at any time in the solution of second shell component precursor to achieve a desired pH. In embodiments, the process of forming a second shell component can include maintaining a stable pH during the process with a maximum deviation of +/−0.5 pH unit. For example, the process of forming a second shell component can be maintained at a basic, acidic or neutral pH. Alternatively, the process of forming a second shell component can be maintained at a specific pH range by controlling the pH using an acid or a base. Any suitable pH range can be used. Further any suitable combinations of acids and bases can be used at any time in the solution of second shell component precursor to keep a stable pH at a desirable range.

Core

In embodiments, the core, whether oil-based or aqueous, can include one or more benefit agents, as well as additional components such as excipients, carriers, diluents, and other agents. In embodiments, the core can be a liquid core. In embodiments, the core can be a gel core. In embodiments, the core can be aqueous and include a water-based or water-soluble benefit agent. In embodiments, the core can be oil-based and can include an oil-based or oil-soluble benefit agent. In embodiments, the core has a melting point of less than or equal to 15° C. In embodiments, the core is a liquid at the temperature at which it is utilized in a formulated product. In embodiments, the core is liquid at and around room temperature.

Oil-Based Core

An oil-based core is defined as the oil phase present in the core of a core-shell capsule, originating from the emulsification of a dispersed oil phase in a continuous aqueous phase; the aforementioned oil and aqueous phases being substantially immiscible.

In embodiments, the oil-based core, can include about 1 wt % to 100 wt % benefit agent based on the total weight of the core. In embodiments, the core can include about 25 wt % to 100 wt % benefit agent based on the total weight of the core or about 50 wt % to 100 wt % benefit agent based on the total weight of the core. For example, the core can include a benefit agent based on the total weight of the core of about 55 wt %, 60 wt %, 65 wt %, 70 wt %, 75 wt %, 80 wt %, 85 wt %, 90 wt %, 95 wt %, and 100 wt %. In embodiments, the core can include about 80 wt % to 100 wt % benefit agent based on the total weight of the core. For example, the benefit agent can be 90 wt %, 91 wt %, 92 wt %, 93 wt %, 94 wt %, 96 wt %, 97 wt %, 98 wt %, or 99 wt % of the core based on the total weight of the core.

In embodiments, the oil-soluble and/or oil based benefit agent can include one or more of chromogens and dyes, perfume composition, perfume raw materials, lubricants, silicone oils, waxes, hydrocarbons, higher fatty acids, essential oils, lipids, skin coolants, vitamins, sunscreens, antioxidants, catalysts, malodor reducing agents, odor-controlling materials, softening agents, insect and moth repelling agents, colorants, pigments, pharmaceuticals, pharmaceutical oils, adhesives, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, color maintenance agents, color restoration/rejuvenation agents, anti-fading agents, anti-abrasion agents, wear resistance agents, fabric integrity agents, anti-wear agents, anti-pilling agents, defoamers, anti-foaming agents, UV protection agents, sun fade inhibitors, anti-allergenic agents, fabric comfort agents, shrinkage resistance agents, stretch resistance agents, stretch recovery agents, skin care agents, and natural actives, dyes, phase change materials, fertilizers, nutrients, and herbicides.

In embodiments, the oil-based core can include fragrance oil.

In embodiments, the oil-based and/or oil-soluble benefit agent can include a perfume or a perfume composition. In embodiments, the perfume composition can include one or more of perfume raw materials, essential oils, malodour reducing agents, and odour controlling agents.

In various embodiments, the perfume composition can include one or more perfume raw materials. In embodiments, the perfume composition can include, by weight based on the total weight of the perfume composition, a combination of or individually (1) about 2.5% to about 30%, or about 5% to about 30%, of perfume raw materials characterized by a log P of less than 3.0 and a boiling point of less than 250° C.; (2) about 5% to about 30%, or about 7% to about 25%, of perfume raw material characterized by a log P of less than or equal to 3.0 and a boiling point greater than or equal to 250° C.; (3) about 35% to about 60%, or about 40% to about 55%, of perfume raw materials characterized by having a log P of greater than 3.0 and a boiling point of less than 250° C.; and (4) about 10% to about 45%, or about 12% to about 40%, of perfume raw materials characterized by having a log P greater than 3.0 and a boiling point greater than 250° C.

In embodiments, the benefit agent can have an average log P of greater than or equal to 1.

Water-Based Core

A water-based core is defined as the aqueous phase present in the core of a core-shell capsule, originating from the emulsification of a dispersed aqueous phase in a continuous oil phase; the aforementioned oil and aqueous phases being substantially immiscible.

In embodiments, the water-based core can include about 1 wt % to 99 wt % benefit agent based on the total weight of the core. In embodiments, the core can include about 1 wt % to 75 wt % benefit agent based on the total weight of the core or about 1 wt % to 50 wt % benefit agent based on the total weight of the core. For example, the core can include a benefit agent based on the total weight of the core of about 1 wt %, 5 wt %, 10 wt %, 15 wt %, 20 wt %, 25 wt %, 30 wt %, 35 wt %, 40 wt %, 45 wt %, and 50 wt %. In embodiments, the core can include about 1 wt % to 20 wt %, 30 wt % to 50 wt %, or 20 wt % to 40 wt %, benefit agent based on the total weight of the core.

In embodiments, the water-based and/or water soluble benefit agent is one or more of perfume compositions, perfume raw materials, perfume, skin coolants, vitamins, sunscreens, antioxidants, glycerin, bleach encapsulates, chelating agents, antistatic agents, insect and moth repelling agents, colorants, antioxidants, sanitization agents, disinfecting agents, germ control agents, mold control agents, mildew control agents, antiviral agents, drying agents, stain resistance agents, soil release agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin care agents, and natural actives, antibacterial actives, antiperspirant actives, cationic polymers, dyes, metal catalysts, non-metal catalysts, activators, pre-formed peroxy carboxylic acids, diacyl peroxides, hydrogen peroxide sources, and enzymes.

In embodiments, the water-based and/or water soluble benefit agent can include one or more metal catalysts. In embodiments, the metal catalyst can include one or more of dichloro-1,4-diethyl-1,4,8,11-tetraaazabicyclo[6.6.2]hexadecane manganese(II); and dichloro-1,4-dimethyl-1,4,8,11-tetraaazabicyclo[6.6.2]hexadecane manganese(II). In embodiments, the non-metal catalyst can include one or more of 2-[3-[(2-hexyldodecyl)oxy]-2-(sulfooxy)propyl]-3,4-dihydroisoquinolinium, inner salt; 3,4-dihydro-2-[3-[(2-pentylundecyl)oxy]-2-(sulfooxy)propyl]isoquinolinium, inner salt; 2-[3-[(2-butyldecyl)oxy]-2-(sulfooxy)propyl]-3,4-dihydroisoquinolinium, inner salt; 3,4-dihydro-2-[3-(octadecyloxy)-2-(sulfooxy)propyl]isoquinolinium, inner salt; 2-[3(hexadecyloxy)-2-(sulfooxy)propyl]-3,4-dihydroisoquinolinium, inner salt; 3,4-dihydro-2-[2-(sulfooxy)-3-(tetradecyloxy)propyl]isoquinolinium, inner salt; 2-[3-(dodecyloxy)-2-(sulfooxy)propyl]-3,4 dihydroisoquinolinium, inner salt; 2-[3-[(3-hexyldecyl)oxy]-2-(sulfooxy)propyl]-3,4-dihydroisoquinolinium, inner salt 3,4-dihydro-2-[3-[(2-pentylnonyl)oxy]-2-(sulfooxy)propyl]isoquinolinium, inner salt; 3,4-dihydro-2-[3-[(2-propylheptyl)oxy]-2-(sulfooxy)propyl]isoquinolinium, inner salt; 2-[3-[(2-butyloctyl)oxy]-2-(sulfooxy)propyl]-3,4-dihydroisoquinolinium, inner salt; 2-[3-(decyloxy)-2-(sulfooxy)propyl]-3,4-dihydroisoquinolinium, inner salt; 3,4-dihydro-2-[3-(octyloxy)-2-(sulfooxy)propyl]isoquinolinium, inner salt; and 2-[3-[(2-ethylhexyl)oxy]-2-(sulfooxy)propyl]-3,4-dihydroisoquinolinium, inner salt.

In embodiments, the water-based and/or water soluble benefit agent can include one or more activators. In embodiments, the activator can include one or more of tetraacetyl ethylene diamine (TAED); benzoylcaprolactam (BzCL); 4-nitrobenzoylcaprolactam; 3-chlorobenzoylcaprolactam; benzoyloxybenzenesulphonate (BOBS); nonanoyloxybenzene-sulphonate (NOBS); phenyl benzoate (PhBz); decanoyloxybenzenesulphonate ($C_{10}$-OBS); benzoylvalerolactam (BZVL); octanoyloxybenzenesulphonate ($C_8$-OBS); perhydrolyzable esters; 4-[N-(nonaoyl) amino hexanoyloxy]-benzene sulfonate sodium salt (NACA-OBS); dodecanoyloxybenzenesulphonate (LOBS or $C_{12}$-OBS); 10-undecenoyloxybenzenesulfonate (UDOBS or $C_{11}$-OBS with unsaturation in the 10 position); decanoyloxybenzoic acid (DOBA); (6-oclanamidocaproyl)oxybenzenesulfonate; (6-nonanamidocaproyl) oxybenzenesulfonate; and (6-decananidocaproyl)oxybenzenesulfonate.

In embodiments, the water-based and/or water soluble benefit agent can include one or more preformed peroxy carboxylic acids. In embodiments, the peroxy carboxylic acids can include one or more of peroxyrnonosulfuric acids; perimidic acids; percabonic acids; percarboxilic acids and salts of said acids; phthalimidoperoxyhexanoic acid; amidoperoxyacids; 1,12-diperoxydodecanedioic acid; and monoperoxyphthalic acid (magnesium salt hexahydrate), wherein said amidoperoxyacids may include N,N'-terephthaloyl-di(6-aminocaproic acid), a mononoylamide of either peroxysuccinic acid (NAPSA) or of peroxyadipic acid (NAPAA), or N-nonanovlaminoperoxycaproic acid (NAPCA).

In embodiments, the water-based and/or water soluble benefit agent can include one or more diacyl peroxide. In embodiments, the diacyl peroxide can include one or more of dinonanoyl peroxide, didecanoyl peroxide, diundecanoyl peroxide, dilauroyl peroxide, and dibenzoyl peroxide, di-(3,5,5-trimethyl hexanoyl) peroxide, wherein said diacyl peroxide can be clatharated.

In embodiments, the water-based and/or water soluble benefit agent can include one or more hydrogen peroxide. In embodiments, hydrogen peroxide source can include one or more of a perborate, a percarbonate a peroxyhydrate, a peroxide, a persulfate and mixtures thereof, in one aspect said hydrogen peroxide source may comprise sodium perborate, in one aspect said sodium perborate may comprise a mono- or tetra-hydrate, sodium pyrophosphate peroxyhydrate, urea peroxyhydrate, trisodium phosphate peroxyhydrate, and sodium peroxide.

In embodiments, the water-based and/or water soluble benefit agent can include one or more enzymes. In embodiment, the enzyme can include one or more of peroxidases, proteases, lipases, phospholipases, cellulases, cellobiohydrolases, cellobiose dehydrogenases, esterases, cutinases, pectinases, man nanases, pectate lyases, keratinases, recductases, oxidases, phenoloxidases, lipoxygenases, ligninases, pullulanases, tannases, pentosanases, glucanases, arabinosidases, hyaluronidase, chondroitinase, laccases, amnylases, and dnases.

In embodiments, the water-based and/or water-soluble benefit agent can include a perfume or a perfume composition. In embodiments, the perfume composition can include one or more of perfume raw materials, essential oils, malodour reducing agents, and odour controlling agents.

In various embodiments, the perfume composition can include one or more perfume raw materials. In embodiments, the perfume composition can include, by weight based on the total weight of the perfume composition, a combination of or individually (1) about 35% to about 60%, or about 40% to about 55%, of first perfume raw materials characterized by a log P of less than 1.5 and a boiling point of less than 250° C.; (2) about 10% to about 45%, or about 12% to about 40%, of second perfume raw materials characterized by a log P of less than or equal to 1.5 and a boiling point greater than or equal to 250° C.; (3) about 2.5% to about 30%, or about 5% to about 30%, of third perfume raw materials characterized by having a log P of greater than 1.5 and a boiling point of less than 250° C.; and (4) about 5% to about 30%, or about 7% to about 25%, of fourth perfume raw materials characterized by having a log P greater than 1.5 and a boiling point greater than 250° C.

In embodiments, the benefit agent can have an average log P less than or equal to 1.

Methods of Making Oil-Based Core Capsules

In embodiments of the method of making capsules having an oil-based core, the oil phase can include an oil-based and/or oil-soluble benefit agent and a precursor.

In embodiments, the precursor is present in an amount of about 1 wt % to about 50 wt % based on the total weight of the oil phase. Other suitable amounts include about 1 wt % to about 15 wt %, about 5 wt % to about 30 wt %, about 10 wt % to about 20 wt %, about 15 wt % to about 40 wt %, about 25 wt % to about 45 wt %, or about 15 wt % to about 50 wt %, based on the total weight of the oil phase. For example, the oil phase can include, based on the total weight of the oil phase, about 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, or 50 wt %.

In embodiments, the oil phase, prior to emulsification, can include about 10 wt % to about 99 wt % benefit agent based on the total weight of the oil phase, or about 20 wt % to about 99 wt %, about 40 wt % to about 99 wt %, or about 50 wt % to about 99 wt %, or about 50 wt % to about 90 wt %. For example, the benefit agent can be present in an amount based on the total weight of the oil phase of about 10 wt %, 20 wt %, 30 wt %, 40 wt %, 50 wt %, 60 wt %, 70 wt %, 80 wt %, or 90 wt %.

The oil phase can further include one or more oil-soluble core-modifiers. For example, an oil-soluble core modifier can be one or more of partitioning modifier and/or a density modifier. In embodiments, the partitioning modifier can include oil soluble materials that have a log P greater than about 1, or greater than about 2, or greater than about 3, or greater than about 4, or greater than about 5, or greater than about 6, or greater than about 7, or greater than about 8, or greater than about 9, or greater than about 10, or greater than about 11. In embodiments, the partitioning modifier can include oil soluble materials with a density of greater than or equal to 1 gram per cubic centimeter. In embodiments, the partitioning modifier can include one or more of a mono-ester, di-ester and tri-esters of $C_4$-$C_{24}$ fatty acids and glycerine; fatty acid esters of polyglycerol oligomers; polyalphaolefins; silicone oil; crosslinked silicones comprising polyether substituted structural units and acrylate crosslinks; polyglycerol ether silicone crosspolymers; alkyl substituted cellulose; hydroxypropyl cellulose; fatty esters of acrylic or methacrylic acid that have side chain crystallizing groups; copolymers of ethylene, including ethylene and vinyl acetate, ethylene and vinyl alcohol, ethylene/acrylic elastomers; acetyl caryophyllene, hexarose, butyl oleate, hydrogenated castor oil, sucrose benzoate, dodecanoic acid, palmitic acid, stearic acid, tetradecanol, hexadecanol, 1-octanediol, isopropyl myristate, castor oil, mineral oil, isoparaffin, caprylic triglyceride, soybean oil, vegetable oil, brominated vegetable oil, bromoheptane, sucrose octaacetate, geranyl palmitate, acetylcaryophyllene, sucrose benzoate, butyl oleate, silicones, polydimethylsiloxane, vitamin E, decamethylcyclopentasiloxane, dodecamethylcyclohxasiloxane, sucrose soyate, sucrose stearate, sucrose soyanate, lauryl alcohol, 1-tetradecanol, 1-hexadecanol, cetyl alcohol, 1-octadecanol, 1-docosanol, 2-octyl-1-dodecanol, perfume oils, in one aspect perfume oils having a log P>5, in one aspect said perfume oils may be selected from the group consisting of: Octadecanoic acid, octadecyl ester; Tetracosane, 2,6,10,15,19,23-hexamethyl-; Octadecanoic acid, diester dissolved in 1,2,3-propanetriol; Isotridecane, 1,1'-[(3,7-dimethyl-6-octenylidene)bis(oxy)]bis-; Tetradecanoic acid, octadecyl ester; 2,6,10,14,18,22-Tetracosahexaene, 2,6,10,15,19,23-hexamethyl-, (all-E)-; Tricosane; Docosane; Hexadecanoic acid, dodecyl ester; 1,2-Benzenedicarboxylic acid, didodecyl ester; Decanoic acid, 1,2,3-propanetriyl ester; 1-Undecene, 11,11-bis[(3,7-dimethyl-6-octenyl)oxy]-; Heneicosane; Benzene, [2-[bis[(3,7-dimethyl-2,6-octadienyl)oxy]methyl]-1-; 1-Undecene, 11,11-bis[(3,7-dimethyl-2,6-octadienyl)oxy]-; Benzene, [2-[bis[(1-ethenyl-1,5-dimethyl-4-hexenyl)oxy]methyl]-1-; Dodecanoic acid, tetradecyl ester; 2H-1-Benzopyran-6-ol, 3,4-dihydro-2,5,7,8-tetramethyl-2-(4,8,12-trimethyltridecyl)-, [2R-[2R*(4R*,8R*)]]-; Octanoic acid, octadecyl ester; Eicosane; 2H-1-Benzopyran-6-ol, 3,4-dihydro-2,5,8-trimethyl-2-(4,8,12-trimethyltridecyl)-, [2R*(4R*,8R*)]-; 2-Naphthalenol, 1-[6-(2,2-dimethyl-6-methylenecyclohexyl)-4-methyl-3-hexenyl]decahydro-2,5,5,8a-tetramethyl-, [1R-[1.alpha.[E(S*)],2.beta.,4a.beta.,8a.alpha.]]-; 2H-1-Benzopyran-6-ol, 3,4-dihydro-2,7,8-trimethyl-2-(4,8,12-trimethyltridecyl)-, [2R-[2R*(4R*,8R*)]]-; Heptanoic acid, octadecyl ester; Nonadecane; 2,4,6,8,10,12,14,16-Heptadecaoctaenal,2,6,11,15-tetramethyl-17-(2,6,6-trimethyl-1-cyclohexen-1-yl)-, (2E,4E,6E,8E,10E,12E,14E,16E)-; 2H-1-Benzopyran-6-ol, 3,4-dihydro-2,8-dimethyl-2-

(4,8,12-trimethyltridecyl)-, [2R-[2R*(4R*,8R*)]]-; Hexadecanoic acid, 2-ethylhexyl ester; 1,2-Benzenedicarboxylic acid, didecyl ester; Octadecane; Benzoic acid, 2-[[2-(phenylmethylene)octylidene]amino]-,1-ethenyl-1,5-dimethyl-4-hexenylester; Octadecanoic acid, 3-methylbutyl ester; Decanoic acid, ester with 1,2,3-propanetriol octanoate; Heptadecane; 1-Hexadecene, 7,11,15-trimethyl-3-methylene-; Dodecanoic acid, decyl ester; Octadecanoic acid, butyl ester; Decanedioic acid, bis(2-ethylhexyl) ester; Benzene, [2,2-bis[(3,7-dimethyl-6-octenyl)oxy]ethyl]-; Benzene, [2,2-bis[(3,7-dimethyl-2,6-octadienyl)oxy]ethyl]-; 9-Octadecenoic acid (Z)-, butyl ester; Octanoic acid, 1,2,3-propanetriyl ester; Hexadecane; Cyclohexene, 4-(5-methyl-1-methylene-4-hexenyl)-1-(4-methyl-3-pentenyl)-; 2-Hexadecen-1-ol, 3,7,11,15-tetramethyl-, acetate, [R-[R*,R*-(E)]]-Hexadecanoic acid, butyl ester; Octadecanoic acid, ethyl ester; 1-Dodecanol, 2-octyl-; Pentadecane; Tetradecanoic acid, hexyl ester; Decanoic acid, decyl ester; Acetic acid, octadecyl ester; Hexadecanoic acid, 2-methylpropyl ester; 9-Octadecenoic acid (Z)-, ethyl ester; Heptadecanoic acid, ethyl ester; Octadecanoic acid, methyl ester; Tetradecane; Tetradecanoic acid, 3-methylbutyl ester; 2-Hexadecen-1-ol, 3,7,11,15-tetramethyl-, [R-[R*,R*-(E)]]-; 2-Hexadecen-1-ol, 3,7,11,15-tetramethyl-; Hexadecanoic acid, 1-methylethyl ester; 1H-Indole, 1,1'-(3,7-dimethyl-6-octenylidene)bis-; Octadecanoic acid; Cyclopentasiloxane, decamethyl-; Benzoic acid, 2-[[2-(phenylmethylene)octylidene]amino]-,3-methylbutyl ester; 9,12-Octadecadienoic acid (Z,Z)-, ethyl ester; 1-Octadecanol; Hexanedioic acid, dioctyl ester; 9-Octadecenoic acid (Z)-, methyl ester; Octadecanoic acid, 2-hydroxypropyl ester; Tetradecanoic acid, butyl ester; Dodecanoic acid, hexyl ester; 9,12,15-Octadecatrienoic acid, ethyl ester, (Z,Z,Z)-; Hexadecanoic acid, ethyl ester; 1-Hexadecanol, acetate; 9-Octadecenoic acid (Z)-; Hexanedioic acid, bis(2-ethylhexyl) ester; 1,8,11,14-Heptadecatetraene; 1,8,11,14-Heptadecatetraene; 1,8,11,14-Heptadecatetraene; 9-Octadecen-1-ol, (Z)-; Tetradecanoic acid, 2-methylpropyl ester; Nonanoic acid, 1-methyl-1,2-ethanediyl ester; Tridecane; Naphthalene, decahydro-1,6-dimethyl-4-(1-methylethyl)-, [1S-(1.alpha.,4.alpha.,4a.alpha., 6.alpha.,8a.beta.)]-, didehydro deriv.; 1-Hexadecyn-3-ol, 3,7,11,15-tetramethyl-; 9,12-Octadecadienoic acid (Z,Z)-, methyl ester; 1-Heptadecanol; 6,10,14-Hexadecatrien-3-ol, 3,7,11,15-tetramethyl-; Benzoic acid, 2-[[[4-(4-methyl-3-pentenyl)-3-cyclohexen-1-yl]methylene]amino]-, methyl ester; 9,12-Octadecadienoic acid (Z,Z)-; 2-Nonene, 1,1'-oxybis-; Santalol, benzeneacetate; 10-Undecenoic acid, heptyl ester; 9,12,15-Octadecatrienoic acid, methyl ester, (Z,Z,Z)-; Octadecanoic acid, monoester with 1,2,3-propanetriol; Dodecanoic acid, pentyl ester; Octanoic acid, nonyl ester; Pentadecanoic acid, ethyl ester; Hexadecanoic acid, methyl ester; Dodecanoic acid, 4-methylphenyl ester; Dodecanoic acid, 3-methylbutyl ester; Tetradecanoic acid, 1-methylethyl ester; Hexadecanoic acid; 1-Phenanthrenecarboxylic acid, tetradecahydro-1,4a-dimethyl-7-(1-methylethyl)-, methyl ester, [1R-(1.alpha.,4a.beta.,4b.alpha.,7.beta.,8a.beta., 10a.alpha.)]-; 1-Hexadecanol; Dodecane; 2-Pentadecanone, 6,10,14-trimethyl-; 9-Heptadecanone; 1-Phenanthrenemethanol, 1,2,3,4,4a,4b,5,6,10,10a-decahydro-1,4a-dimethyl-7-(1-methylethyl)-, acetate, [1R-(1.alpha.,4a.beta., 4b.alpha.,10a.alpha.)]-; Isohexadecanol; Dodecanoic acid, 2-methylpropyl ester; Hexadecanenitrile; Octadecanoic acid, 2,3-dihydroxypropyl ester; Isododecane; 1-Phenanthrenemethanol, tetradecahydro-1,4a-dimethyl-7-(1-methylethyl)-; Octanoic acid, 3,7-dimethyl-2,6-octadienyl ester, (E)-; Dodecanoic acid, butyl ester; Tetradecanoic acid, ethyl ester; Butanoic acid, dodecyl ester; Benzoic acid, 2-amino-, decyl ester; Oxacycloheptadecan-2-one; Propanoic acid, 2-methyl-, dodecyl ester; 1H-Indene, octahydro-1,1,2,3,3-pentamethyl-; 1-Phenanthrenecarboxylic acid, 1,2,3,4,4a,4b,5,6,7,8,10,10a-dodecahydro-1,4a-dimethyl-7-(1-methylethyl)-, methyl ester; 9-Octadecenoic acid (Z)-, ester with 1,2,3-propanetriol; 9,12,15-Octadecatrienoic acid, (Z,Z,Z)-; 1,4,8-Cycloundecatriene, 2,6,6,9-tetramethyl-, (E,E,E)-; 1-Phenanthrenemethanol, dodecahydro-1, 4a-dimethyl-7-(1-methylethyl)-; Benzoic acid, 3,4,5-trihydroxy-, dodecyl ester; 1H-Indole-1-heptanol, .eta.-1H-indol-1-yl-.alpha.,.alpha.,.epsilon.-; Cyclododecane; 9-Hexadecenoic acid, (Z)-; Benzoic acid, 2-[[2-(phenylmethylene) heptylidene]amino]-, methyl; 9-Octadecenoic acid (Z)-, 2,3-dihydroxypropyl ester; 2-Naphthalenecarboxaldehyde, 5,6, 7,8-tetrahydro-3,5,5,6,7,8,8-heptamethyl-, trans-; Octanoic acid, 1-ethenyl-1,5-dimethyl-4-hexenyl ester; and 2-Hexadecanone.

In embodiments, the density modifiers can include one or more of brominated vegetable oil; sucrose octaacetate; bromoheptane; titanium dioxide; zinc oxides; iron oxides; cobalt oxides; nickel oxides; silver oxides; copper oxides; zirconium oxides; silica; silver; zinc; iron; cobalt; nickel; copper; epoxidized soybean oil polyols; 1h-indene, 2,3-dihydro-1,1,3,3,5-pentamethyl-4,6-dinitro-; benzene, (2-bromoethenyl)-; benzeneacetic acid, 2-methoxy-4-(1-propenyl)phenyl ester; ethanone, 1-(2,5-dimethyl-3-thienyl)-; oxiranecarboxylic acid, 3-(4-methoxyphenyl)-, ethyl ester; benzoic acid, 2-[(1-hydroxy-3-phenylbutyl)amino]-, methyl ester; 1,3-benzodioxole-5-carboxylic acid, ethyl ester; 1,3-benzodioxole, 5-(2-propenyl)-; benzoic acid, 4-methoxy-; benzenemethanol, .alpha.-(trichloromethyl)-, acetate; phenol, 2-methoxy-4-(2-propenyl)-, formate; phenol, 2-methoxy-4-(2-propenyl)-, benzoate; 2-propen-1-ol, 3-phenyl-, benzoate; benzeneacetic acid, 3-methylphenyl ester; benzene, 1-(1,1-dimethylethyl)-3,4,5-trimethyl-2,6-dinitro-; benzeneacetic acid, 4-methylphenyl ester; benzeneacetic acid, phenylmethyl ester; benzeneacetic acid, (4-methoxyphenyl)methyl ester; 2-propenoic acid, 3-phenyl-, phenylmethyl ester; 2-propenoic acid, 3-phenyl-, 2-phenylethyl ester; benzeneacetic acid, 2-methoxy-4-(2-propenyl)phenyl ester; phenol, 2-(methylthio)-; benzoic acid, 2-[[3-(1,3-benzodioxol-5-yl)-2-methylpropylidene] amino]-, methyl ester; benzoic acid, 2-[[3-(4-methoxyphenyl)-2-methylpropylidene]amino]-,methyl ester; benzoic acid, 3,5-dimethoxy-; benzoic acid, 2-hydroxy-, phenyl ester; benzoic acid, 2-hydroxy-, phenylmethyl ester; benzoic acid, 2-hydroxy-, ethyl ester; benzoic acid, 2-hydroxy-, methyl ester; benzoic acid, 2-amino-, methyl ester; ethanone, 2-hydroxy-1,2-diphenyl-; benzoic acid, 4-hydroxy-, ethyl ester; benzoic acid, phenylmethyl ester; 1,3-benzodioxole, 5-(1-propenyl)-; benzothiazole, 2-methyl-; 5h-dibenzo[a,d]cyclohepten-5-one, 10,11-dihydro-; oxiranecarboxylic acid, 3-phenyl-, ethyl ester; benzoic acid, 4-methoxy-, methyl ester; 2-propenoic acid, 3-phenyl-, 3-phenyl-2-propenyl ester; tricyclo[3.3.1.13,7]decan-2-ol, 4-methyl-8-methylene-; tricyclo[3.3.1.13,7]decan-2-ol, 4-methyl-8-methylene-, acetate; methanone, bis(2,4-dihydroxyphenyl)-; methanone, (2-hydroxy-4-methoxyphenyl) phenyl-; dibenzofuran; benzoic acid, 2-amino-, 2-phenylethyl ester; ethanone,1-(naphthalenyl)-; furan,2,2'-[thiobis (methylene)]bis-; 1,2,3-propanetriol, tripropanoate; 2-propenoic acid, 3-phenyl-, (e)-; phenol, 4-ethyl-2,6-dimethoxy-; disulfide, methyl phenyl; benzoic acid, 2-[[(4-methoxyphenyl)methylene]amino]-, methyl ester; 2-propenoic acid, 3-(2-methoxyphenyl)-, (z)-; 8-quinolinol; disulfide, bis(phenylmethyl); 1,2-propanediol, dibenzoate; benzene, 1-bromo-4-ethenyl-; trisulfide, di-2-propenyl; phenol, 2,6-dimethoxy-4-(1-propenyl)-, (e)-; benzene, (2-isothiocyanatoethyl)-; benzoic acid, 2-hydroxy-5-methyl-, methyl ester; 1,2,4-trithiolane, 3,5-dimethyl-; propanoic acid, 2-(methyldithio)-, ethyl ester; benzoic acid, 2-hydroxy-, cyclohexyl ester; benzoic acid, 2-[(1-oxopropyl) amino]-, methyl ester; ethanethioic acid, s-(4,5-dihydro-2-methyl-3-furanyl) ester; benzoic acid, 2-(acetylamino)-, methyl ester; 1,3,5-trithiane, 2,4,6-trimethyl-; benzoic acid, 2-amino-, propyl ester; butanoic acid, 1-naphthalenyl ester; benzoic acid, 2,4-dihydroxy-3-methyl-, methyl ester; trisulfide, methyl 2-propenyl; 2-furanmethanol, benzoate; benzoic acid, 2-hydroxy-5-methyl-, ethyl ester; benzene, (2,2-dichloro-1-methylcyclopropyl)-; 2-thiophenecarboxaldehyde, 5-ethyl-; benzoic acid, [(phenylmethylene)amino]-, methyl ester; spiro[1,3-dithiolo[4,5-b]furan-2,3'(2'h)-furan], hexahydro-2',3a-dimethyl-; 1,3-benzodioxole, 5-(diethoxymethyl)-; cyclododeca[c]furan, 1,3,3a,4,5,6,7,8,9,10,11,13a-dodecahydro-; benzeneacetic acid, 2-methoxyphenyl ester; 2-benzofurancarboxaldehyde; 1,2,4-trithiane, 3-methyl-; furan, 2,2'-[dithiobis(methylene)]bis-; 1,6-heptadiene-3,5-dione, 1,7-bis(4-hydroxy-3-methoxyphenyl)-, (e,e)-; benzoic acid, 2,4-dihydroxy-3,6-dimethyl-, methyl ester; benzoic acid, 2-hydroxy-4-methoxy-, methyl ester; propanoic acid, 2-methyl-, 1,3-benzodioxol-5-ylmethyl ester; 1,2,4-trithiolane, 3,5-diethyl-; 1,2,4-trithiolane, 3,5-bis(1-methylethyl)-; furan, 2-[(methyldithio)methyl]-; tetrasulfide, dimethyl; benzeneacetaldehyde, .alpha.-(2-furanylmethylene)-; benzoic acid, 3-methoxy-; benzenecarbothioic acid, s-methyl ester; benzoic acid, 2-methoxy-, methyl ester; benzoic acid, 2-hydroxy-, 4-methylphenyl ester; benzoic acid, 2-hydroxy-, propyl ester; 2-propenoic acid, 3-(2-methoxyphenyl)-; 2-propenoic acid, 3-(3-methoxyphenyl)-; benzoic acid, 2-hydroxy-4-methoxy-6-methyl-, ethyl ester; benzaldehyde, 2-hydroxy-5-methyl-; 1,2,3-propanetriol, tribenzoate; benzoic acid, 4-methylphenyl ester; 2-furancarboxylic acid, propyl ester; benzoic acid, 2-hydroxy-, 2-methylphenyl ester; benzoic acid, 4-hydroxy-3-methoxy-, ethyl ester; 2-propenoic acid, 3-phenyl-; benzene, 1,3-dibromo-2-methoxy-4-methyl-5-nitro-; benzene, (isothiocyanatomethyl)-; 2-propenoic acid, 3-(2-furanyl)-, ethyl ester; benzenemethanethiol, 4-methoxy-; 2-thiophenemethanethiol; benzene, 1,1'-[(2-phenylethylidene)bis(oxymethylene)]bis-; phenol, 2,6-dimethoxy-4-(2-propenyl)-; benzoic acid, 2-[(2-phenylethylidene)amino]-, methyl ester; benzenepropanoic acid, .beta.-oxo-, 4-methylphenyl ester; 1h-indole-3-heptanol, .eta.-1h-indol-3-yl-.alpha.,.alpha.,.epsilon.-trimethyl-; benzoic acid, 2-hydroxy-, 3-methyl-2-butenyl ester; 1,3-benzodioxole-5-propanol, .alpha.-methyl-, acetate; thiophene, 2,2'-dithiobis-; benzoic acid, 2-hydroxy-; benzaldehyde, 2-hydroxy-4-methyl-; disulfide, methyl phenylmethyl; 2-furancarboxylic acid, 2-phenylethyl ester; benzenethiol, 2-methoxy-; benzoic acid, 2-[[(4-hydroxy-3-methoxyphenyl)methylene]amino]-,methyl ester; ethanol, 2-(4-methylphenoxy)-1-(2-phenylethoxy)-; benzeneacetic acid, 3-phenyl-2-propenyl ester; benzoic acid, 2-amino-, 2-propenyl ester; bicyclo[3.2.1]octan-8-one, 1,5-dimethyl-, oxime; 2-thiophenethiol; phenol, 2-methoxy-4-(1-propenyl)-, formate; benzoic acid, 2-amino-, cyclohexyl ester; phenol, 4-ethenyl-2-methoxy-; benzoic acid, 2-hydroxy-, 2-(1-methylethoxy)ethyl ester; ethanone, 1-[4-(1,1-dimethylethyl)-2,6-dimethyl-3,5-dinitrophenyl]-; benzene, 1-(1,1-dimethylethyl)-3,5-dimethyl-2,4,6-trinitro-; 2-propenoic acid, 3-(4-methoxyphenyl)-; benzene, 1-(1,1-dimethylethyl)-2-methoxy-4-methyl-3,5-dinitro-; 1,2-benzenedicarboxylic acid, diethyl ester; ethanone, 1-(3,4-dihydro-2h-pyrrol-5-yl)-; benzoic acid, 2-(methylamino)-, methyl ester; 2h-1-benzopyran-2-one, 7-ethoxy-4-methyl-; benzoic acid, 2-hydroxy-, 2-phenylethyl ester; benzoic acid, 2-amino-, ethyl ester; 2-propen-1-ol, 3-phenyl-, 2-aminobenzoate; phenol, 4-chloro-3,5-dimethyl-; disulfide, diphenyl; 1-naphthalenol; [1,1'-biphenyl]-2-ol; benzenemethanol, .alpha.-phenyl-; 2-naphthalenethiol; ethanone, 1-(2-naphthalenyl)-; phenol, 2-methoxy-4-(1-propenyl)-, acetate; 2-naphthalenol, benzoate; benzoic acid, phenyl ester; pyridine, 2-[3-(2-chlorophenyl)propyl]-; benzoic acid, 4-hydroxy-, propyl ester; ethanone, 1-(1-naphthalenyl)-; propanoic acid, 3-[(2-furanylmethyl)thio]-, ethyl ester; 2-propen-1-one, 1,3-diphenyl-; 3-pyridinecarboxylic acid, phenylmethyl ester; benzoic acid, 2-phenylethyl ester; piperidine, 1-[5-(1,3-benzodioxol-5-yl)-1-oxo-2,4-pentadienyl]-,(e,e)-; and benzothiazole.

In embodiments of the method of making capsules having an oil-based core, the aqueous phase (continuous phase) can include water, an acid, and nanoparticles. In embodiments, the aqueous phase has a pH of about 1 to about 14 at least at the time of admixing with the oil phase. Other suitable pH include about 1 to about 5, about 2 to about 7, about 6 to about 7, about 1 to about 4, about 3 to about 7, about 7 to 14, about 8 to 10, about 9 to 11, or about 7 to 9. For example, the pH of the aqueous phase can be about 1, 2, 3, 4, 5, 6, 7, 8, 9, 10, 11, 12, 13 or 14.

In embodiments, the acid can be a strong acid. In embodiments, the strong acid can include one or more of HCl, $HNO_3$, $H_2SO_4$, HBr, HI, $HClO_4$, and $HClO_3$. In embodiments, the acid can include HCl. In embodiments, the concentration of the acid in continuous solution can be about 0.01 M to about 5 M, or about 0.1 M to about 5 M, or about 0.1 M to about 2 M, or about 0.1 M to about 1 M. For example, the concentration of acid in the continuous solution can be about 0.1 M, 0.2 M, 0.3 M, 0.4 M, 0.5 M, 1 M, 1.5 M, 2 M, 3 M, 4 M, or 5 M.

In embodiments, the acid can be a weak acid, such as HF and acetic acid.

In embodiments of the method of making capsules having an oil-based core, the aqueous phase (continuous phase) can include a base. In embodiments, the base can be one or more of mineral bases, a hydroxide, such as sodium hydroxide, and ammonia. For example, in embodiments, the base can be about $10^{-5}$ M to 0.01M NaOH, or about $10^{-5}$ M to about 1M ammonia.

In embodiments of the method of making capsules having an oil-based core, the pH can be varied throughout the process by the addition of an acid and/or a base. For example, the method can be initiated with an aqueous phase at an acidic or neutral pH and then a base can be added during the process to increase the pH. Alternatively, the method can be initiated with an aqueous phase at a basic or neutral pH and then an acid can be added during the process to decrease the pH. Still further, the method can be initiated with an aqueous phase at an acid or neutral pH and an acid can be added during the process to further reduce the pH. Yet further the method can be initiated with an aqueous phase at a basic or neutral pH and a base can be added during the process to further increase the pH. Any suitable pH shifts can be used. Further any suitable combinations of acids and bases can be used at any time in the method to achieve a desired pH.

Any of the nanoparticles described above can be used in the aqueous phase. In embodiments, the nanoparticles can be present in an amount of about 0.01 wt % to about 10 wt % based on the total weight of the aqueous phase. Other suitable amounts include about 0.05 wt % to about 5 wt %, about 1 wt % to about 10 wt %, about 5 wt % to about 8 wt %, about 2 wt % to about 7 wt %, or about 0.1 wt % to about 1 wt %. For example, the nanoparticles can be present in an amount based on the total weight of the aqueous phase of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt %.

In embodiments, the method can include admixing the oil phase and the aqueous phase in a ratio of oil phase to aqueous phase of about 1:10 to about 1:1, about 1:9 to about 1:1, about 1:5 to about 1:1, about 1:3 to about 1:1, about 1:5 to about 1:2, about 1:3 to about 1:1.5. Other suitable ratios include about 1:10, 1:9, 1:8, 1:7, 1:6, 1:5, 1:4, 1:3, 1:2, 2:5, 3:5, 1:1.5, or 1:1.

Methods of Making Aqueous Core Capsules

In embodiments of the method of making capsules having an aqueous core, the aqueous phase can include an aqueous benefit agent.

In embodiments, the aqueous phase, prior to emulsification, can include about 1 wt % to about 99 wt % benefit agent based on the total weight of the aqueous phase, or about 20 wt % to about 99 wt %, about 40 wt % to about 99 wt %, or about 50 wt % to about 99 wt %, or about 50 wt % to about 90 wt %. For example, the benefit agent can be present in an amount based on the total weight of the aqueous phase of about 1 wt %, 10 wt %, 20 wt %, 30 wt %, 40 wt %, 50 wt %, 60 wt %, 70 wt %, 80 wt %, or 90 wt %.

In embodiments, the aqueous phase can further include one or more core modifiers. For example, an aqueous core modifier can be one or more of a pH modifier, viscosity modifier, ionic strength modifiers, aesthetic modifiers, density modifiers, and gelling agents. In embodiments, the pH modifier may be incorporated to generate the desired pH in the core. In embodiments, the pH modifier can include any alkali or acid known to those skilled in the art of detergent manufacture, for example, among the alkalis: carbonate and hydroxycarbonate salts of alkaline or alkaline-earth metals, e.g., sodium or potassium hydroxide carbonate; oxides and hydroxides of alkaline or alkaline-earth metals, e.g., magnesium oxide, sodium or potassium hydroxide; citrate, fumarate, succinate, tartarate, maleate, ascorbate, silicate of alkaline or alkaline-earth metals, e.g., sodium citrate; among the acids: citric acid, fumaric acid, succinic acid, tartaric acid, malic acid, ascorbic acid, phosphoric acid, hydrochloric acid, sulfuric acid, sulforous acid.

In embodiments, the viscosity modifiers can include nanofibrillated and microfibrillated cellulose, uncoated or coated with a polymeric thickener, of bacterial or vegetable origin; non-polymeric crystalline, hydroxyl functional materials such as a crystallizable glyceride, including hydrogenated castor oil; naturally derived polymeric structurants such as hydroxyethyl cellulose, hydrophobically modified hydroxyethyl cellulose, carboxymethyl cellulose, polysaccharide derivatives. Suitable polysaccharide derivatives include: pectine, alginate, arabinogalactan (gum Arabic), carrageenan, gellan gum, xanthan gum, guar gum. Suitable viscosity modifiers which can be incorporated include synthetic polymeric structurants, e.g., polycarboxylates, polyacrylates, hydrophobically modified ethoxylated urethanes, hydrophobically modified non-ionic polyols; wherein the polycarboxylate polymer may include one or more of a polyacrylate, and polymethacrylate; a copolymer of unsaturated mono- or di-carbonic acid and $C_1$-$C_{30}$ alkyl ester of the (meth)acrylic acid.

In embodiments, the ionic strength modifiers can include one or more carboxylic acid, polycarboxylate, phosphate, phosphonate, polyphosphate, polyphosphonate, and borate. In embodiments, the ionic strength modifiers can further include one or more ionic species, such as one or more of oxydisuccinic acid, aconitic acid, citric acid, tartaric acid, malic acid, maleic acid, fumaric acid, succinic acid, sepacic acid, citaconic acid, adipic acid, itaconic acid, dodecanoic acid, acrylic acid homopolymers and copolymers of acrylic acid, maleic acid, calcium, magnesium, iron, manganese, cobalt, copper, and zinc ions.

In embodiments, the aesthetics modifiers can include one or more colorant, such as dyes or pigments and other aesthetic materials. Non-limiting examples of colorants include Rhodamine, Fluorescein, Phathalocyanine, and alumina. In embodiments, the aesthetics modifiers can include non-limiting examples of particles with different shapes and sizes that can include one or more of epoxy coated metalized aluminium polyethylene terephthalate, polyester beads, candelilla beads, silicates and mixtures thereof.

In embodiments, the density modifiers can include one or more of glycerol, mannitol, sugar alcohols, inorganic salts, ititanium dioxide; zinc oxides; iron oxides; cobalt oxides; nickel oxides; silver oxides; copper oxides; zirconium oxides; silica; silver; zinc; iron; cobalt; nickel; copper; In embodiments, the water soluble gelling agents can include one or more Lecithins, Calcium alginate, Agar, Carrageenan, Processed eucheuma seaweed, Locust bean gum, carob gum, Guar gum, Tragacanth, Acacia gum, gum arabic, Xanthan gum, Karaya gum, Tara gum, Gellan gum, Konjac, Polysorbates, Pectins, Ammonium phosphatides, Sucrose acetate isobutyrate, Glycerol esters of wood resins, Cellulose, Cellulose derivatives and fatty Acids.

In embodiments, the aqueous core can include an enzyme stabilizer. In embodiments, the enzyme stabilizer can include any conventional enzyme stabilizer such as water soluble sources of calcium and/or magnesium ions. In embodiments, the enzyme stabilizer can include one or more of a reversible protease inhibitor, such as a boron compound including borate, 4-formyl phenylboronic acid, phenylboronic acid and derivatives thereof, compounds such as calcium formate, sodium formate and 1,2-propane diol, and diethylene glycol.

In embodiments of methods of making capsules having an aqueous core, the oil phase can include a precursor. The precursor can be as defined above.

In embodiments, the precursor, present in the oil phase, can be present in an amount of about 1 wt % to about 50 wt % based on the total weight of the aqueous phase (which ultimately forms the core). Other suitable amounts include about 1 wt % to about 15 wt %, about 5 wt % to about 30 wt %, about 10 wt % to about 20 wt %, about 15 wt % to about 40 wt %, about 25 wt % to about 45 wt %, or about 15 wt % to about 50 wt %, based on the total weight of the aqueous phase. For example, the oil phase can include, based on the total weight of the aqueous phase, about 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, or 50 wt %.

In embodiments of method of making capsules having an aqueous core, nanoparticles can be present in one or both of the aqueous phase and the oil phase. In embodiments, the nanoparticles are present only in the aqueous phase. In embodiments, the nanoparticles are present only in the oil phase. In embodiments, the nanoparticles are present in both the oil phase and the aqueous phase.

Any of the nanoparticles described above can be used in the aqueous phase. In embodiments, the nanoparticles can be present in a total amount, whether in one or both of the aqueous and oil phases, of about 0.01 wt % to about 10 wt % based on the total weight of the aqueous phase. Other suitable amounts include about 0.05 wt % to about 5 wt %, about 1 wt % to about 10 wt %, about 5 wt % to about 8 wt %, about 2 wt % to about 7 wt %, or about 0.1 wt % to about 1 wt %. For example, the nanoparticles can be present in an amount based on the total weight of the aqueous phase of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt %.

In embodiments, the method includes admixing the oil phase and the aqueous phase in a ratio of about 10:1 to about 1:1, about 9:1 to about 1:1, about 5:1 to about 1:1, about 3:1 to about 1:1, about 5:1 to about 2:1, about 3:1 to about 1.5:1. Other suitable ratios include about 10:1, 9:1, 8:1, 7:1, 6:1, 5:1, 4:1, 3:1, 2:1, 1.5:1 or 1:1.

Curing Conditions

In embodiments, whether making an oil-based core or aqueous core, the emulsion can be cured under conditions to solidify the precursor thereby forming the capsules.

In embodiments, the reaction temperature for curing can be increased in order to increase the rate at which solidified capsules are obtained. Capsules are considered cured when they no longer collapse. Determination of capsule collapse is detailed below.

In embodiments, during the curing step, hydrolysis of Y moieties (from formula (I) and/or (II)) occurs, followed by the subsequent condensation of a —OH group with either another —OH group or another moiety of type Y (where the 2 Y are not necessarily the same). The hydrolysed precursor moieties will initially condense with the surface moieties of the nanoparticles (provided they contain such moieties). As the shell formation progresses, the precursor moieties will react with said preformed shell.

In embodiments, the emulsion can be cured such that the shell precursor undergoes condensation. In embodiments, the emulsion can be cured such that the shell precursor reacts with the nanoparticles to undergo condensation. Shown below are examples of the hydrolysis and condensation steps described herein for silica based shells:

Hydrolysis: ≡Si—OR+H$_2$O→≡Si—OH+ROH

Condensation: ≡Si—OH+≡Si—OR→☐Si—O—Si≡+ ROH

≡Si—OH+≡Si—OH→≡Si—O—Si≡+H$_2$O.

For example, in embodiments in which a precursor of formula (I) or (II) is used, the following describes the hydrolysis and condensation steps:

Hydrolysis: ≡M-Y+H$_2$O→≡M-OH+YH

Condensation: ≡M-OH+≡M-Y→≡M-O-M≡+YH

≡M-OH+≡M-OH→≡M-O-M≡+H$_2$O.

Test Methods

Mean Shell Thickness Measurement

The capsule shell, including the first shell component and the second shell component, when present, is measured in nanometers on 20 benefit agent containing delivery capsules making use of a Focused Ion Beam Scanning Electron Microscope (FIB-SEM; FEI Helios Nanolab 650) or equivalent. Samples are prepared by diluting a small volume of the liquid capsule dispersion (20 µl) with distilled water (1:10). The suspension is then deposited on an ethanol cleaned aluminium stub and transferred to a carbon coater (Leica EM ACE600 or equivalent). Samples are left to dry under vacuum in the coater (vacuum level: $10^{-5}$ mbar). Next 25-50 nm of carbon is flash deposited onto the sample to deposit a conductive carbon layer onto the surface. The aluminium stubs are then transferred to the FIB-SEM to prepare cross-sections of the capsules. Cross-sections are prepared by ion milling with 2.5 nA emission current at 30 kV accelerating voltage using the cross-section cleaning pattern. Images are acquired at 5.0 kV and 100 pA in immersion mode (dwell time approx. 10 µs) with a magnification of approx. 10,000.

Images are acquired of the fractured shell in cross-sectional view from 20 benefit delivery capsules selected in a random manner which is unbiased by their size, to create a representative sample of the distribution of capsules sizes present. The shell thickness of each of the 20 capsules is measured using the calibrated microscope software at 3 different random locations, by drawing a measurement line perpendicular to the tangent of the outer surface of the capsule shell. The 60 independent thickness measurements are recorded and used to calculate the mean thickness.

Coefficient of Variation of Capsule Diameter

Capsule size distribution is determined via single-particle optical sensing (SPOS), also called optical particle counting (OPC), using the AccuSizer 780 AD instrument or equivalent and the accompanying software CW788 version 1.82 (Particle Sizing Systems, Santa Barbara, California, U.S.A.), or equivalent. The instrument is configured with the following conditions and selections: Flow Rate=1 mL/sec; Lower Size Threshold=0.50 µm; Sensor Model Number=LE400-05SE or equivalent; Auto-dilution=On; Collection time=60 sec; Number channels=512; Vessel fluid volume=50 ml; Max coincidence=9200. The measurement is initiated by putting the sensor into a cold state by flushing with water until background counts are less than 100. A sample of delivery capsules in suspension is introduced, and its density of capsules adjusted with DI water as necessary via autodilution to result in capsule counts of at most 9200 per mL. During a time period of 60 seconds the suspension is analyzed. The range of size used was from 1 µm to 493.3 µm.

Volume Distribution:

$$CoVv(\%) = \frac{\sigma_v}{\mu_v} * 100$$

$$\sigma v = \sum_{i=1\,um}^{493.3\,um} (x_{i,v} * (d_i - \mu_v)^2) 0.5$$

$$\mu_v = \frac{\sum_{i=1\,um}^{493.3\,um} (x_{i,v} * d_i)}{\sum_{i=1\,um}^{493.3\,um} x_{i,v}}$$

Where:
CoV$_v$—Coefficient of variation of the volume weighted size distribution
σ$_v$—Standard deviation of distribution of volume distribution
µ$_v$—mean of the distribution of volume distribution
d$_i$—diameter in fraction i
x$_{i,v}$—frequency in fraction i (corresponding to diameter i) of volume distribution $$x_{i,v} = \frac{x_{i,n} * d_i^3}{\sum_{i=1\,um}^{493.3\,um}(x_{i,n} * d_i^3)}$$

Nominal Wall Tension Method

The nominal wall tension, $T_R$, is calculated using the following equation as described in "Liu, M. (2010). *Understanding the mechanical strength of microcapsules and their adhesion on fabric surfaces*. Birmingham, United Kingdom: University of Birmingham (Doctoral thesis)"

$$T_R = \frac{F_R}{\pi D_m}$$

where, $F_R$ is rupture force of a single microcapsule and Dm is diameter of a single capsule before compression. The nominal wall tension, $T_R$, is interpreted as tension or stretch of wall at rupture. The diameter ($D_m$) and the rupture-force value ($F_R$) (also known as the bursting-force value) of individual capsules are measured via a computer-controlled micromanipulation instrument system which possesses lenses and cameras able to image the delivery capsules, and which possess a fine, flat-ended probe connected to a force-transducer (such as the Model 403A available from Aurora Scientific Inc., Canada) or equivalent, as described in: Zhang, Z. et al. (1999) "Mechanical strength of single microcapsules determined by a novel micromanipulation technique." *J. Microencapsulation*, vol. 16, no. 1, pages 117-124, and in: Sun, G. and Zhang, Z. (2001) "Mechanical Properties of Melamine-Formaldehyde microcapsules." J. Microencapsulation, vol. 18, no. 5, pages 593-602, and as available at the University of Birmingham, Edgbaston, Birmingham, UK.

Nominal wall tension is determined as follows:
a) A drop of the delivery capsule suspension is placed onto a glass microscope slide and dried under ambient conditions for several minutes to remove the water and achieve a sparse, single layer of solitary capsules on the dry slide. The concentration of capsules in the suspension is adjusted as needed to achieve a suitable capsule density on the slide. More than one slide preparation may be needed.
b) The slide is then placed on a sample-holding stage of the micromanipulation instrument. Thirty benefit delivery capsules on the slide(s) are selected for measurement, such that there are ten capsules selected within each of three pre-determined size bands. Each size band refers to the diameter of the capsules as derived from the Accusizer-generated volume-weighted PSD. The three size bands of capsules are: the Mean Diameter+/−2 μm; the $5^{th}$ Percentile Diameter+/−2 μm; and the $90^{th}$ Percentile Diameter+/−2 μm. Capsules which appear deflated, leaking or damaged are excluded from the selection process and are not measured.
c) For each of the 30 selected capsules, the diameter of the capsule is measured from the image on the micromanipulator and recorded. That same capsule is then compressed between two flat surfaces, namely the flat-ended force probe and the glass microscope slide, at a speed of 2 μm per second, until the capsule is ruptured. During the compression step, the probe force is continuously measured and recorded by the data acquisition system of the micromanipulation instrument.
d) The diameter ($D_m$) of each capsule is measured using the experimental apparatus, or equivalent, and method of Zhang, Z.; Sun, G: "Mechanical Properties of Melamine-Formaldehyde microcapsules." J. Microencapsulation, Vol 18, no. 5, pages 593-602, 2001.
e) The rupture force ($F_R$) is determined for each selected capsule from the recorded force probe measurements, as demonstrated in Zhang, Z. et al. (1999) "Mechanical strength of single microcapsules determined by a novel micromanipulation technique." *J. Microencapsulation*, vol. 16, no. 1, pages 117-124, and in: Sun, G. and Zhang, Z. (2001) "Mechanical Properties of Melamine-Formaldehyde microcapsules." *J. Microencapsulation*, vol. 18, no. 5, pages 593-602.
f) The nominal wall tension ($T_R$) of each of the 30 capsules is calculated by dividing the rupture force ($F_R$) (in Newtons) by the diameter of the capsules ($D_m$) multiplied by 7c as described in "Liu, M. (2010). Understanding the mechanical strength of microcapsules and their adhesion on fabric surfaces. Birmingham, United Kingdom: University of Birmingham (Doctoral thesis)".

Effective Volumetric Core-Shell Ratio Evaluation

The effective volumetric core-shell ratio values were determined as follows, which relies upon the mean shell thickness as measured by the Shell Thickness Test Method. The effective volumetric core-shell ratio of capsules where their mean shell thickness was measured is calculated by the following equation:

$$\frac{\text{Core}}{\text{Shell}} = \frac{\left(1 - \frac{2*\text{Thickness}}{D_{caps}}\right)^3}{\left(1 - \left(1 - \frac{2*\text{Thickness}}{D_{caps}}\right)^3\right)}$$

wherein Thickness is the mean shell thickness of a population of capsules measured by FIBSEM and the $D_{caps}$ is the mean volume weighted diameter of the population of capsules measured by optical particle counting.

This ratio can be translated to fractional core-shell ratio values by calculating the core weight percentage using the following equation:

$$\%\,\text{Core} = \left(\frac{\frac{\text{Core}}{\text{Shell}}}{1 + \frac{\text{Core}}{\text{Shell}}}\right) * 100$$

and shell percentage can be calculated based on the following equation: % Shell=100−% Core.

Degree of Branching Method

The degree of branching of the precursors was determined as follows: Degree of branching is measured using (29Si) Nuclear Magnetic Resonance Spectroscopy (NMR).
Sample Preparation
Each sample is diluted to a 25% solution using deuterated benzene (Benzene-D6 "100%" (D, 99.96% available from Cambridge Isotope Laboratories Inc., Tewksbury, MA, or equivalent). 0.015M Chromium(III) acetylacetonate (99.99% purity, available from Sigma-Aldrich, St. Louis, MO, or equivalent) is added as a paramagnetic relaxation reagent. If glass NMR tubes (Wilmed-LabGlass, Vineland, NJ or equivalent) are used for analysis, a blank sample must also be prepared by filling an NMR tube with the same type of deuterated solvent used to dissolve the samples. The same glass tube must be used to analyze the blank and the sample.

Sample Analysis

The degree of branching is determined using a Bruker 400 MHz Nuclear Magnetic Resonance Spectroscopy (NMR) instrument, or equivalent. A standard silicon (29Si) method (e.g. from Bruker) is used with default parameter settings with a minimum of 1000 scans and a relaxation time of 30 seconds.

Sample Processing

The samples are stored and processed using system software appropriate for NMR spectroscopy such as MestReNova version 12.0.4-22023 (available from Mestrelab Research) or equivalent. Phase adjusting and background correction are applied. There is a large, broad, signal present that stretches from −70 to −136 ppm which is the result of using glass NMR tubes as well as glass present in the probe housing. This signal is suppressed by subtracting the spectra of the blank sample from the spectra of the synthesized sample provided that the same tube and the same method parameters are used to analyze the blank and the sample. To further account for any slight differences in data collection, tubes, etc., an area outside of the peaks of interest area should be integrated and normalized to a consistent value. For example, integrate −117 to −115 ppm and set the integration value to 4 for all blanks and samples.

The resulting spectra produces a maximum of five main peak areas. The first peak (Q0) corresponds to unreacted TAOS. The second set of peaks (Q1) corresponds to end groups. The next set of peaks (Q2) correspond to linear groups. The next set of broad peaks (Q3) are semi-dendritic units. The last set of broad peaks (Q4) are dendritic units. When PAOS and PBOS are analyzed, each group falls within a defined ppm range. Representative ranges are described in the following table:

| Group ID | # of Bridging Oxygen per Silicon | ppm Range |
| --- | --- | --- |
| Q0 | 0 | −80 to −84 |
| Q1 | 1 | −88 to −91 |
| Q2 | 2 | −93 to −98 |
| Q3 | 3 | −100 to −106 |
| Q4 | 4 | −108 to −115 |

Polymethoxysilane has a different chemical shift for Q0 and Q1, an overlapping signal for Q2, and an unchanged Q3 and Q4 as noted in the table below:

| Group ID | # of Bridging Oxygen per Silicon | ppm Range |
| --- | --- | --- |
| Q0 | 0 | −78 to −80 |
| Q1 | 1 | −85 to −88 |
| Q2 | 2 | −91 to −96 |
| Q3 | 3 | −100 to −106 |
| Q4 | 4 | −108 to −115 |

The ppm ranges indicated in the tables above may not apply to all monomers. Other monomers may cause altered chemical shifts, however, proper assignment of Q0-Q4 should not be affected.

Using MestReNova, each group of peaks is integrated, and the degree of branching can be calculated by the following equation:

$$\text{Degree of Branching} = 1/4 \frac{3^*Q3 + 4^*Q4}{Q1 + Q2 + Q3 + Q4}$$

Molecular Weight and Polydispersity Index Determination Method

The molecular weight (Polystyrene equivalent Weight Average Molecular Weight (Mw)) and polydispersity index (Mw/Mn) of the condensed layer precursors described herein are determined using Size Exclusion Chromatography with Refractive Index detection. Mn is the number average molecular weight.

Sample Preparation

Samples are weighed and then diluted with the solvent used in the instrument system to a targeted concentration of 10 mg/mL. For example, weigh 50 mg of polyalkoxysilane into a 5 mL volumetric flask, dissolve and dilute to volume with toluene. After the sample has dissolved in the solvent, it is passed through a 0.45 um nylon filter and loaded into the instrument autosampler.

Sample Analysis

An HPLC system with autosampler (e.g. Waters 2695 HPLC Separation Module, Waters Corporation, Milford MA, or equivalent) connected to a refractive index detector (e.g. Wyatt 2414 refractive index detector, Santa Barbara, CA, or equivalent) is used for polymer analysis. Separation is performed on three columns, each 7.8 mm I.D.×300 mm in length, packed with 5 μm polystyrene-divinylbenzene media, connected in series, which have molecular weight cutoffs of 1, 10, and 60 kDA, respectively. Suitable columns are the TSKGel G1000HHR, G2000HHR, and G3000HHR columns (available from TOSOH Bioscience, King of Prussia, PA) or equivalent. A 6 mm I.D.×40 mm long 5 μm polystyrene-divinylbenzene guard column (e.g. TSKgel Guardcolumn HHR-L, TOSOH Bioscience, or equivalent) is used to protect the analytical columns. Toluene (HPLC grade or equivalent) is pumped isocratically at 1.0 mL/min, with both the column and detector maintained at 25° C. 100 μL of the prepared sample is injected for analysis. The sample data is stored and processed using software with GPC calculation capability (e.g. ASTRA Version 6.1.7.17 software, available from Wyatt Technologies, Santa Barbara, CA or equivalent.)

The system is calibrated using ten or more narrowly dispersed polystyrene standards (e.g. Standard ReadyCal Set, (e.g. Sigma Aldrich, PN 76552, or equivalent) that have known molecular weights, ranging from about 0.250-70 kDa and using a third order fit for the Mp verses Retention Time Curve.

Using the system software, calculate and report Weight Average Molecular Weight (Mw) and PolyDispersity Index (Mw/Mn).

Benefit Agent Permeability Test

The permeability test method allows the determination of a percentage of diffusion of a specific molecule from the capsule core for a population of capsules into the continuous phase, which can be representative of the permeability of the capsule shells. The permeability test method is a referential frame that relates to shell permeability for a specific molecular tracer, hence fixing its size and its affinity towards the continuous phase exterior to the capsule shell. This is a referential frame that is used to compare the permeability of various capsules in the art. When both molecular tracer and continuous phase are fixed, the shell permeability is the single capsule property being assessed under a specific set of conditions.

The capsule shell permeability which correlates with shell porosity, such that low permeability is indicative of low shell porosity.

Capsule permeability is generally given as a function of parameters, such as the shell thickness, concentration of active within the core, solubility of the active in the core, the shell and the continuous phase, etc.

For diffusion of an active to occur across a shell, it must be transferred from the core into the shell, and from the shell into the continuous phase. This latter step is rapid if the solubility of the active in the continuous phase is highly favored, which is the case of hydrophobic materials into a surfactant-based matrix. For example, an active that is present at levels of 0.025 w % in a system is very likely to be fully solubilized into 15 w % of surfactants.

Considering the above, the limiting step to allow for minimal shell permeability for an active in a surfactant-based matrix, is to limit the diffusion across the shell. For hydrophobic shell materials, a hydrophobic active is readily soluble in the shell in case it can be swollen by said active. This swellability can be limited by high shell crosslink densities.

For hydrophilic shell materials, such as silicon dioxide, a hydrophobic material has limited solubility in the shell itself. Nevertheless, an active is capable of rapidly diffusing out when considering the following factors: surfactant molecules and micelles are capable of diffusing into the shell, and subsequently into the core itself, which allows for a pathway from the core into the shell and finally the exterior matrix.

Therefore, in the case of hydrophilic shell materials, a high shell crosslink density is required, but also reduced quantity of pores within the shell. Such pores can lead to fast mass transfer of an active into a surfactant-based matrix. Thus, there is a clear and obvious link between the overall permeability of a capsule shell and its porosity. In fact, the permeability of a capsule gives insight into the overall shell architecture of any given capsule.

As discussed previously, diffusion of an active is defined by the nature of the active, its solubility in the continuous phase, and the shell architecture (porosity, crosslink density and any general defects it might contain). Therefore, by fixing two of the three relevant parameters, we can in effect compare the permeability of various shells.

The purpose of this permeability test is to provide such a framework that allows for direct comparisons of different capsule shells. Moreover, it allows for the evaluation of the properties of a large population of capsules and therefore does not suffer from skewed results obtained by outliers.

Therefore, the capsule permeability can be defined via the fraction of a given molecular tracer that diffused into a given continuous phase within a given period of time under specific conditions (e.g. 20% tracer diffusion within 7 days).

Capsules of this invention will have a relative permeability as measured by the Permeability Test Method of less than about 80%, less than about 70%, less than about 60%, less than about 50%, less than about 40%, less than about 30%, or less than about 20%.

The Permeability Test Method determines the shell permeability for a molecular tracer, Verdyl Acetate (CAS #5413-60-5) (Vigon) from capsules containing the tracer in their core relative to reference sample representing complete diffusion of the said tracer (e.g. 100% permeability).

First, capsules are prepared according to any given capsules preparation method. For purposes of the Permeability Test method the capsule core must include or be supplemented during preparation to include at least 10% by weight of the core of the Verdyl Acetate tracer. The "weight of the core" in this test refers to the weight of the core after the shell has been formed and the capsule is made. The capsule core otherwise includes its intended components such as core modifiers and benefit agents. Capsules can be prepared as a capsule slurry as is commonly done in the art.

The capsules are then formulated into a Permeability Test sample. The Permeability Test sample includes mixing enough of the capsule slurry with an aqueous solution of sodium dodecyl sulfate (CAS #151-21-3) to achieve a total core oil content of 0.25 wt % 0.025% and a SDS concentration of 15 wt % 1 wt % based on the total weight of the test sample. The amount of capsules slurry needed can be calculated as follows:

$$\frac{\text{Mass (slurry)} * OilActivity \text{ (slurry)}}{\text{Mass } (SDS \text{ solution)} + \text{Mass (Slurry)}} = 0.2500 \text{ wt \%}$$

where the OilActivity of the slurry is the wt % of oil in the slurry as determined via the mass balance of the capsule making process.

The SDS solution can be prepared by dissolving SDS pellets in deionized water. The capsules and the SDS solution can be mixed under conditions designed to prevent breakage of the capsules during mixing. For example, the capsules and the SDS solution can be mixed together by hand or with an overhead mixer, but should not be mixed with a magnetic stir bar. It has been found that mixing by magnetic stir bar often leads to breakage of the capsules. Suitable mixtures can include an IKA propeller type mixer, at no more than 400 rpm, wherein the total mass of the mixture including SDS solution and capsule slurry is from 10 g to 50 g. Other suitable mixing equipment and suitable conditions for mixing without use of magnetic stir bars and without breakage a given capsules composition would be readily apparent to the skilled person.

Once prepared, the Permeability Test sample is placed in a glass vial having a total volume of no more than two times the volume of the Permeability Test sample and sealed with an airtight lid. The sealed Permeability Test sample is stored at 35° C. and 40% relative humidity for seven days. During storage, the sealed Permeability Test sample is not exposed to light and is not opened at any point prior to measurement.

A reference sample representing 100% diffusion is also prepared. The reference sample is prepared to be ready on the day of measurement (i.e., seven days after preparation of the Permeability Test sample.) The reference sample is prepared by combining a free oil mixture intended to duplicate the composition of the core of the capsules as determined by mass balance of the capsule making in the Permeability Test sample, including the same percentage by weight of the core of the Verdyl Acetate tracer, with 15% by weight aqueous SDS. The free oil mixture and the SDS solution are homogenized with a magnetic stirrer until complete solubilization of the free oil mixture, and the vessel should be sealed during mixing to avoid evaporation of the tracer. If the homogenization takes considerable time, this must be considered and the starting of the preparation of the reference can be started before day 7 if necessary. Immediately after solubilization, the reference sample is placed into a glass vial no more than two times the volume of the reference sample and sealed with an airtight lid. The SDS solution can be prepared as in the Permeability Test sample by dissolving SDS pellets in deionized water.

The amount of free oil mixture is added to achieve a total concentration of free oil mixture in the reference sample of 0.25 wt % 0.025% based on the total weight of the reference sample, as calculated by the following:

$$\frac{\text{Mass (Capsule core)}}{\text{Mass (SDS solution)} + \text{Mass (Capsule core)}} = 0.2500 \ w\ \%$$

Permeability, as represented by a gas chromatography area count of the Verdyl Acetate, is analyzed for the Permeability Test sample (after seven days) and the reference sample on the same day using the same GC/MS analysis equipment. In particular, for each sample, test and reference, aliquots of 100 µL of sample are transferred to 20 ml headspace vials (Gerstel SPME vial 20 ml, part no. 093640-035-00) and immediately sealed (sealed with Gerstel Crimp caps for SPME, part no. 093640-050-00). Three headspace vials are prepared for each sample. The sealed headspace vials are then allowed to equilibrate. Samples reach equilibrium after 3 hours at room temperature, but can be left to sit longer without detriment or change to the results, up until 24 hours after sealing the headspace vial. After equilibrating, the samples are analyzed by GC/MS.

GS/MS analysis are performed by sampling the headspace of each vial via SPME (50/30 µm DVB/Carboxen/PDMS, Sigma-Aldrich part #57329-U), with a vial penetration of 25 millimeters and an extraction time of 1 minute at room temperature. The SPME fiber is subsequently on-line thermally desorbed into the GC injector (270° C., splitless mode, 0.75 mm SPME Inlet liner (Restek, art #23434) or equivalent, 300 seconds desorption time and injector penetration of 43 millimeters). Verdyl acetate is analyzed by fast GC/MS in full scan mode. Ion extraction of the specific mass for Verdyl Acetate (m/z=66) is used to calculate the Verdyl Acetate (and isomers) headspace response (expressed in area counts). The headspace responses for the Permeability Test sample and the reference sample are referenced herein as Verdyl Acetate Area Count for Permeability Test Sample and Verdyl Acetate Area Count for Reference Sample, respectively.

Suitable equipment for use in this method includes Agilent 7890B GC with 5977MSD or equivalent, Gerstel MPS, SPME (autosampler), GC column: Agilent DB-5UI 30 m×0.25×0.25 column (part #122-5532UI).

Analysis of the Permeability Test sample and the reference sample should be done on the same equipment, under the same room temperature conditions, and on the same day, each immediately after the other one Based on the GC/MS data and the actual known content of Verdyl Acetate in the Permeability Test sample, the percent permeability can be calculated. The actual content of Verdyl Acetate in the Permeability Test must be determined to correct for any losses during the making of the capsules. The method to be used is specified below. This accounts for inefficiencies often encountered when encapsulating products in a capsule core, and less than the entire anticipated amount of Verdyl Acetate present during formation of the capsules being present in the slurry (e.g. evaporation). The following equation can be used to calculate the percent permeability.

$$\frac{\text{Verdyl Acetate Area Count for Leakage Test Sample}}{\text{Verdyl Acetate Area Count for Reference Sample}} *$$

$$\frac{100\%}{\text{wt \% Verdyl Acetate Actual}} * \frac{\text{oil \% Reference}}{\text{oil \% sample}} = \% \text{ permeability}$$

This calculated value is the % permeability of the tested capsules after 7 days of storage at 40% relative humidity and 35° C.

To evaluate the actual Verdyl Acetate content in the SDS capsule mixture, an aliquot must be retrieved after the specified storage time. For this, the resulting mixture is to be opened on the same day as the first samples are measured, thus ensuring that the vial stays sealed during storage. First, the mixture must be mixed until homogeneous, so that a representative aliquot containing the right proportions of materials is retrieved. Then, 1 gram of said homogeneous mixture is introduced into a flat bottom glass vial of a diameter of 1 cm, and a magnetic stirring bar of a length of no less than half the diameter of the vial is introduced into said vial. The homogeneous mixture in the specified jar containing the magnetic stirbar is sealed and then placed onto a magnetic stirring plate, and a mixing of 500 rpm is used so that the stirring action of the stirbar grinds all capsules. This results in total release of the encapsulated core material into the surrounding SDS solution, thus allowing for the measurement of the actual VerdylAcetate content. The measurement protocol of this content must be performed as for the unbroken capsules. In addition, prior to the measurement step, the capsules must be observed under an optical microscope to assess whether all capsules have been broken. If this is not the case, the capsule grinding must be repeated, with either increasing the mixing speed and/or the mixing time.

Method of Calculating Organic Content in First Shell Component

Definition of organic moiety in inorganic shell—Any moiety X that cannot be cleaved from a metal precursor bearing a metal M (where M belongs to the group of metals and semi-metals, and X belongs to the group of non-metals) via hydrolysis of the M-X bond linking said moiety to the inorganic precursor of metal or semi-metal M and under specific reaction conditions, will be considered as organic. A minimal degree of hydrolysis of 1% when exposed to neutral pH distilled water for a duration of 24 h without stirring, is set as the reaction conditions.

This method allows one to calculate a theoretical organic content assuming full conversion of all hydrolysable groups. As such, it allows one to assess a theoretical percentage of organic for any mixture of silanes and the result is only indicative of this precursor mixture itself, not the actual organic content in the first shell component. Therefore, when a certain percentage of organic content for the first shell component is disclosed anywhere in this document, it is to be understood as containing any mixture of unhydrolyzed or pre-polymerized precursors that according to the below calculations give a theoretical organic content below the disclosed number.

Example for Silane (but not Limited to Silane, See Generic Formulas at the End of the Document):

Consider a mixture of silanes, with a molar fraction Y for each, and where i is an ID number for each silane. Said mixture can be represented as follows:

$$Si(XR)_{4-n}R_n$$

Where XR is a hydrolysable group under conditions mentioned in the definition above, $R^i_{ni}$ is non-hydrolyzable under conditions mentioned above and n; =0, 1, 2 or 3.

Such a mixture of silanes will lead to a shell with the following general formula:

$$SiO_{\frac{(4-n)}{2}}R_n$$

Then, the weight percentage of organic moieties as defined earlier can be calculated as follows:
1) Find out Molar fraction of each precursor (nanoparticles included)
2) Determine general formula for each precursor (nanoparticles included)
3) Calculate general formula of precursor and nanoparticle mixture based on molar fractions
4) Transform into reacted silane (all hydrolysable groups to oxygen groups)
5) Calculate weight ratio of organic moieties vs. total mass (assuming 1 mole of Si for framework)

EXAMPLE

| Raw material | Formula | Mw (g/mol) | weight (g) | amount (mmol) | Molar fraction |
|---|---|---|---|---|---|
| Sample AY | SiO(OEt)$_2$ | 134 | 1 | 7.46 | 0.57 |
| TEOS | Si(OEt)$_4$ | 208 | 0.2 | 0.96 | 0.07 |
| DEDMS | Si(OEt)$_2$Me$_2$ | 148.27 | 0.2 | 1.35 | 0.10 |
| SiO2 NP | SiO$_2$ | 60 | 0.2 | 3.33 | 0.25 |

To calculate the general formula for the mixture, each atoms index in the individual formulas is to be multiplied by their respective molar fractions. Then, for the mixture, a sum of the fractionated indexes is to be taken when similar ones occur (typically for ethoxy groups).

Note: Sum of all Si fractions will always add to 1 in the mixture general formula, by virtue of the calculation method (sum of all molar fractions for Si yields 1).

$$SiO_{1*0.57+2*0.25}(OEt)_{2*0.57+4*0.07+2*0.10}Me_{2*0.10}$$
$$SiO_{1.07}(OEt)_{1.62}Me_{0.20}$$

To transform the unreacted formula to a reacted one, simply dividing the index of ALL hydrolysable groups by 2, and then adding them together (with any pre-existing oxygen groups if applicable) to obtain the fully reacted silane $$SiO_{1.88}Me_{0.20}$$

In this case, the expected result is $SiO_{1.9}Me_{0.2}$, as the sum of all indexes must follow the following formula:

$$A+B/2=2,$$

where A is the oxygen atom index and B is the sum of all non-hydrolysable indexes. The small error occurs from rounding up during calculations and should be corrected. The index on the oxygen atom is then readjusted to satisfy this formula.

Therefore, the final formula is $SiO_{1.9}Me_{0.2}$, and the weight ratio of organic is calculated below:

Weight ratio: =(0.20*15)/(28+1.9*16+0.20*15)=4.9%

General Case:

The above formulas can be generalized by considering the valency of the metal or semi-metal M, thus giving the following modified formulas:

$$M(XR)_{V-m}R^i_m$$

And using a similar method but considering the valency V for the respective metal.

EXAMPLES

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

Example 1: Non-Hydrolytic Precursor Synthesis

The Precursors for Samples A-S, AV-AAD were made by the following method:

A quantity of TAOS reagent(s) (available from Sigma Aldrich) were added to a clean dry round bottom flask equipped with a stir bar and distillation apparatus under nitrogen atmosphere. A volume of acetic anhydride (available from Sigma Aldrich) and catalyst (available from Gelest, Sigma Aldrich) were added and the contents of the flask were stirred and heated as indicated in the Table 1. The reaction was heated to the indicated temperature for the indicated amount of time, during which the organic ester generated by reaction of the alkoxy silane groups with acetic anhydride was distilled off along with additional organic esters generated by the condensation of silyl-acetate groups with other alkoxysilane groups which occurred as the polyalkoxysilane (PAOS) was generated. The reaction flask was cooled to room temperature and placed on a rotary evaporator (Buchi Rotovapor R110), used in conjunction with a water bath and vacuum pump (Welch 1402 DuoSeal) to remove any remaining solvent. All reactant and reagent types and ratios, catalysts and ratios, and all reaction conditions (e.g. time and temperature) are detailed in Table 1.

The following reactants can be abbreviated as follows: tetraethoxysilane (TEOS), tetramethoxysilane (TMOS), tetrabutoxysilane (TBOS), triethoxymethylsilane (TEMS), diethoxy-dimethylsilane (DEDMS), trimethylethoxysilane (TMES), tetraacetoxysilane (TAcS), and titanium tetrabutoxide (TTB).

Example 2: Hydrolytic Precursor Synthesis

The Precursors for Samples U-Z, AA-AI, and AK-AAB were made by the following method:

A quantity of TAOS reagent(s) (available from Sigma Aldrich) was added to a clean dry round bottom flask equipped with a stir bar and distillation apparatus under nitrogen atmosphere and to which was added a quantity of alcohol (available from Sigma Aldrich). A quantity of catalyst dissolved in water was added as indicated in the Table 2. 1N and 0.1N HCl dissolved in water are available from Sigma Aldrich. 0.002N HCl was prepared by diluting 0.1N HCl in distilled water (available from Sigma Aldrich). The reaction was stirred and heated to the indicated temperature for the indicated amount of time during which the alcohol generated by hydrolysis of the alkoxy silane groups and the alcohol solvent were both distilled off along with some of the water generated by the condensation of silanol groups which occurred as the polyalkoxysilane (PAOS) is generated. The reaction flask is cooled to room temperature and placed on a rotary evaporator (Buchi Rotovapor R110), used in conjunction with a water bath and vacuum pump (Welch 1402 DuoSeal) to remove any remaining solvent. All reactant and reagent types and ratios, catalysts and ratios, and all reaction conditions (e.g. time and temperature) are detailed in Table 2.

In some samples, such as Samples AB and AC, further reaction was needed, identified as Step 2 in Table 2 below. In Step 2, the procedure as described above was repeated except with the product from the above described reaction as the starting material. All reactant and reagent types and ratios, catalysts and ratios, and all reaction conditions (e.g. time and temperature) are detailed in Table 2.

TABLE 1

| | | | Non-Hydrolytic Synthesis | | |
|---|---|---|---|---|---|
| Precursor ID | TAOS amount and ID | Reagent | Mole Ratio Reagent/ TAOS | Catalyst | Mole Ratio Catalyst/ TAOS |
| A | 50 g TMOS | Acetic Anhydride | 1 | Tetrakis(trimethylsiloxy)titanium | 0.3% |
| B | 50 g TEOS | Acetic Anhydride | 1 | Titanium Ethoxide | 0.3% |
| C | 50 g TEOS | Acetic Anhydride | 0.8 | Titanium Butoxide | 0.3% |
| D | 50 g TEOS | Acetic Anhydride | 1 | Titanium Butoxide | 0.3% |
| E | 50 g TEOS | Acetic Anhydride | 1 | Titanium Butoxide | 0.15% |
| F | 50 g TEOS | Acetic Anhydride | 1.2 | Titanium Butoxide | 0.3% |
| G | 50 g TEOS | Acetic Anhydride | 0.7 | Tetrakis(trimethylsiloxy)titanium | 0.3% |
| H | 50 g TEOS | Acetic Anhydride | 0.8 | Tetrakis(trimethylsiloxy)titanium | 0.3% |
| I | 50 g TEOS | Acetic Anhydride | 0.9 | Tetrakis(trimethylsiloxy)titanium | 0.3% |
| J | 50 g TEOS | Acetic Anhydride | 1 | Tetrakis(trimethylsiloxy)titanium | 0.3% |
| K | 50 g TEOS | Acetic Anhydride | 1.2 | Tetrakis(trimethylsiloxy)titanium | 0.3% |
| L | 50 g TEOS/ 37.2 g TMOS | Acetic Anhydride | 1:1:2 (TEOS:TMOS:AA) | Tetrakis(trimethylsiloxy)titanium | 0.3% |
| M | 50 g TBOS | Acetic Anhydride | 1 | Tetrakis(trimethylsiloxy)titanium | 0.3% |
| N | 50 g TBOS | Acetic Anhydride | 1.2 | Tetrakis(trimethylsiloxy)titanium | 0.3% |
| O | 50 g TEOS/ 5 g TEMS | Acetic Anhydride | 1 | Tetrakis(trimethylsiloxy)titanium | 0.3% |
| P | 50 g TEOS/ 5 g DEDMS | Acetic Anhydride | 1 | Tetrakis(trimethylsiloxy)titanium | 0.3% |
| R | 50 g TEOS/ 2 g TMES | Acetic Anhydride | 1 | Tetrakis(trimethylsiloxy)titanium | 0.3% |
| S | 50 g TEOS/ 10 g TTB | Acetic Anhydride | 1 | None | n/a |
| AV | 50 g TEOS/ 20 g TTB | Acetic Anhydride | 1 | None | n/a |
| AWchange | 75 g TEOS | Acetic Anhydride | 1 | Tetrakis(trimethylsiloxy)titanium | 0.3% |
| AX | 1,000 g TEOS | Acetic Anhydride | 1 | Tetrakis(trimethylsiloxy)titanium | 0.3% |
| AY | 200 g TEOS | Acetic Anhydride | 1 | Tetrakis(trimethylsiloxy)titanium | 0.3% |
| AZ | 350 g TEOS | Acetic Anhydride | 1.1 | Tetrakis(trimethylsiloxy)titanium | 0.3% |
| AAA | 750 g TEOS | Acetic Anhydride | 1 | Tetrakis(trimethylsiloxy)titanium | 0.3% |
| AAC | 150 g TEOS | Acetic Anhydride | 1.2 | Titanium Tetraethoxide | 0.3% |
| AAD | 200 g TEOS | Acetic Anhydride | 1.2 | Tetrakis(trimethylsiloxy)titanium | 0.3% |

TABLE 1-continued

| Precursor ID | Temp. Profile | Physical Appearance | Degree of Branching | Mw*** | PDI |
|---|---|---|---|---|---|
| A | 50° C. for 1 hour then ramp to 100° C. for 1 hour | Sand | n/a* | n/a* | n/a* |
| B | 135° C. for 8 hours | Liquid | 0.18 | 1 | 1.7 |
| C | 135° C. for 8 hours | Liquid | 0.22 | 1.6 | 1.7 |
| D | 135° C. for 8 hours | Viscous Liquid | 0.27 | 3.3 | 2.9 |
| E | 135° C. for 8 hours | Viscous Liquid | 0.26 | 3.9 | 3.7 |
| F | 135° C. for 8 hours | Viscous Liquid | 0.30 | 7.2 | 4.6 |
| G | 135° C. for 8 hours | Liquid | 0.14 | 0.5 | 2.2 |
| H | 135° C. for 8 hours | Liquid | 0.10 | 1.1 | 1.2 |
| I | 135° C. for 8 hours | Liquid | 0.20 | 0.9 | 2.5 |
| J | 135° C. for 24 hours | Viscous Liquid | 0.26 | 2.3** | 2.1** |
| K | 135° C. for 24 hours | Viscous Liquid | 0.39 | 3.7 | 5.6 |
| L | 70° C. for 1 hour then ramp to 120° C. for 2 hours | Soft Gel Balls | n/a* | n/a* | n/a* |
| M | 130° C. for 1 hour then ramp to 180° C. for 24 hours | Viscous Liquid | 0.31 | 1.7 | 1.3 |
| N | 130° C. for 1 hour then ramp to 180° C. for 24 hours | Viscous Liquid | 0.47 | 2.5 | 1.4 |
| O | 135° C. for 24 hours | Liquid | 0.20 | 0.9 | 3.1 |
| P | 135° C. for 24 hours | Viscous Liquid | 0.26 | 1.2 | 3.1 |
| R | 135° C. for 24 hours | Viscous Liquid | 0.26 | 1.3 | 3.0 |
| S | 135° C. for 24 hours | Viscous Liquid | 0.24 | 0.9 | 3.2 |
| AV | 135° C. for 24 hours | Viscous Liquid | 0.27 | 1.4 | 2.4 |
| AWchange | 135° C. for 7 hours | Viscous Liquid | 0.25 | 1.8 | 2.0 |
| AX | 135° C. for 28 hours | Viscous Liquid | 0.26 | 1.2 | 3.9 |

TABLE 1-continued

| | | | | | |
|---|---|---|---|---|---|
| AY | 135° C. for 24 hours | Viscous Liquid | 0.25 | 1.3 | 3.9 |
| AZ | 135° C. for 30 hours | Viscous Liquid | 0.29 | 1.5 | 4.9 |
| AAA | 135° C. for 24 hours | Viscous Liquid | 0.26 | 1.4 | 1.8 |
| AAC | 135° C. for 24 hours | Viscous Liquid | 0.36 | 3.8 | 7.4 |
| AAD | 135° C. for 60 hours | Viscous Liquid | 0.43 | 10 | 6.6 |

*Samples past gel point. Characterization data not available, **Results are an average of three synthesized materials
*** Polystyrene equivalent Weight Average Molecular Weight calculated as described above

TABLE 2

Hydrolytic Synthesis

| Precursor ID | TAOS amount and ID | Reagent/ Catalyst | Mole Ratio Reagent/ Catalyst/ TAOS | Solvent Amount and ID | Temp. Profile | Step 2 Reagent/ Catalyst | Additional Moles Reagent/ Catalyst Added | Solvent | Temp. Profile Step 2 | Physical Appearance | Degree of Branching | MW (kDa) | PDI |
|---|---|---|---|---|---|---|---|---|---|---|---|---|---|
| U | 50 g TMOS | H$_2$O/0.1N HCl | 0.5/ 0.00216/1 | 65 mL MeOH | 70° C. for 1 hour then ramp to 115° C. for 7 hours | — | — | — | — | Liquid | 0.07 | < LOD | — |
| V | 50 g TMOS | H$_2$O/0.1N HCl | 1/ 0.00433/1 | 65 mL MeOH | 70° C. for 1 hour, ramp 115° C. for 7 hrs, then reduce back to 70° C. for 16 hours | — | — | — | — | Liquid | 0.21 | 0.1 | 4.4 |
| W | 50 g TMOS | H$_2$O/0.1N HCl | 1.25/ 0.00541/1 | 65 mL MeOH | 70° C. for 1 hour then ramp to 115° C. for 7 hours | — | — | — | — | Viscous Liquid | 0.30 | 3.3 | 1.3 |
| X | 50 g TMOS | H$_2$O/0.1N HCl | 1.5/ 0.00650/1 | 65 mL MeOH | 70° C. for 1 hour then ramp to 115° C. for 7 hours | — | — | — | — | Gel | n/a* | n/a* | n/a* |
| Y | 50 g TEOS | H$_2$O/0.1N HCl | 0.61/ 0.00264/1 | 60 mL EtOH | 80° C. for 1 hour, ramp 120° C. for 7, then reduce back to 80° C. for 60 hours | — | — | — | — | Liquid | 0.20 | 1.4 | 1.3 |
| Z | 50 g TEOS | H$_2$O/0.1N HCl | 1/ 0.00433/1 | 60 mL EtOH | 80° C. for 1 hour then ramp to 120° C. for 24 hours | — | — | — | — | Liquid | 0.11 | 0.6 | 1.2 |
| AA | 50 g TEOS | H$_2$O/1.0N HCl | 0.61/ 0.0264/1 | 60 mL EtOH | 80° C. for 1 hour then ramp to 120° C. for 7 hours | — | — | — | — | Liquid | 0.14 | 0.7 | 1.1 |
| AB | 50 g TEOS | H$_2$O/1.0N HCl | 0.5/ 0.0287/1 | 60 mL EtOH | 80° C. for 1 hour then ramp to 120° C. for 7 hours | H$_2$O/ 1.0N HCl | 0.11/0.0835 | 60 mL EtOH | 80° C. for 1 hour then ramp to 120° C. for 7 hours | Liquid | 0.21 | < LOD | — |

TABLE 2-continued

Hydrolytic Synthesis

| Precursor ID | TAOS amount and ID | Reagent/ Catalyst | Mole Ratio Reagent/ Catalyst/ TAOS | Solvent Amount and ID | Temp. Profile | Step 2 Reagent/ Catalyst | Additional Moles Reagent/ Catalyst Added | Solvent | Temp. Profile Step 2 | Physical Appearance | Degree of Branching | MW (kDa) | PDI |
|---|---|---|---|---|---|---|---|---|---|---|---|---|---|
| AC | 50 g TEOS | $H_2O$/ 0.002N HCl | 0.5/ $4.33^{E-5}$/1 | 60 mL EtOH | 80° C. for 1 hour then ramp to 120° C. for 7 hours | $H_2O$/ 0.002N HCl | $0.11/9.5^{E-6}$ | 60 mL EtOH | 80° C. for 1 hour then ramp to 120° C. for 7 hours | Viscous Liquid | 0.25 | 3.7 | 2.8 |
| AD | 50 g TEOS | $H_2O$/Acetic Acid | 1/1/1 | 50 mL EtOH | 80° C. for 1 hour then ramp to 120° C. for 24 hours | — | — | — | — | Viscous Liquid | 0.32 | 3.5 | 1.7 |
| AE | 50 g TEOS | $H_2O$/Acetic Acid | 1.5/1.5/1 | 50 mL EtOH | 80° C. for 1 hour then ramp to 120° C. for 24 hours | — | — | — | — | Sand | n/a* | n/a* | n/a* |
| AF | 50 g TEOS/ | $H_2O$/0.1N HCl | 1/ 0.00433/1 | 60 mL MeOH | 65° C. for 1 hour then ramp to 100° C. for 7 hours | — | — | — | — | Liquid | 0.13 | 0.4 | 1.6 |
| AG | 50 g TEOS/ 50g STC | $H_2O$ | 1/0/1 | 62 mL EtOH | 80° C. for 1 hour then ramp to 120° C. for 24 hours | — | — | — | — | Viscous Liquid | 0.27 | 0.6 | 1.3 |
| AH | 50 g TEOS/ 0.5 g TEMS | $H_2O$/0.1N HCl | 1/ 0.00433/1 | 56 mL EtOH | 80° C. for 1 hour then ramp to 120° C. for 24 hours | — | — | — | — | Liquid | 0.20 | 0.6 | 1.4 |
| AI | 50 g TEOS/ 5 g TEMS | $H_2O$/0.1N HCl | 1/ 0.00433/1 | 62 mL EtOH | 80° C. for 1 hour then ramp to 120° C. for 24 hours | — | — | — | — | Liquid | 0.11 | 0.7 | 1.4 |
| AK | 50 g TBOS | $H_2O$/0.1N HCl | 0.8/ 0.00433/1 | 45 mL EtOH | 80° C. for 1 hour then ramp to 180° C. for 65 hours | — | — | — | — | Liquid | 0.11 | 0.7 | 1.2 |
| AL | 50 g TBOS | $H_2O$/0.1N HCl | 1/ 0.00433/1 | 45 mL EtOH | 80° C. for 1 hour then ramp to 180° C. for 65 hours | — | — | — | — | Liquid | 0.15 | 0.9 | 1.4 |
| AM | 50 g TEOS | Formic Acid | 1.2/0/1 | n/a | 80° C. for 1 hour then ramp to 120° C. for 24 hours | — | — | — | — | Viscous Liquid | 0.27 | 0.9 | 7.1 |
| AN | 50 g TEOS | $H_2O$/ Formic Acid | 1/1/1 | 70 mL EtOH | 80° C. for 1 hour then ramp to 120° C. for 6 hours | — | — | — | — | Gelled | n/a* | n/a* | n/a* |
| AO | 50 g TEOS | $H_2O$/ Trifluoro Acetic Acid | 1/0.5/1 | 70 mL EtOH | 80° C. for 1 hour then ramp to 120° C. for 24 hours | — | — | — | — | Liquid | 0.15 | 0.9 | 2.9 |
| AP | 45 g TEOS/ 5 g TAcS | $H_2O$ | 1/ 0.00433/1 | 62 mL EtOH | 80° C. for 1 hour then ramp to 120° C. for 24 hours | — | — | — | — | Viscous Liquid | 0.21 | 0.9 | 1.6 |

TABLE 2-continued

Hydrolytic Synthesis

| Precursor ID | TAOS amount and ID | Reagent/ Catalyst | Mole Ratio Reagent/ Catalyst/ TAOS | Solvent Amount and ID | Temp. Profile | Step 2 Reagent/ Catalyst | Additional Moles Reagent/ Catalyst Added | Solvent | Temp. Profile Step 2 | Physical Appearance | Degree of Branching | MW (kDa) | PDI |
|---|---|---|---|---|---|---|---|---|---|---|---|---|---|
| AQ | 45 g TEOS/ 5 g TEMS | H$_2$O/0.1N HCl | 1/ 0.00433/1 | 56 mL EtOH | 80° C. for 1 hour then ramp to 120° C. for 24 hours | — | — | — | — | Liquid | 0.11 | 0.5 | 1.3 |
| AR | 45 g TEOS/ 5 g DEDMS | H$_2$O/0.1N HCl | 1/ 0.00433/1 | 58 mL EtOH | 80° C. for 1 hour then ramp to 120° C. for 24 hours | — | — | — | — | Liquid | 0.10 | 0.5 | 1.3 |
| AS | 48 g TEOS/ 2 g TMES | H$_2$O/0.1N HCl | 1/ 0.00433/1 | 55 mL EtOH | 80° C. for 1 hour then ramp to 120° C. for 24 hours | — | — | — | — | Liquid | 0.10 | 0.6 | 1.4 |
| AT | 90 g TEOS/ 8 g TEMS/ 2 g TMES | H$_2$O/0.1N HCl | 1/ 0.00433/1 | 114 mL EtOH | 80° C. for 1 hour then ramp to 120° C. for 24 hours | — | — | — | — | Viscous Liquid | 0.23 | 0.8 | 1.5 |
| AU | 50 g TEOS/ 10 g TTB | H$_2$O/0.1N HCl | 1/ 0.00433/1 | 60 mL EtOH | 80° C. for 1 hour then ramp to 120° C. for 24 hours | — | — | — | — | Viscous Liquid | 0.26 | 1.1 | 3.1 |
| AAB | 20 g TEOS | Glacial Acetic Acid | 2/0/1 | 0 mL | 80° C. for 1 hour then ramp to 120° C. for Viscous 24 hours | — | — | — | — | Liquid | 0.16 | 0.6 | 2.3 |

*Samples past gel point. Characterization data not available

Example 3: Oil-in-Water Capsules

Capsules of Table 3, section A (Samples C, E, F, G, H, I, J, K, L, Q, S, T, Z, AA, AB, AC and comparative example W) were made by the following method:

The oil phase was prepared by mixing and homogenizing (or even dissolving if all compounds are miscible) a precursor with a benefit agent and/or a core modifier. The water phase was prepared by adding acids or bases to water to yield a desired starting pH. Next, nanoparticles were added to the water phase and dispersed with an ultrasound bath for at least 30 minutes.

Once each phase was prepared separately, they were combined, and the oil phase was dispersed into the water phase with proper mixing tools, times and energy to reach a desired mean capsule diameter of the capsules. If not specified otherwise, once the emulsification step was complete, the resulting emulsion was left resting without stirring at a specific temperature until enough curing had occurred for the capsules to not collapse. Optionally, in order to deposit a second shell component, the capsules could receive a post-treatment with a second shell component solution, with materials and quantities described in Table 3.

To test whether capsules collapse, the slurry must be at least 10 times diluted into de-ionized water. Drops of the subsequent dilution were added onto a microscopy microslide and left to dry overnight at room temperature. The following day the dried capsules were observed under an optical microscope by light transmission to assess if the capsules have retained their spherical shape (without the use of a cover slide)

All reagent types and ratios, and all reaction conditions (e.g. mixing, curing time and temperature) are detailed in Table 3 and the results are detailed in Table 4. All results were tested or measured in accordance with the test methods set forth herein.

Figure 2A:
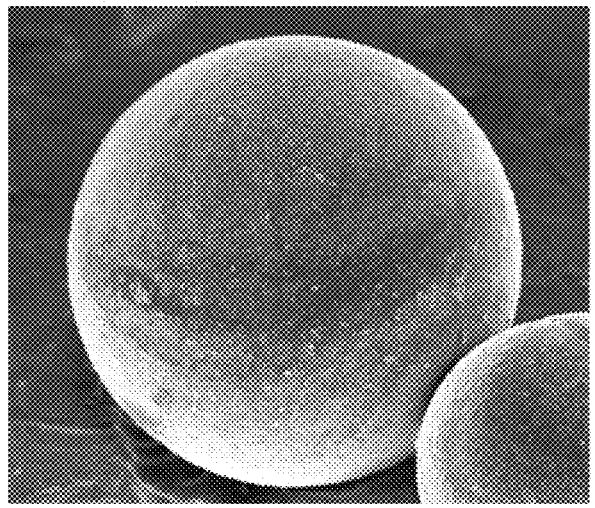
FIG. 2A is a scanning electron microscopy image of a capsule of sample Q in accordance with embodiments of the disclosure.
Figure 2B:
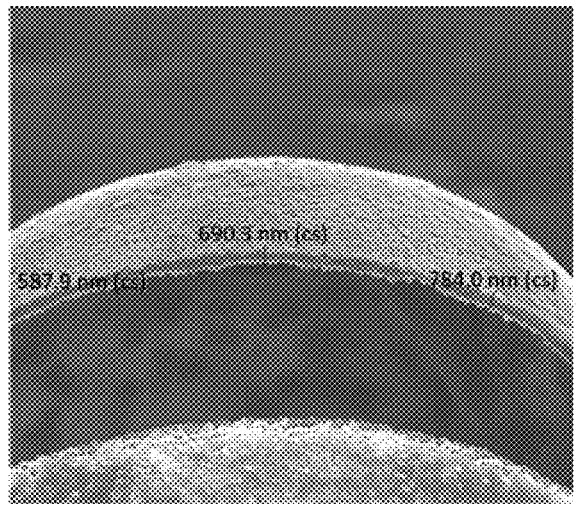
FIG. 2B is a scanning electron microscopy image of a capsule shell of Sample Q in accordance with embodiments of the disclosure.
Figure 3A:
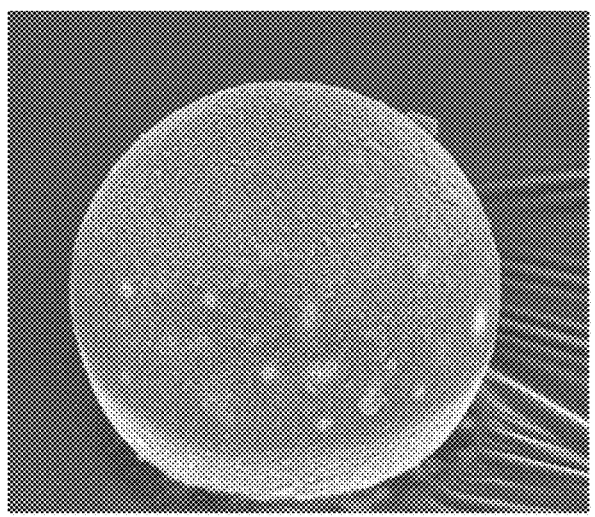
FIG. 3A is a scanning electron microscopy image of a capsule of Sample I in accordance with embodiments of the disclosure, illustrating an unbroken the capsule shell.
Figure 3B:
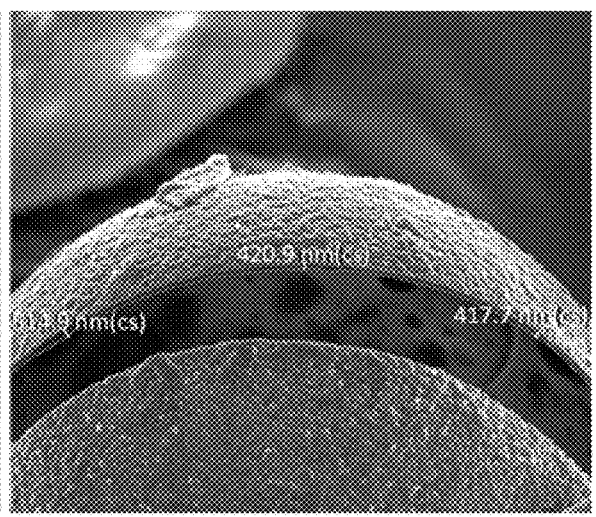
FIG. 3B is a scanning electron microscopy image of a cross-section of a capsule of Sample I in accordance with embodiments of the disclosure, illustrating a capsule shell.
Figure 6:
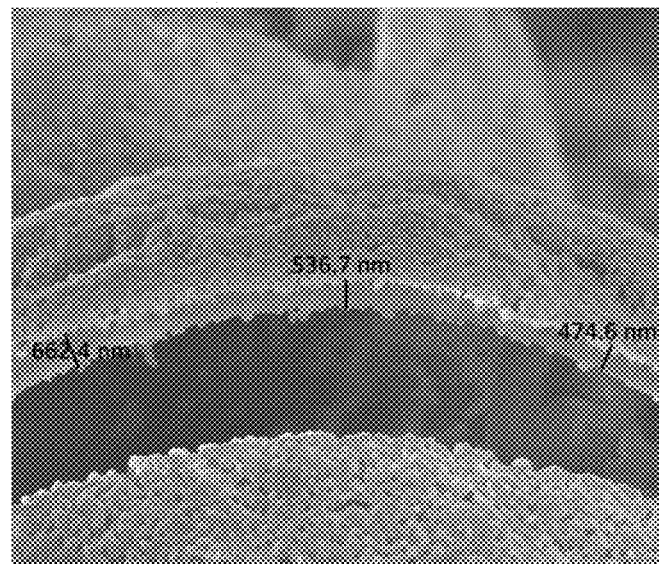
FIG. 6 is a scanning electron microscopy image of a capsule shell of Sample Z in accordance with embodiments of the disclosure.
Figure 7A:
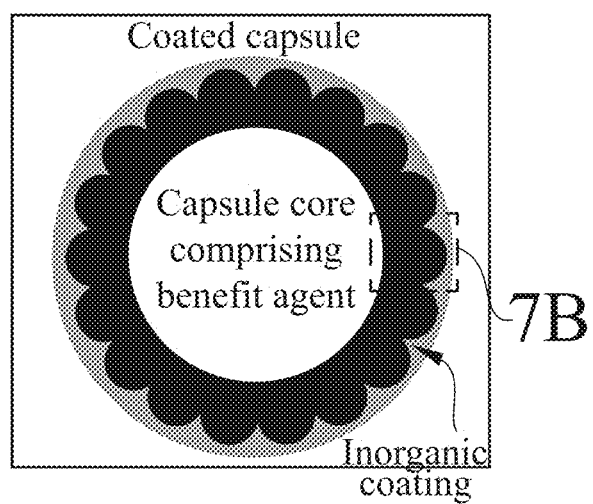
FIG. 7A is a schematic illustration of a process of forming the second shell component in accordance with embodiments of the disclosure.
Figure 7B:
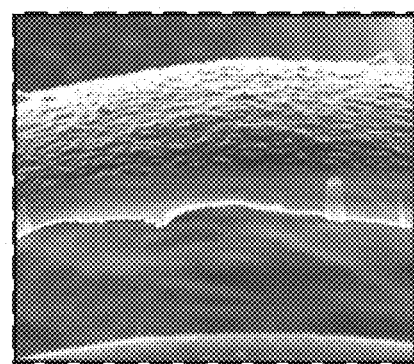
FIG. 7B is scanning electron microscopy images of capsules of Sample G in accordance with embodiments of the disclosure, after the process illustrated in FIG. 7A
Figure 10:
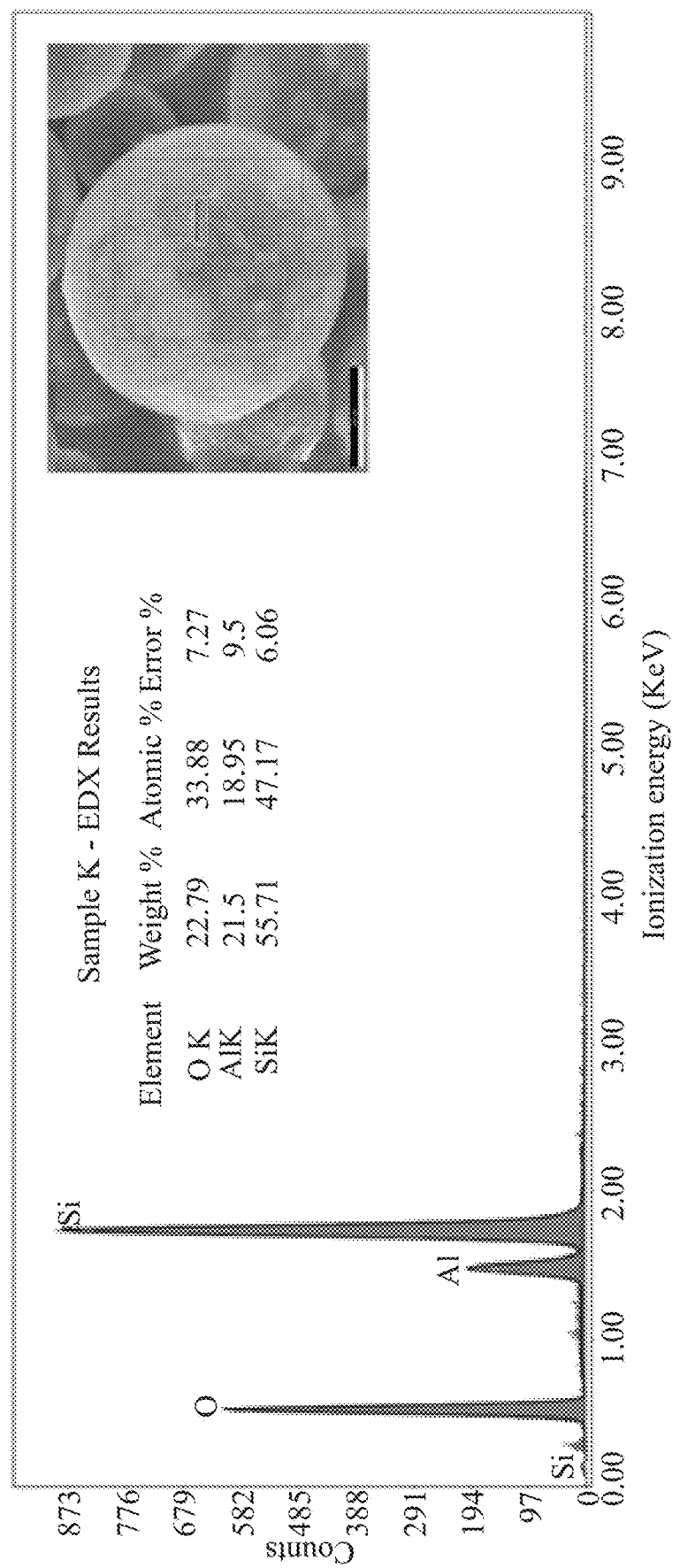
FIG. 10 is an energy dispersive X-ray spectrum of a capsule of Sample K in accordance with embodiments of the disclosure.
Figure 11:
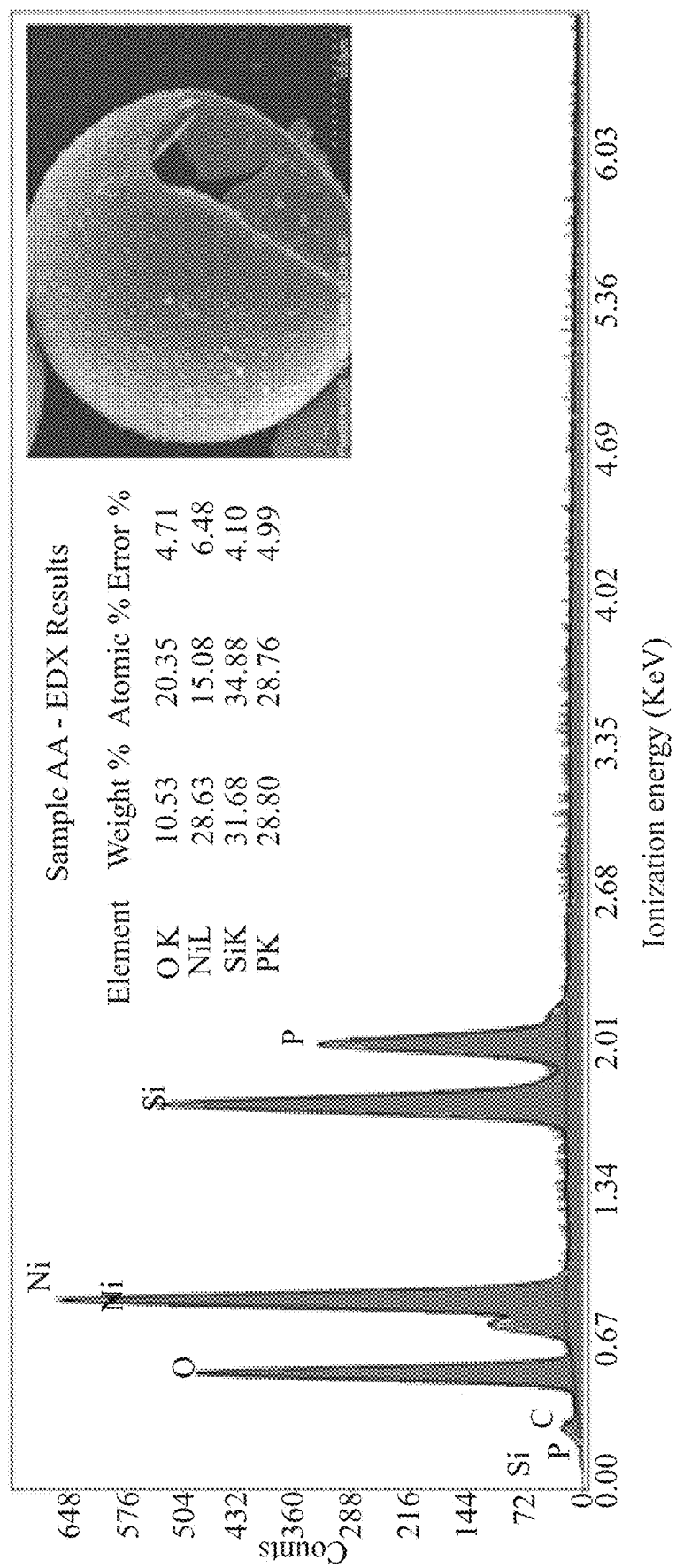
FIG. 11 is an energy dispersive X-ray spectrum of a capsule of Sample AA in accordance with embodiments of the disclosure.

FIG. 2A illustrates a capsule of Sample Q and FIG. 2B illustrates a capsule shell of Sample Q, of Table 3 and 4. FIG. 3A illustrates an unbroken capsule of Sample I and FIG. 3B illustrates a capsule shell of Sample I, of Table 3 and 4. FIG. 4A illustrates capsules of Sample E and FIG. 4B illustrates a capsule shell of Sample E, of Table 3 and 4. FIG. 5 illustrates capsules of Sample C of Table 3 and 4. FIG. 6 illustrates a capsule shell of Sample Z of Table 3 and 4. FIGS. 7A-B illustrate capsules having a substantially inorganic shell comprising a first shell component and a second shell component of Sample G of Table 3 and 4. FIG. 8A illustrates capsules having a substantially inorganic shell comprising a first shell component and a second shell component of Sample H and FIG. 8B illustrates a capsule shell having a substantially inorganic shell comprising a first shell component and a second shell component of Sample H, of Table 3 and 4 and FIG. 9 illustrates collapsing capsule shells of Sample W, of Table 3 and 4. FIG. 10 illustrates an energy dispersive X-ray spectrum of a capsule of Sample K and FIG. 11 illustrates an energy dispersive X-ray spectrum of a capsule of Sample AA of Tables 3 and 4.

Example 4: Water-in-Oil Capsules

Capsules of Table 3, Section A (Examples N and AD) were made by the following method:

The water phase was prepared by mixing and homogenizing any combination of the following and at least a benefit agent: water, core modifier, benefit agent and nanoparticles. The oil phase consisted of a large excess of a hydrophobic liquid as the continuous phase. The oil phase can be a solvent or any liquid organic molecule that is substantially immiscible with water. The oil phase included the nanoparticles, which were well dispersed into the above hydrophobic liquid for at least 30 minutes in an ultrasound bath. The continuous oil phase included the metal oxide precursor prior to or after emulsification, as well as an organic acid prior to or after emulsification.

Once each phase was prepared separately, they were combined, and the water phase was dispersed into the oil phase with proper mixing tools, times and energy to reach a desired mean diameter of the capsules. If not specified otherwise, once the emulsification step was complete, the resulting emulsion was left resting without stirring at a specific temperature until enough curing has occurred for the capsules to not collapse. Optionally, in order to deposit a second shell component, the capsules could receive a post-treatment with a second shell component solution, with materials and quantities described in Table 3.

To test whether capsules collapse, the slurry must be at least 10 times diluted into de-ionized water. Drops of the subsequent dilution were added onto a microscopy microslide and left to dry overnight at room temperature. The following day the dried capsules were observed under an optical microscope by light transmission to assess if the capsules have retained their spherical shape (without the use of a cover slide).

All reagent types and ratios, and all reaction conditions (e.g. mixing, curing time and temperature) are detailed in Table 3 and the results are detailed in Table 4. All results were tested or measured in accordance with the test methods set forth herein.

Figure 12A:
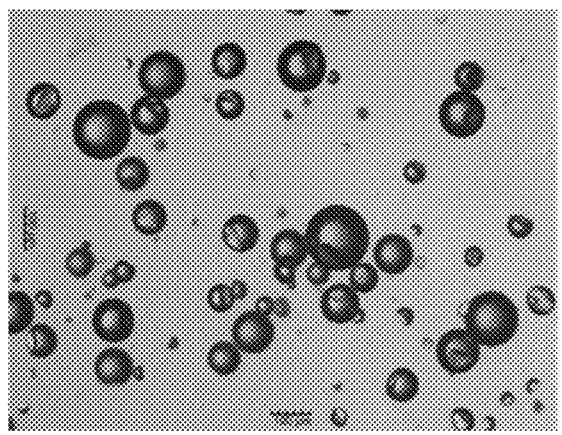
FIG. 12A is an optical microscopy image of capsules of Sample N in accordance with embodiments of the disclosure prepared using a hydrophilic core.
Figure 12B:
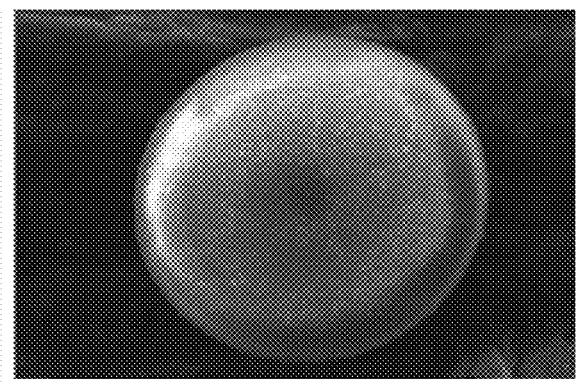
FIG. 12B is a scanning electron microscopy image of a capsule of Sample N in accordance with embodiments of the disclosure prepared using a hydrophilic core.

FIGS. 12A and B illustrate capsules of Sample N, of Table 3 and 4.

Example 5: Oil-in-Water Capsules with Variable Shell Organic Percentage

Capsule of Table 3 section B (Examples AF, AH, AJ and comparative examples AE, AG, AK, AL, AI, AM, AN, AO, AP) were made by the following method:

The oil phase was prepared by mixing and homogenizing (or even dissolving if all compounds are miscible) a precursor with a benefit agent and/or a core modifier. The water phase was prepared by adding acids or bases to water to yield a desired starting pH. Next, nanoparticles were added to the water phase and dispersed with an ultrasound bath for at least 30 minutes.

Once each phase was prepared separately, they were combined, and the oil phase was dispersed into the water phase with proper mixing tools, times and energy to reach a desired mean capsule diameter of the capsules. If not specified otherwise, once the emulsification step was complete, the resulting emulsion was left resting without stirring at a specific temperature until enough curing had occurred for the capsules to not collapse. Optionally, in order to deposit a second shell component, the capsules could receive a post-treatment with a second shell component solution, with materials and quantities described in Table 3.

To test whether the capsules collapse, the slurry must be at least 10 times diluted into de-ionized water. Drops of the subsequent dilution were added onto a microscopy microslide and left to dry overnight at room temperature. The following day the dried capsules were observed under an optical microscope by light transmission to assess if the capsules have retained their spherical shape (without the use of a cover slide)

All reagent types and ratios, and all reaction conditions (e.g. mixing, curing time and temperature) are detailed in Table 3 and the results are detailed in Table 4. All results were tested or measured in accordance with the test methods set forth herein.

Figure 13:
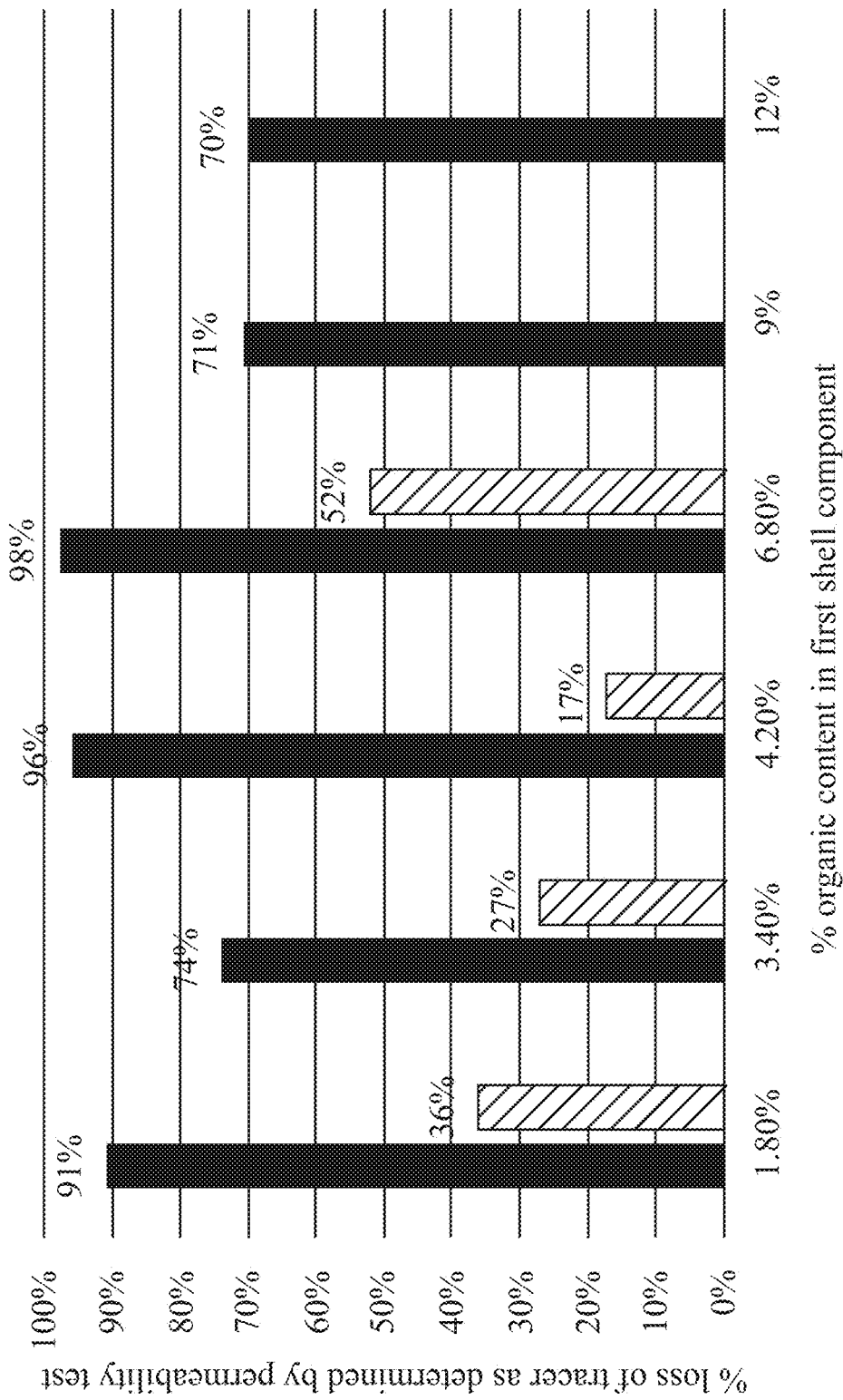
FIG. 13 is a graph of the loss percentage of tracer as determined by the permeability method against to the organic percentage content in the first shell component in accordance with embodiments of the disclosure.

Section B of Tables 3 and 4 (making of capsules and results respectively) shows that capsules with an increasing percentage of organic content in the first shell component have increased permeabilities after addition of a second shell component as illustrated by FIG. 13. With first shell components only, the permeability is high, but the capsule can resist air drying without collapsing.

Example 6: Oil-in-Water Capsules with Variable Core/Shell Ratio Values

Capsule of Table 3 section C (Examples AU, AV and comparative examples B, AQ, AR, AS, AT, AW) were made by the following method:

The oil phase was prepared by mixing and homogenizing (or even dissolving if all compounds are miscible) a precursor with a benefit agent and/or a core modifier. The water phase was prepared by adding acids or bases to water to yield a desired starting pH. Next, nanoparticles were added to the water phase and dispersed with an ultrasound bath for at least 30 minutes.

Once each phase was prepared separately, they were combined, and the oil phase was dispersed into the water phase with proper mixing tools, times and energy to reach a desired mean capsule diameter of the capsules. If not specified otherwise, once the emulsification step was complete, the resulting emulsion was left resting without stirring at a specific temperature until enough curing had occurred for the capsules to not collapse. Optionally, in order to deposit a second shell component, the capsules could receive a post-treatment with a second shell component solution, with materials and quantities described in Table 3.

To test whether capsules collapse, the slurry must be at least 10 times diluted into de-ionized water. Drops of the subsequent dilution were added onto a microscopy microslide and left to dry overnight at room temperature. The following day the dried capsules were observed under an optical microscope by light transmission to assess if the capsules have retained their spherical shape (without the use of a cover slide)

All reagent types and ratios, and all reaction conditions (e.g. mixing, curing time and temperature) are detailed in Table 3 and the results are detailed in Table 4. All results were tested or measured in accordance with the test methods set forth herein.

Figure 14:
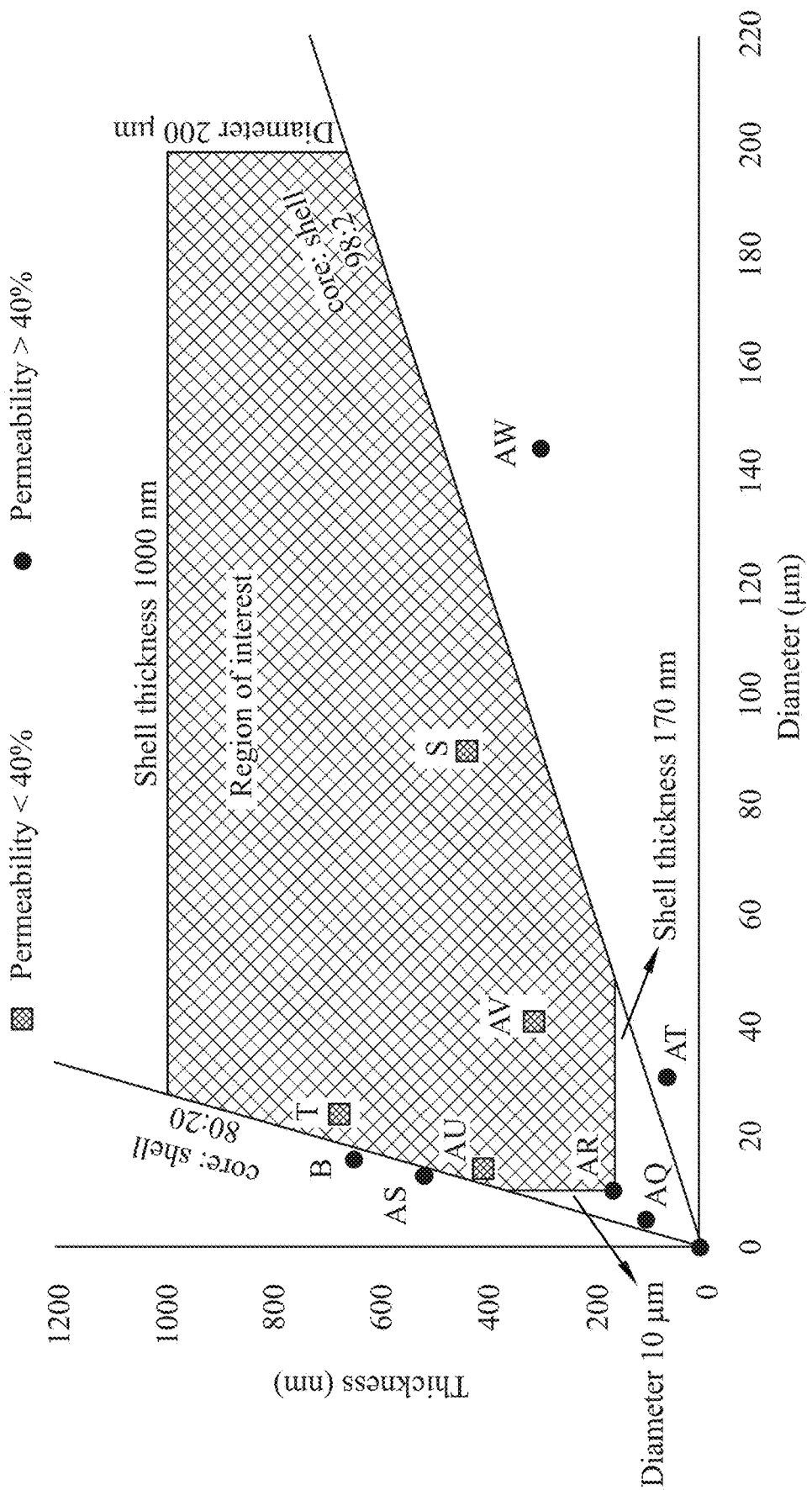
FIG. 14 is a graph of mean shell thickness against capsule mean volume weighted diameter in accordance with embodiments of the disclosure.

Examples from Table 3 section C demonstrate the importance of combining an optimal mean volume weighed capsule diameter (10 um-200 um), mean shell thickness (170 nm-1000 nm) and core shell ratio (80:20-98:2) as disclosed in this invention, in order to obtain low shell permeabilities in accordance with the shell permeability method. FIG. 14 illustrates the region of interest when plotting examples (permeability <40%) and comparative examples (permeability >40%). FIG. 15A illustrates a capsule shell of Sample B (comparative example) with a core shell ratio of 78:22 and FIG. 15B illustrates capsules of Sample B, of Table 3 and 4, FIG. 16 illustrates a capsule shell of Sample AW (comparative example) of Table 3 and 4 with a core:shell ratio of 99:1.

Example 7: Oil-in-Water Capsules Prepared with Variable First Shell Component Precursor Degree of Branching and Molecular Weight Capsule of Table 3 section D (Examples AAA, AAB, AAC and comparative examples AX, AY, AAD, AAE, AAF) were made by the following method:

The oil phase was prepared by mixing and homogenizing (or even dissolving if all compounds are miscible) a precursor with a benefit agent and/or a core modifier. The water phase was prepared by adding acids or bases to water to yield a desired starting pH. Next, nanoparticles were added to the water phase and dispersed with an ultrasound bath for at least 30 minutes.

Once each phase was prepared separately, they were combined, and the oil phase was dispersed into the water phase with proper mixing tools, times and energy to reach a desired mean capsule diameter of the capsules. If not specified otherwise, once the emulsification step was complete, the resulting emulsion was left resting without stirring at a specific temperature until enough curing had occurred for the capsules to not collapse. Optionally, in order to deposit a second shell component, the capsules could receive a post-treatment with a second shell component solution, with materials and quantities described in Table 3.

To test whether capsules collapse, the slurry must be at least 10 times diluted into de-ionized water. Drops of the subsequent dilution were added onto a microscopy microslide and left to dry overnight at room temperature. The following day the dried capsules were observed under an optical microscope by light transmission to assess if the capsules have retained their spherical shape (without the use of a cover slide)

All reagent types and ratios, and all reaction conditions (e.g. mixing, curing time and temperature) are detailed in Table 3 and the results are detailed in Table 4. All results were tested or measured in accordance with the test methods set forth herein.

Figure 17:
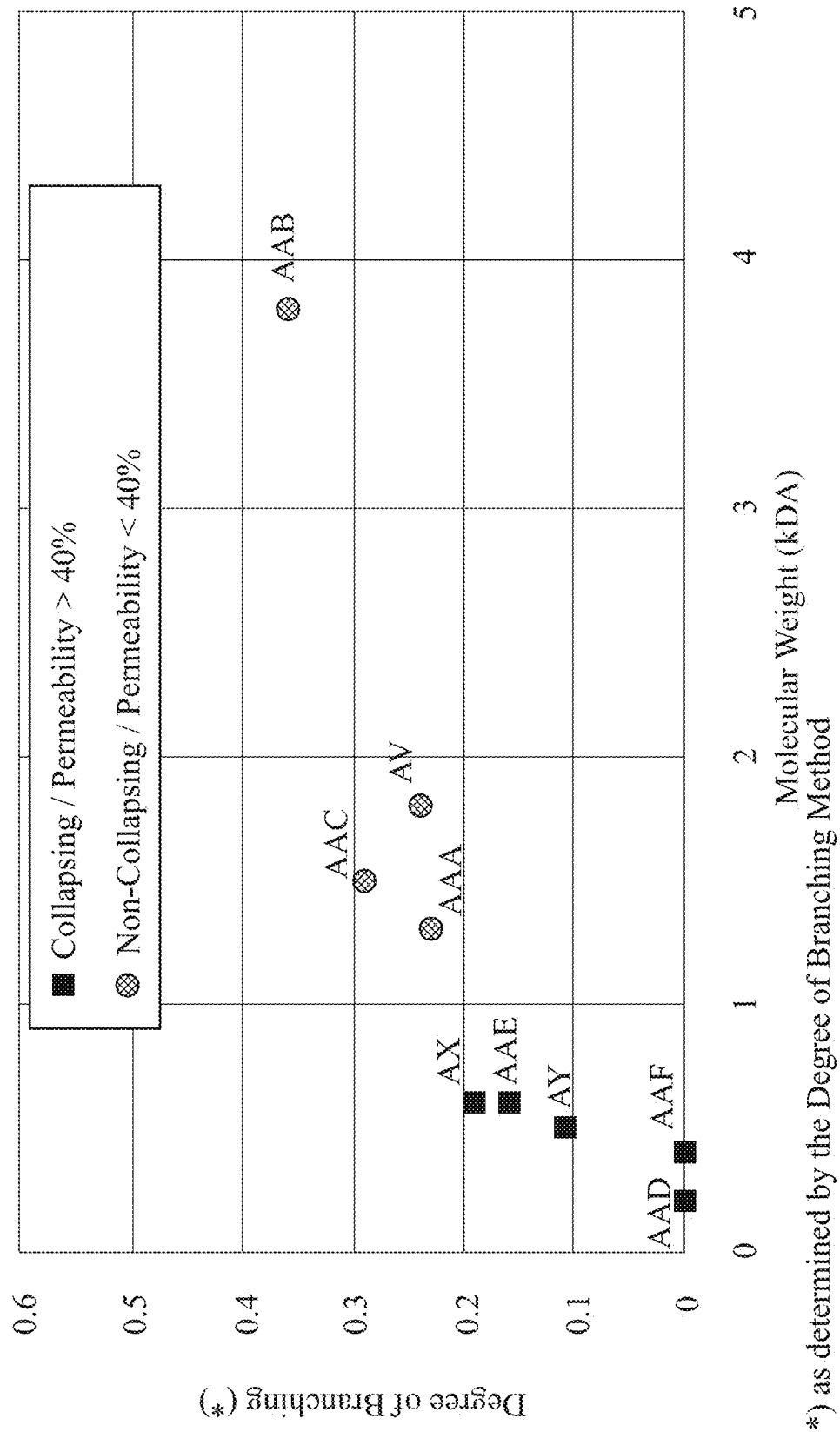
FIG. 17 is a graph of Degree of Branching against Molecular Weight in accordance with embodiments of the disclosure.

Capsule data in the Table 3 section D shows that capsules made with PAOS having a Degree of Branching below 0.2 and a Molecular weight below 700 Da present a shell permeability higher than 40% and/or do not resist air drying without collapsing as represented by the graph in FIG. 17.

By way of example, the following is a detailed description of the application of the Permeability Test Method to determine the shell permeability of capsules of example R from Tables 3 and 4 below.

Verdyl acetate was present at a level of 13 w % in the fragrance composition.

Capsule slurry obtained in example R from Table 3 had an oil activity of 19.04% based on the mass balance of the capsule making protocol. 0.131 g of this slurry was weighed into 9.87 g of a 15 w % SDS (aq.) solution to yield a product with an oil concentration of 0.249 w % and an SDS concentration of 14.53%. The resulting mixture was well dispersed by gently shaking the vial by hand in a circular motion. The glass vial was hermetically sealed with an airtight lid and stored at 35 degrees Celsius and 40% humidity for 7 days. The day of product making is considered as day 0. It was found that the actual Verdyl Acetate content in the sample was corresponding to the theoretical value.

On day 7, the reference sample was prepared by weighing 0.126 g of the oil used for the capsule making into 49.88 g of a 15 w % SDS (aq.) solution to yield a reference sample with an oil concentration of 0.252% and an SDS concentration of 14.96%. The resulting mixture was stirred with the aid of a magnetic stirrer in a sealed jar until complete solubilization of the oil. The reference sample was kept aside and stored at room temperature.

Prior to measurement, the product containing capsules was removed from storage. The capsules had settled to the bottom of the vial. The capsules were re-dispersed by gently shaking the vial in a circular motion, until the whole volume of liquid was turbid. Immediately after capsule re-dispersion, using a positive displacement pipette (from Eppendorf), 100 microL aliquots were inserted into the bottom of 3 separate headspace vials, and immediately sealed with a crimp cap.

The same operation was performed for the reference product.

After 3 hours of equilibration at room temperature, the first replicate of reference product containing vial was measured via headspace GC/MS as outlined in the test methods section. Once the GC oven had cooled down to the starting temperature, the next replicate was immediately measured, and so on until all replicates of references and capsules containing products have been analyzed.

The ion chromatogram for M/Z of 66 was extracted, the peaks corresponding to Verdyl acetate and its isomers were identified by reading the full mass spectra and comparing to literature. These identified peaks were then integrated to yield an Area under the peaks. An average of the areas of the 3 replicates was made for the reference and capsule samples respectively (Table A below):

TABLE A

| ID | AREA UNDER PEAK |
| --- | --- |
| REFERENCE_1 | 71714 |
| REFERENCE_2 | 74537 |
| REFERENCE_3 | 73447 |
| CAPSULE_1 | 49225 |
| CAPSULE_2 | 46713 |
| CAPSULE_3 | 53256 |

Average Area for reference was 73233 and the average Area for the capsule containing product was 49731, based on the table above.

$$\frac{\text{Verdyl Acetate Area Count for sample containing capsules}}{\text{Verdyl Acetate Area Count for Reference Sample}} *$$

$$\frac{100\%}{\% \text{ Actual } V\text{Berdyl Acetate vs. theoretical Verdyl Acetate}} *$$

$$\frac{\text{oil \% reference}}{\text{oil \% sample}} = \frac{49731}{73233} * \frac{100\%}{100\%} * \frac{0.252\%}{0.249\%} = 68.7\%$$

shell permeability for Verdyl acetate after 7 days of storage at 35 degrees Celsius and 40% relative humidity.

TABLE 3

Examples capsule preparation
Section A

| Sample ID | Emulsion | Oil phase | Precursor (Tables 1-4) | Water phase | Emulsification | Curing temp. (° C.) | Second shell component solution material and quantity |
|---|---|---|---|---|---|---|---|
| F | Oil in water | 1.2 g fragrance oil and 0.8 g precursor | K | 8 g of a 1.75w % Aerosil 300 dispersion in 0.1M HCl | 5 min. at 8000rpm (IKA ultraturrax S25N-10G) | d | 1 g of 10w % of Sodium silicate(aq.) solution. Conditions e |
| G | Oil in water | 1.6 g fragrance oil and 0.4 g precursor | J | 8 g of a 0.4w % Aerosil 300 dispersion in 0.1M HCl | 5 min. at 8000rpm (IKA ultraturrax S25N-10G) | d | 1.5 g of 10w % of Sodium silicate(aq.) solution. Conditions e |
| H | Oil in water | 1.6 g fragrance oil and 0.4 g precursor | J | 8 g of a 0.4w % Aerosil 300 dispersion in 0.1M HCl | 5 min. at 8000rpm (IKA ultraturrax S25N-10G) | d | 1.5 g of TEOS. Conditions e |
| L | Oil in water | 1.6 g MML(a) and 0.4 g precursor | J | 8 g of a 0.4w % Aerosil 300 dispersion in 0.1M HCl | 5 min. at 8000rpm (IKA ultraturrax S25N-10G) | d | 0.9 g of 5.4w % of Sodium silicate(aq.) solution. Conditions e |
| Q | Oil in water | 2 g fragrance oil and 0.5 g precursor | M | 8 g of a 1.75w % Aerosil 300 dispersion in 0.1M HCl | 5 min. at 8000rpm (IKA ultraturrax S25N-10G) | d | 0.9 g of 5.4w % of Sodium silicate(aq.) solution. Conditions e |
| S | Oil in water | 20 g fragrance oil and 5 g precursor | J | 80 g of a 2.5w % Aerosil 300 dispersion in 0.1M HCl | 5 min. at 1400rpm (IKA R1342 Propeller 4 bladed) | c | 0.9 g of 5.4w % of Sodium silicate(aq.) solution. Conditions e |
| T | Oil in water | 4 g fragrance oil and 1 g precursor | J | 16 g of a 2.5w % Aerosil 300 dispersion in 0.1M HCl | 5 min. at 8000rpm (IKA ultraturrax S25N-10G) | c | 0.9 g of 5.4w % of Sodium silicate(aq.) solution. Conditions e |
| Z | Oil in water | 1.2 g fragrance oil and 0.8 g precursor | M | 8 g of a 1.75w % Aerosil 300 dispersion in 0.1M HCl | 5 min. at 8000rpm (IKA ultraturrax S25N-10G) | c | 0.9 g of 5.4w % of Sodium silicate(aq.) solution. Conditions e |
| C | Oil in water | 1.6 g MML(a) and 0.4 g precursor | J | 8 g of a 0.4w % Aerosil 300 dispersion in 0.1M HCl | 5 min. at 8000rpm (IKA ultraturrax S25N-10G) | d | No second shell component |
| E | Oil in water | 1.2 g fragrance oil and 0.8 g precursor | J | 8 g of a 1.75w % Aerosil 300 dispersion in 0.1M HCl | 5 min. at 8000rpm (IKA ultraturrax S25N-10G) | d | No second shell component |
| I | Oil in water | 2 g isopropyl myristate and 0.5 g precursor | J | 8 g of a 1.75w % Aerosil 300 dispersion in 0.1M HCl | 5 min. at 8000rpm (IKA ultraturrax S25N-10G) | d | No second shell component |
| J | Oil in water | 1.2 g Fragrance oil, 0.8 g Isopropyl myristate and 0.5 g precursor | J | 8 g of a 1.75w % Aerosil 300 dispersion in 0.1M HCl | 5 min. at 8000rpm (IKA ultraturrax S25N-10G) | d | No second shell component |
| K | Oil in water | 4 g fragrance oil and 1 g precursor | AW | 16 g of a 1.25w % $Al_2O_3$ nanopowder dispersion in DI | 1 min. at 13500rpm (IKA ultraturrax S25N-10G) | c | No second shell component |
| N | Water in oil | 0.1 g of precursor, 0.05 g of Aerosil R816 and 4.85 g of hexyl salicylate | K | 0.4 g of a 1w % Allura red aqueous solution | 5 min. at 2500rpm (vortex mixer). | d | No second shell component |
| AA | Oil in water | 20 g fragrance oil and 5 g of precursor | AZ | 80 g of a 2.5w % Aerosil 300 dispersion in 0.1M HCl | 1 min. at 6000rpm (IKA ultraturrax S25N-25) | b | Step 1) 1 g SnCl2, 0.5 g HCL cc, 98.5 g DI water Step 2) 0.05 g PdCl2, 0.5 g HCl cc., 100 g DI water Step 3) 3 g NiSO4($H_2O$)6, 10 g NaPO2H2 and 87 g DI water. Conditions h |
| AB | Oil in water | 4 g fragrance oil and 1 g precursor | AP | 16 g of a 1.25w % Aerosil 300 dispersion in 0.1M HCl | 5 min. at 8000rpm (IKA ultraturrax S25N-10G) | c | No second shell component |
| AC | Oil in water | 4 g fragrance oil and 1 g precursor | AY | 16 g of a 1.25w % Aerosil 300 dispersion in 0.1M HCl | 5 min. at 8000rpm (IKA ultraturrax S25N-10G) | c | 1 mL of 1M $CaCl_2$ aqueous solution and 1 mL of 1 M $Na_2CO_3$ aqueous solution. Conditions g |
| AD | Water in oil | 0.1 g of precursor, 0.05 g of Aerosil R816 and 4.85 g of hexyl salicylate | K | 0.4 g of a 1w % Allura red aqueous solution | 5 min. at 2500rpm (vortex mixer). | d | 1 g of TEOS. Conditions e |

TABLE 3-continued

| | | | | | | | |
|---|---|---|---|---|---|---|---|
| | Section A-Comparative example |

| | | | | | | | |
|---|---|---|---|---|---|---|---|
| W | Oil in water | 2 g fragrance oil and 0.5 g precursor | TEOS | 8 g of a 1.75w % Aerosil 300 dispersion in 0.1M HCl | 1 min. at 8000rpm (IKA ultraturrax S25N-10G) | d | 1 g of 10w % of Sodium silicate(aq.) solution. Conditions e |

| | | | | | | | |
|---|---|---|---|---|---|---|---|
| | Section B |

| | | | | | | | |
|---|---|---|---|---|---|---|---|
| AF | Oil in water | 4 g fragrance oil and 1 g precursor | O | 16 g of a 1.25w % Aerosil 300 dispersion in 0.1M HCl | 1 min. at 13400rpm (IKA ultraturrax S25N-10G) | b | 1 g of 10w % of Sodium silicate(aq.) solution. Conditions f |
| AH | Oil in water | 4 g fragrance oil and 1 g precursor | P | 16 g of a 1.25w % Aerosil 300 dispersion in 0.1M HCl | 1 min. at 13400rpm (IKA ultraturrax S25N-10G) | b | 1 g of 10w % of Sodium silicate(aq.) solution. Conditions f |
| AJ | Oil in water | 4 g fragrance oil and 1 g precursor | R | 16 g of a 1.25w % Aerosil 300 dispersion in 0.1M HCl | 1 min. at 13400rpm (IKA ultraturrax S25N-10G) | b | 1 g of 10w % of Sodium silicate(aq.) solution. Conditions f |

| | | | | | | | |
|---|---|---|---|---|---|---|---|
| | Section B-Comparative Examples |

| | | | | | | | |
|---|---|---|---|---|---|---|---|
| AE | Oil in water | 4 g fragrance oil and 1 g precursor | O | 16 g of a 1.25w % Aerosil 300 dispersion in 0.1M HCl | 1 min. at 13400rpm (IKA ultraturrax S25N-10G) | b | No second shell component |
| AG | Oil in water | 4 g fragrance oil and 1 g precursor | P | 16 g of a 1.25w % Aerosil 300 dispersion in 0.1M HCl | 1 min. at 13400rpm (IKA ultraturrax S25N-10G) | b | No second shell component |
| AI | Oil in water | 4 g fragrance oil and 1 g precursor | R | 16 g of a 1.25w % Aerosil 300 dispersion in 0.1M HCl | 1 min. at 13400rpm (IKA ultraturrax S25N-10G) | b | No second shell component |
| AK | Oil in water | 4 g fragrance oil and 1 g precursor and 0.26 g MethylTriEthoxySilane | P | 16 g of a 1.25w % Aerosil 300 dispersion in 0.1M HCl | 1 min. at 13400rpm (IKA ultraturrax S25N-10G) | b | No second shell component |
| AL | Oil in water | 4 g fragrance oil and 1 g precursor and 0.26 g MethylTriEthoxySilane | P | 16 g of a 1.25w % Aerosil 300 dispersion in 0.1M HCl | 1 min. at 13400rpm (IKA ultraturrax S25N-10G) | b | 1 g of 10w % of Sodium silicate(aq.) solution. Conditions f |
| AM | Oil in water | 4 g fragrance oil and 1 g precursor and 0.65 g MethylTriEthoxySilane | P | 16 g of a 1.25w % Aerosil 300 dispersion in 0.1M HCl | 1 min. at 13400rpm (IKA ultraturrax S25N-10G) | b | No second shell component |
| AN | Oil in water | 4 g fragrance oil and 1 g precursor and 0.65 g MethylTriEthoxySilane | P | 16 g of a 1.25w % Aerosil 300 dispersion in 0.1M HCl | 1 min. at 13400rpm (IKA ultraturrax S25N-10G) | b | 1 g of 10w %of Sodium silicate(aq.) solution. Conditions f |
| AO | Oil in water | 4 g fragrance oil and 1 g precursor and 1.3 g MethylTriEthoxySilane | P | 16 g of a 1.25w % Aerosil 300 dispersion in 0.1M HCl | 1 min. at 13400rpm (IKA ultraturrax S25N-10G) | b | No second shell component |
| AP | Oil in water | 4 g fragrance oil and 1 g precursor and 1.3 g MethylTriEthoxySilane | P | 16 g of a 1.25w % Aerosil 300 dispersion in 0.1M HCl | 1 min. at 13400rpm (IKA ultraturrax S25N-10G) | b | 1 g of 10w % of Sodium silicate(aq.) solution. Conditions f |

| | | | | | | | |
|---|---|---|---|---|---|---|---|
| | Section C |

| | | | | | | | |
|---|---|---|---|---|---|---|---|
| AU | Oil in water | 2 g fragrance oil and 1.2 g precursor | AAA | 16 g of a 3w % Aerosil 300 dispersion in 0.1M HCl | 1 min. at 21400rpm (IKA ultraturrax S25N-10G) | b | No second shell component |
| AV | Oil in water | 4 g fragrance oil and 1 g of precursor | AW | 16 g of a 1.25w % Aerosil 300 dispersion in 0.1M HCl | 1 min. at 24000rpm (IKA ultraturrax S25N-10G) | c | 2 g of 10w % of Sodium silicate(aq.) solution. Conditions f |

| | | | | | | | |
|---|---|---|---|---|---|---|---|
| | Section C-Comparative Examples |

| | | | | | | | |
|---|---|---|---|---|---|---|---|
| B | Oil in water | 2 g fragrance oil and 0.5 g precursor | J | 8 g of a 1.75w % Aerosil 300 dispersion in 0.1M HCl | 5 min. at 8000rpm (IKA ultraturrax S25N-10G) | d | No second shell component |
| AQ | Oil in water | 1.6 g fragrance oil and 0.4 g precursor | AW | 8 g of a 3w % Aerosil 300 dispersion in 0.1M HCl | 1 min. at 24000rpm (IKA ultraturrax S25N-10G) | c | No second shell component |
| AR | Oil in water | 1.75 g fragrance oil and 0.75 g precursor | AW | 8 g of a 3w % Aerosil 300 dispersion in 0.1M HCl | 1 min. at 24000rpm (IKA ultraturrax S25N-10G) | c | No second shell component |
| AS | Oil in water | 3 g fragrance oil and 1.2 g precursor | AAA | 16 g of a 3w % Aerosil 300 dispersion in 0.1M HCl | 1 min. at 17400rpm (IKA ultraturrax S25N-10G) | b | No second shell component |
| AT | Oil in water | 4 g fragrance oil and 1 g of precursor | AAD | 16 g of a 1.25w % Aerosil 300 dispersion in 0.1M HCl | 1 min. at 24000rpm (IKA ultraturrax S25N-10G) | c | 2 g of 10w % of Sodium silicate(aq.) solution. Conditions f |
| AW | Oil in water | 4.75 g fragrance oil and 0.25 g of precursor | AX | 16 g of a 0.20w % Aerosil 300 dispersion in 0.1M HCl | 1 min. at 3000rpm (IKA ultraturrax S25N-10G) | b | No second shell component |

TABLE 3-continued

Section D

| | | | | | | | |
|---|---|---|---|---|---|---|---|
| AAA | Oil in water | 4 g fragrance oil and 1 g of precursor | AY | 16 g of a 1.25w % Aerosil 300 dispersion in 0.1M HCl | 5 min. at 800rpm (IKA ultraturrax S25N-10G) | c | 2 g of 10w % of Sodium silicate(aq.) solution. Conditions f |
| AAB | Oil in water | 4 g fragrance oil and 1 g of precursor | AAC | 16 g of a 2.5w % Aerosil 300 dispersion in 0.1M HCl | 1 min. at 13500rpm (IKA ultraturrax S25N-10G) | b | 2 g of 10w % of Sodium silicate(aq.) solution. Conditions f |
| AAC | Oil in water | 20 g fragrance oil and 5 g of precursor | AZ | 80 g of a 2.5w % Aerosil 300 dispersion in 0.1M HCl | 1 min. at 6000rpm (IKA ultraturrax S25N-25) | b | 2 g of 10w % of Sodium silicate(aq.) solution. Conditions f |

Section D-Comparative Examples

| | | | | | | | |
|---|---|---|---|---|---|---|---|
| AAD | Oil in water | 1.6 g fragrance oil and 0.4 g of precursor | TEOS | 8 g of a 0.5w % Aerosil 300 dispersion in 0.1M HCl | 1 min. at 8000rpm (IKA ultraturrax S25N-10G) | b | 1 g of 10w % of Sodium silicate(aq.) solution. Conditions f |
| AAE | Oil in water | 1.6 g fragrance oil and 0.4 g of precursor | Dynasylan 40 | 8 g of a 0.5w % Aerosil 300 dispersion in 0.1M HCl | 1 min. at 8000rpm (IKA ultraturrax S25N-10G) | b | 1 g of 10w % of Sodium silicate(aq.) solution. Conditions f |
| AAF | Oil in water | 1.6 g fragrance oil and 0.4 g of precursor | TBOS | 8 g of a 0.5w % Aerosil 300 dispersion in 0.1M HCl | 1 min. at 8000rpm (IKA ultraturrax S25N-10G) | d | 1 g of 10w % of Sodium silicate(aq.) solution. Conditions f |
| AX | Oil in water | 4 g fragrance oil and 1 g of precursor | AAB | 16 g of a 1.25w % Aerosil 300 dispersion in 0.1M HCl | 5 min. at 8000rpm (IKA ultraturrax S25N-10G) | c | 2 g of 10w % of Sodium silicate(aq.) solution. Conditions f |
| AY | Oil in water | 4 g fragrance oil and 1 g of precursor | G | 16 g of a 1.25w % Aerosil 300 dispersion in 0.1M HCl | 5 min. at 8000rpm (IKA ultraturrax S25N-10G) | | 2 g of 10w % of Sodium silicate(aq.) solution. Conditions f |

Conditions Referenced in Table 3 a. Menthol menthyl lactate (MML) was prepared by mixing Menthol and Menthyl Lactate at a weight ratio of 1:1 which yields a liquid at room temperature (U.S. Pat. No. 6,897,195B2 discloses how such mixture can be made, the disclosure of which is incorporated herein by reference).

b. Curing 4 h at RT, 16 h at 50° C. and 96 h at 70° C.

c. Curing at 50° C. for 3 weeks d. Curing at RT for over 5 weeks e. The slurry was diluted 20× in 0.1HCl and treated with the second shell component precursor solution, which was added dropwise using a plastic pipette under constant agitation of 350 RPM using an overhead stirrer, at room temperature and pH 1.2. The capsules were kept under agitation at 300 RPM for 24 hours, then centrifuged for 10 minutes at 2500 rpm and re-dispersed in DI water/ f. The slurry was diluted 4× in 0.1HCl and treated with a controlled addition (10 μl per minute) of the second shell component precursor solution, using a suspended magnetic stirrer reactor at 350 RPM, at room temperature. The pH was kept constant at pH 7 using 1M HCl(aq) and 1M NaOH (aq) solutions. The capsules were kept under agitation at 300 RPM per 24 hours, then centrifuged per 10 minutes at 2500 rpm and re-dispersed in DI water.

g. The slurry is diluted 10× in Di water and treated with controlled addition of aqueous $CaCl_2$ (1 M, 1 ml) and $Na_2CO_3$ (1 M, 1 ml) over 1 hour using a suspended magnetic stirrer reactor at 350 RPM. The pH was kept constant at pH 7 using 1M HCl(aq) and 1M NaOH (aq) solutions. The capsules are kept under agitation at 300 RPM per 24 hours, then centrifuged per 10 minutes at 2500 rpm and re-dispersed in DI water.

h. Before each step and after step (3), the slurry must be washed with 10 g DI water, centrifuged for 10 minutes at 1500 rpm and separating the supernatant, 3 times. Step (1) and (2) slurry is added to solution, and the mixture is shaken with lab shaker for 10 minutes at RT. Step (3) slurry is added to solution and is shaken with overhead mixer at 150 rpm for 1 h at 60 C.

TABLE 4

Examples results
Section A

| Sample ID | Mean Diameter (nm) | CoV PSD (%) | Mean Shell Thickness (um) | Thickness to Diameter ratio (%) | Effective core to shell ratio | Shell % organic | Nominal wall tension (N/m) | Shell Permeability (%) | Survive drying |
|---|---|---|---|---|---|---|---|---|---|
| F | 24.8 | 33.5 | | | | 0% | 12.3 | | Yes |
| G | 31.8 | 30.5 | 768.8 | 2.4% | 85:15 | 0% | 2.4 | | Yes |
| H | 31.8 | 30.5 | 868.3 | 2.7% | 84:16 | 0% | 2.6 | | Yes |
| L | 62.3 | 18.2 | | | | 0% | | | Yes |
| Q | 15.8 | 37.2 | | | | 0% | | | Yes |
| S | 90.5 | 38.6 | 437.0 | 0.5% | 97:3 | 0% | 3.8 | 34.1% | Yes |
| T | 24.4 | 27.2 | 675.5 | 2.8% | 84:16 | 0% | 2.1 | 11.9% | Yes |
| Z | 16.4 | 38.3 | 526.1 | 3.20% | 82:18 | 0% | | | Yes |
| C | 31.8 | 30.5 | 768.8 | 2.4% | 86:14 | 0% | 1.6 | | Yes |
| E | 17.4 | 39.4 | 562.0 | 3.2% | 82:18 | 0% | 4.6 | | Yes |
| I | 20.0 | 31.8 | 427.3 | 2.1% | 88:12 | 0% | 5.3 | | Yes |

TABLE 4-continued

| | | | | | | | | |
|---|---|---|---|---|---|---|---|---|
| J | 17.1 | 31.9 | 475.1 | 2.8% | 84:16 | 0% | 1.6 | Yes |
| K | | | | | | 0% | | Yes |
| AA | 29.50 | 25.6 | | | | 0% | | Yes |
| AB | 55.75 | 31.6 | | | | 0% | | Yes |
| AC | 33.25 | 30.3 | | | | 0% | | Yes |

Section A-Comparative Example

| | | | | | | | | |
|---|---|---|---|---|---|---|---|---|
| W | 21.3 | 39.1 | Footnote "a" | | | 0% | | No |

Section B

| | | | | | | | | |
|---|---|---|---|---|---|---|---|---|
| AF | 22.1 | 30.6 | | | | 1.8% | 36% | Yes |
| AH | 25.5 | 33.8 | | | | 4.2% | 17% | Yes |
| AJ | 25.6 | 33.9 | | | | 3.4% | 27% | Yes |

Section B-Comparative Examples

| | | | | | | | | |
|---|---|---|---|---|---|---|---|---|
| AE | 22.1 | 30.6 | | | | 1.8% | 91% | Yes |
| AG | 25.5 | 33.8 | | | | 4.2% | 96% | Yes |
| AI | 25.6 | 33.9 | | | | 3.4% | 74% | Yes |
| AK | 32.2 | 40.5 | | | | 6.8% | 98% | Yes |
| AL | 32.2 | 40.5 | | | | 6.8% | 52% | Yes |
| AM | 32.4 | 35.1 | | | | 9% | 71% | Yes |
| AN | 32.4 | 35.1 | | | | 9% | NA[b] | Yes |
| AO | 34.3 | 37.6 | | | | 12% | 70% | Yes |
| AP | 34.3 | 37.6 | | | | 12% | NA[b] | Yes |

Section C

| | | | | | | | | |
|---|---|---|---|---|---|---|---|---|
| AU | 14.4 | 36 | 408 | 2.8% | 84:16 | 0% | 23% | Yes |
| AV | 41.4 | 34 | 311 | 0.8% | 95:5 | 0% | 29% | Yes |

Section C-Comparative Examples

| | | | | | | | | |
|---|---|---|---|---|---|---|---|---|
| B | 16.2 | 32.0 | 646.0 | 4.0% | 78:22 | 0% | 1.2 | 83% | Yes |
| AQ | 5.28 | 36.63 | 103.5 | 2.0% | 90:10 | 0% | | 100% | Yes |
| AR | 10.5 | 55 | 164.1 | 1.6% | 87:13 | 0% | | 100% | Yes |
| AS | 13.06 | 51 | 515.7 | 4.0% | 77:23 | 0% | | 74% | Yes |
| AT | 31 | 31.2 | 64.2 | 0.2% | 99:1 | 0% | | 65% | Yes |
| AW | 144.9 | 15.14 | 287.5 | 0.2% | 99:1 | 0% | | 100% | Yes |

Section D

| | | | | | | | | |
|---|---|---|---|---|---|---|---|---|
| AAA | 37.5 | 24.7 | 371.2 | 1.0% | 92:8 | 0% | 20% | yes |
| AAB | 25.4 | 53.7 | 160.5 | 0.6% | 94:6 | 0% | 13% | yes |
| AAC | 26.6 | 33.5 | | | | 0% | 25% | yes |

Section D-Comparative Examples

| | | | | | | | | |
|---|---|---|---|---|---|---|---|---|
| AX | 37 | 32.5 | 395.2 | 1.1% | 92:8 | 0% | 79% | yes |
| AY | 40.3 | 52.36 | Footnote "a" | | | 0% | 89% | No |
| AAD | 43.6 | 56.4 | Footnote "a" | | | 0% | 81% | No |
| AAE | 34.6 | 58.3 | Footnote "a" | | | 0% | 79% | No |
| AAF | 14.5 | 41.5 | Footnote "a" | | | 0% | 100% | No |

[a] Comparative examples: capsules collapsed when dried on microslide, the measurement was not possible.
[b] Second shell component was not placed as slurry was too viscous.

For all examples below, the following method was used to test if capsules collapse: 0.1 gr of slurry was diluted into 5 gr of DI water. Of this dilution, a few drops were added onto a microslide, and the capsules were let air drying until all water had evaporated. When observing the dry slurry with an optical microscope, one could then determine if capsules were not collapsing if they maintain their initial spherical shape.

The below Examples 8-1, and Comparative Examples 8-2 and 8-3 show the importance of using precursors as disclosed in this invention in combination with nanoparticles and a second shell component as disclosed in this invention, in order to obtain low shell permeabilities.

Example 8-1

The water phase was prepared by weighing 1.25 gr of Aerosil 300 and bringing the total weight to 100 gr with 0.1M HCl. The nanoparticles were dispersed by sonicating the mixture in an ultrasonic bath for at least 30 minutes or until no more solid sediments.

The oil phase was prepared by mixing and homogenizing 1 gr of precursor AY with 4 gr of a fragrance mixture of formula A (see below).

16 gr of the water phase was mixed with the above oil phase with an ultraturrax (S25N-Og mixing tool from IKA) at 13500 rpm for 1 minute. The resulting mixture was capped with an airtight lid, let standing for 4 hours at room temperature, and an additional 3 weeks at 50 C. After 3 weeks at 50 C, the capsules slurry was formed. The capsules were not collapsing on a microslide.

The slurry was diluted 4× in 0.1HCl and treated with a controlled addition (10 μl per minute) of 2 gr of a 10 w % solution of Sodium Silicate (aq.), using a suspended magnetic stirrer reactor at 350 RPM, at room temperature. The pH was kept constant at pH 7 using 1M HCl(aq) and 1M NaOH (aq) solutions. The capsules were kept under agitation at 300 RPM per 24 hours, then centrifuged per 10 minutes at 2500 rpm and re-dispersed in DI water.

The resulting capsule slurry was put through the permeability test as disclosed in this invention, and the shell permeability % was 21% based on the permeability test.

Comparative Example 8-2

The water phase was prepared by diluting a 25 w % CTAC (aq.) solution (supplied by Sigma Aldrich) into DI water, to reach a concentration of 0.52 w % of CTAC.

The oil phase was made by mixing 40 gr of Fragrance of formula (A) and 10 gr of TEOS. The above oil phase was mixed with 100 gr of the above water phase using an ultraturrax mixer (S25N mixing tool from IKA), at 8500 rpm for 1 minute. The resulting emulsions pH was trimmed to 3.9 with the use of 1M NaOH (supplied by sigma Aldrich). Then, the emulsion was continuously stirred at 160 rpm with an overhead mixer and heated at 30 C for 17 hours in a jacketed reactor that was covered to avoid evaporation of water or any other components. After the 17-hour reaction time, capsules had formed. The capsules were collapsing when air dried.

The resulting capsule slurry was put through the permeability test as disclosed in this invention, and the shell permeability % was 67% based on the permeability test.

Comparative Example 8-3

Same as comparative example 8-1, except that after the capsule slurry was formed, the pH was trimmed to 3.2 and 5.7 g of TEOS was added dropwise over 320 minutes while the temperature was maintained at 30 C and mixing speed at 160 rpm with an overhead mixer. After all the TEOS was added, the slurry was mixed for an additional 18 hours at 30 C and 160 rpm with an overhead mixer, to obtain capsules. The capsules were not collapsing when air dried.

The resulting capsule slurry was put through the permeability test as disclosed in this invention, and the shell permeability % was 67% based on the permeability test.

Fragrance Formula (A):
Hexyl acetate 9 w %
Methyl dihydrojasmonate 9 w %
Tetrahydrolinalol 9 w %
α-Ionone 9 w %
Lilial 18 w %
Hexylcinnamyl aldehyde 18 w %
Hexyl salicylate 18 w %
Verdyl Acetate 10 w %

The below Examples 9-1 and comparative examples 9-2 and 9-3 show the importance of using precursors as disclosed in this invention in combination with nanoparticles and a second shell component as disclosed in this invention, in order to obtain low shell permeabilities.

Example 9-1

Example ID AAA from Table 3. Capsules were not collapsing when left air drying and had a permeability % of 20% in the permeability test.

Comparative Example 9-2

In a 50 m round bottomed flask equipped with a magnetic stir bar, 4 gr of 0.01M HCl (a.q.) was combined with 3 gr Phenyltriethoxysilane (PhTEOS). Initially the two phases were not miscible. Next, the mixture was vigorously stirred at 1000 rpm while trimming the pH to 2 with 0.1M NaOH. The mixture was stirred at 1000 rpm and Room temperature until obtaining a homogeneous mixture. This yielded a precursor mixture.

Next, 1.5 gr of the same fragrance as for example AAA was added to 48.5 gr of water containing 18 mg of a 50 w % CTAC solution. The resulting mixture was stirred with a magnetic stirbar for 30 minutes at room temperature, after which 2.5 ml of 25 w % ammonia was added and 5 ml of the above prepared precursor mixture. This was stirred for an additional 2 hours, after which capsules were formed. The capsules were collapsing after left air drying. The capsules had a permeability % of 99% based on the permeability test.

Comparative Example 9-3

144 gr of the same fragrance as for example AAA was weighed in a vessel. In a separate vessel, 96 gr of a 1 w % CTAC solution was created by mixing 3.84 gr of a 25 w % CTAC solution and bringing the mass to 96 gr with DI water. The above fragrance was mixed with the above surfactant mixture with an IKA ultraturrax mixer (S25N mixing tool) at 8000 rpm for 5 minutes.

Next, 144 gr of water with a pH of 3.8 (trimmed with Concentrated HCl) was added to the above prepared emulsion system.

Next, 27 gr of a mixture containing 26.73 gr of TEOS and 0.27 gr of DimethylDiethoxysilane was added dropwise to the emulsion system under constant mixing. When all of the precursor was added, the mixture was heated to 50 C and stirred at 200 rpm with an overhead mixer in a jacketed reactor for 2 hours.

The resulting capsules were collapsing when left air drying, and the capsules had a permeability % of 77% as determined by the permeability test.

The below Examples 10-1, and 10-3 and Comparative Examples 10-2, 10-4, 10-5 and 10-6 show the importance in choosing the right precursors, nanoparticles and second shell components as disclosed in this invention to obtain capsules with low permeabilities.

Example 10-1

The water phase was prepared by weighing 1.25 gr of Aerosil 300 and bringing the total weight to 100 gr with 0.1M HCl. The nanoparticles were dispersed by sonicating the mixture in an ultrasonic bath for at least 30 minutes or until no more solid sediments.

The oil phase was prepared by mixing and homogenizing 1 gr of precursor AY with 3.5 gr of Isopropyl Myristate and 0.5 gr of Verdyl acetate. 16 gr of the above water phase was mixed with the above oil phase with an ultraturrax (S25N-10 g mixing tool from IKA) at 13500 rpm for 1 minute. The resulting mixture was capped with an airtight lid, let standing for 4 hours at room temperature, and an additional 3 weeks at 50 C.

After 3 weeks at 50 C, the capsules slurry was formed. The capsules were not collapsing on a microslide. No second shell component was added for this capsule, and the capsules permeability % was 40% based on the permeability test.

Comparative Example 10-2

Same process as for example ID AAC from Table 3, except that no second shell component was added. The capsules survived drying and the capsule permeability % was 98% based on the permeability test.

Example 10-3

Example ID AAC from Table 3. The capsules survived drying and the capsule permeability % was 25% based on the permeability test.

Comparative Example 10-4

The oil phase was prepared by mixing 20 gr of TEOS, 115 gr of Isopropyl Myristate and 15 gr of Verdyl acetate.

Next, the water phase was prepared by weighing 10 gr of a 25 w % CTAC (aq.) solution and bringing the weight to 150 gr with DI water to reach a CTAC concentration of 1.67 w %.

The two phases were mixed together with a Ultraturrax mixer (S25N tool from IKA) at 6000 rpm for 1 minute. Next, 50 g of Ludox TM50 was added and the system was further mixed at 8000 rpm for another 1 minute. Next, the pH was adjusted to 5 with 1M HCl.

To the above mixture, 50 gr of 10 w % PVOH in water (selvol 540) and 5 gr of a 25 w % sodium silicate in water were added. The pH was then readjusted to 4, and the system stirred at Room temperature at 200 rpm with an overhead mixer for 20 hours. The capsules were collapsing when left air drying on a microslide and the capsules permeability % was 92% based on the permeability test.

Comparative Example 10-5

Same as Comparative Example 10-4, except 40 gr of a 5 w % polyquaternium 7 aqueous solution was further added at the end after formation of capsules. The capsules were collapsing when left air drying on a microslide and the capsule permeability % was 83% based on the permeability test.

Comparative Example 10-6

Same process as for comparative example 10-2 above, except that 1.3 gr of a 5 w % solution of polyquaternium 7 aqueous solution was further added to 5 gr of slurry, and the mixture was stirred at 200 rpm with an overhead mixer for 15 minutes. The capsules survived drying and the capsule permeability % was 73% based on the permeability test.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A population of capsules, the capsules comprising:
an oil-based core comprising a benefit agent, and a substantially inorganic shell surrounding the core, wherein the shell comprises a first shell component comprising a condensed layer comprising a condensation of a precursor, wherein the precursor comprises at least one compound of Formula (I) or Formula (II):

$$(M^vO_zY_n)_w \quad \text{(Formula I)},$$

where M is one or more of silicon, titanium and aluminum, v is the valence number of M and is 3 or 4, z is from 0.5 to 1.6, each Y is independently selected from —OH, —OR$^2$, halo,

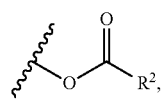

—NH$_2$, —NHR$^2$, —N(R$^2$)$_2$, and

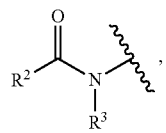

wherein R$^2$ is a C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, R$^3$ is a H, C$_1$ to C$_{20}$ alkyl, C$_1$ to C$_{20}$ alkylene, C$_6$ to C$_{22}$ aryl, or a 5-12 membered heteroaryl comprising from 1 to 3 ring heteroatoms selected from O, N, and S, n is from 0.7 to (v-1), and w is from 2 to 2000; or $$(M^vO_zY_nR^1_p)_w \quad \text{(Formula II)},$$

where M is one or more of silicon, titanium and aluminum, v is the valence number of M and is 3 or 4, z is from 0.5 to 1.6, each Y is independently selected from —OH, —OR$^2$, halo,

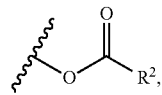

—NH$_2$, —NHR$^2$, —N(R$^2$)$_2$,

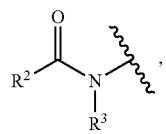

wherein $R^2$ is selected from a $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, $R^3$ is a H, $C_1$ to $C_{20}$ alkyl, $C_1$ to $C_{20}$ alkylene, $C_6$ to $C_{22}$ aryl, or a 5-12 membered heteroaryl comprising from 1 to 3 ring heteroatoms selected from O, N, and S, n is from 0 to (v-1), each $R^1$ is independently selected from a $C_1$ to $C_{30}$ alkyl, a $C_1$ to $C_{30}$ alkylene, a $C_1$ to $C_{30}$ alkyl substituted with one or more of a halogen, —$OCF_3$, —$NO_2$, —CN, —NC, —OH, —OCN, —NCO, alkoxy, epoxy, amino, mercapto, acryloyl, $CO_2H$, $CO_2$alkyl, aryl, and heteroaryl, or a $C_1$ to $C_{30}$ alkylene substituted with one or more of a halogen, —$OCF_3$, —$NO_2$, —CN, —NC, —OH, —OCN, —NCO, alkoxy, epoxy, amino, mercapto, acryloyl, $CO_2H$, $CO_2$alkyl, aryl, and heteroaryl, p is present in an amount up to pmax, and w is from 2 to 2000;

wherein pmax=60/[9*Mw($R^1$)+8], where Mw($R^1$) is the molecular weight of the $R^1$ group;

wherein the first shell component comprises up to 5 wt % of organic content;

wherein said population has a mean volume weighted capsule diameter of about 10 micrometers to about 200 micrometers, an average shell thickness of about 170 nm to about 1000 nm; and wherein the mean volumetric core-shell ratio is from about 80:20 to about 98:2;

wherein the oil-based core is a liquid at room temperature;

wherein said population has a shell permeability from about 0.01% to about 40%.

2. The population of capsules according to claim 1, wherein said population has a shell permeability from about 0.01% to about 30%.

3. The population of capsules according to claim 1, wherein said population has a shell permeability from about 0.01% to about 20%.

4. The population of capsules according to claim 1, wherein the benefit agent comprises at least one of chromogens and dyes, perfume compositions, perfume raw materials, lubricants, silicone oils, waxes, hydrocarbons, higher fatty acids, essential oils, lipids, skin coolants, vitamins, sunscreens, antioxidants, catalysts, malodor reducing agents, odor-controlling materials, softening agents, insect and moth repelling agents, colorants, pigments, pharmaceuticals, pharmaceutical oils, adhesives, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, color maintenance agents, color restoration/rejuvenation agents, anti-fading agents, anti-abrasion agents, wear resistance agents, fabric integrity agents, anti-wear agents, anti-pilling agents, defoamers, anti-foaming agents, UV protection agents, sun fade inhibitors, anti-allergenic agents, fabric comfort agents, shrinkage resistance agents, stretch resistance agents, stretch recovery agents, skin care agents and natural actives, dyes, phase change materials, fertilizers, nutrients, or herbicides.

5. The population of capsules according to claim 4, wherein the benefit agent comprises perfume compositions.

6. The population of capsules according to claim 4, wherein the oil-based core comprising a benefit agent, further comprises a core modifier.

7. The population of capsules according to claim 1, wherein the first shell component comprises up to 2 wt % of organic content.

8. The population of capsules according to claim 1, wherein the first shell component comprises inorganic nanoparticles that are at least one of metal nanoparticles, mineral nanoparticles, metal-oxide nanoparticles or semimetal oxide nanoparticles.

9. The population of capsules according to claim 8, where the inorganic nanoparticles comprise at least one of $SiO_2$, $TiO_2$, $Al_2O_3$, $Fe_2O_3$, $Fe_3O_4$, $CaCo_3$, clay, silver, gold, and copper.

10. The population of capsules according to claim 1, wherein the shell further comprises an inorganic second shell component surrounding the first shell component, wherein the inorganic second shell component comprises an inorganic second shell material that is at least one of $SiO_2$, $TiO_2$, $Al_2O_3$, $CaCO_3$, $Ca_2SiO_4$, $Fe_2O_3$, $Fe_3O_4$, iron, silver, nickel, gold, copper, and clay.

11. The population of capsules according to claim 10, wherein the second shell component comprises at least one of $SiO_2$ or $CaCO_3$.

12. The population of capsules according to claim 1, wherein for formula (I): M is Si, Y is $OR_2$, and $R_2$ is a linear or branched alkyl chain comprising 1 to 4 carbon atoms.

13. The population of capsules according to claim 1, wherein for formula (I): M is Si, Y is $OR_2$ and $R_2$ is an ethyl group.

14. The population of capsules according to claim 1, wherein precursors of formula (I) have a molecular weight between 700 Da and 30,000 Da.

15. The population of capsules according to claim 14, wherein precursors of formula (I) have a degree of branching between 0.2 and 0.6.

16. The population of capsules according to claim 1, wherein precursors of formula (I) have a PDI between 1 and 20.

17. The population of capsules according to claim 1, wherein precursors of Formula (I) can be combined with tetraethoxysilane (TEOS), tetramethoxysilane (TMOS), and tetrabutoxysilane (TBOS).

18. The population of capsules according to claim 1, wherein for formula (II): M is Si, Y is $OR_2$, and $R_2$ is a linear or branched alkyl chain comprising 1 to 4 carbon atoms.

19. The population of capsules according to claim 1, wherein for formula (II): M is Si, Y is $OR_2$ and $R_2$ is an ethyl group.

20. The population of capsules according to claim 1, wherein precursors of formula (II) have a molecular weight between 700 Da and 30,000 Da.

21. The population of capsules according to claim 20, wherein precursors of formula (II) have a degree of branching between 0.2 and 0.6.

22. The population of capsules according to claim 1, wherein precursors of formula (II) have a PDI between 1 and 20.

23. The population of capsules according to claim 1, wherein the capsules have a mean nominal wall tension of about 0.1 N/m to about 50 N/m.

24. The population of capsules according to claim 23, wherein the capsules have a mean nominal wall tension of about 0.5 N/m to about 30 N/m.

* * * * *